US009943596B2

(12) United States Patent
Lee et al.

(10) Patent No.: US 9,943,596 B2
(45) Date of Patent: Apr. 17, 2018

(54) COMBINATION THERAPY USING DUAL INHIBITOR OF C-MET AND EGFR AND IGF-1R INHIBITOR

(71) Applicant: Samsung Electronics Co., Ltd., Suwon-si, Gyeonggi-do (KR)

(72) Inventors: Jimin Lee, Suwon-si (KR); Bo Gyou Kim, Seoul (KR); Seungja Oh, Hwaseong-si (KR); Kyung Ah Kim, Seongnam-si (KR); Powei Lin, Hwaseongi-si (KR); Saet Byoul Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/949,303

(22) Filed: Nov. 23, 2015

(65) Prior Publication Data

US 2016/0144028 A1 May 26, 2016

(30) Foreign Application Priority Data

Nov. 21, 2014 (KR) ........................ 10-2014-0163791

(51) Int. Cl.

*A61K 39/395* (2006.01)
*A61K 31/4985* (2006.01)
*G01N 33/574* (2006.01)
*A61K 31/00* (2006.01)
*C07K 16/28* (2006.01)
*G01N 33/74* (2006.01)
*A61K 39/00* (2006.01)

(52) U.S. Cl.

CPC ........ *A61K 39/39558* (2013.01); *A61K 31/00* (2013.01); *A61K 31/4985* (2013.01); *C07K 16/2863* (2013.01); *G01N 33/57492* (2013.01); *G01N 33/74* (2013.01); *A61K 2039/505* (2013.01); *C07K 2317/24* (2013.01); *C07K 2317/31* (2013.01); *C07K 2317/622* (2013.01); *G01N 2333/65* (2013.01); *G01N 2800/52* (2013.01)

(58) Field of Classification Search

CPC .......... A61K 39/39558; C07K 16/2863; C07K 2317/24; C07K 2317/31; C07K 2317/622
USPC ........................................................ 424/136.1
See application file for complete search history.

(56) References Cited

U.S. PATENT DOCUMENTS

2009/0226443 A1 9/2009 Filvaroff et al.
2010/0076178 A1 3/2010 Ghayur et al.
2012/0034228 A1 2/2012 Kufer et al.
2012/0065380 A1 3/2012 Yoo et al.
2014/0141000 A1 5/2014 Chiu et al.
2016/0144027 A1* 5/2016 Shim ................ A61K 39/39558 424/139.1

FOREIGN PATENT DOCUMENTS

KR 2010-0125033 A 11/2010

OTHER PUBLICATIONS

Gallick et al. (Future Med Chem. Jan. 2012 ; 4(1): 107-119.*
Wang et al. PLOS ONE | DOI:10.1371/journal.pone.0128360 May 20, 2015.*
R&D Systems, (data sheet; catalogue # 358-MT; pp. 1-2; Mar. 30, 2017).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410).*

* cited by examiner

*Primary Examiner* — Lynn A Bristol
(74) *Attorney, Agent, or Firm* — Leydig, Voit & Mayer, Ltd.

(57) ABSTRACT

A method of preventing and/or treating a cancer, the method including co-administering a dual inhibitor of c-Met and EGFR (hereinafter, 'c-Met/EGFR dual inhibitor') and an IGF-1R inhibitor to a subject in need thereof and a use of IGF-1R as a marker for resistance to a c-Met/EGFR dual inhibitor.

11 Claims, 9 Drawing Sheets

```
                    SEQUENCE LISTING


<160> NUMBER OF SEQ ID NOS: 133

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
  1               5


<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46

<400> SEQUENCE: 2

Phe Ile Arg Asn Lys Ala Asn Gly Tyr Thr Thr Glu Tyr Ser Ala Ser
  1               5                  10                  15

Val Lys Gly


<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46
```

<400> SEQUENCE: 3

Asp Asn Trp Phe Ala Tyr
1 5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
1 5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
1 5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr

<400> SEQUENCE: 6

Asp Asn Trp Leu Xaa Tyr
1 5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (9)
<223> OTHER INFORMATION: Xaa is Ser or Trp
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn

<400> SEQUENCE: 7

```
Lys Ser Ser Xaa Ser Leu Leu Ala Xaa Gly Asn Xaa Xaa Asn Tyr Leu
  1               5                  10                  15

Ala
```

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

```
Trp Xaa Ser Xaa Arg Val Xaa
  1               5
```

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
<223> OTHER INFORMATION: Xaa is Leu, Tyr, Phe or Met

<400> SEQUENCE: 9

```
Xaa Gln Ser Tyr Ser Xaa Pro Xaa Thr
  1               5
```

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
1 5 10 15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
1 5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
1 5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
1 5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
1 5

<210> SEQ ID NO 15
<211> LENGTH: 9
<212> TYPE: PRT
<213> ORGANISM: Artificial Sequence
<220> FEATURE:
<223> OTHER INFORMATION: Synthetic CDR-L3 derived from L3-3 clone

<400> SEQUENCE: 15

Ala Gln Ser Tyr Ser His Pro Phe Ser
1 5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

```
Gln Gln Ser Tyr Ser Arg Pro Phe Thr
  1               5
```

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti c-Met humanized antibody(huAbF46-H4)

<400> SEQUENCE: 17

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115
```

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti c-Met humanized antibody(huAbF46-H4)

<400> SEQUENCE: 18

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg
```

<210> SEQ ID NO 19
<211> LENGTH: 114
<212> TYPE: PRT
<213> ORGANISM: Artificial Sequence -continued
<220> FEATURE:
<223> OTHER INFORMATION: Synthetic light chain variable region of anti
c-Met humanized antibody(huAbF46-H4)

<400> SEQUENCE: 19

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gly Gln
                 85                  90                  95

Ser Tyr Ser Arg Pro Leu Thr Phe Gly Gln Gly Thr Lys Val Glu Ile
            100                 105                 110

Lys Arg
```

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
c-Met humanized antibody(huAbF46-H4)

<400> SEQUENCE: 20

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ala Gln
                 85                  90                  95

Ser Tyr Ser His Pro Phe Ser Phe Gly Gln Gly Thr Lys Val Glu Ile
            100                 105                 110

Lys Arg
```

<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
c-Met humanized antibody(huAbF46-H4)

<400> SEQUENCE: 21

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30
```

```
Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Phe Thr Phe Gly Gln Gly Thr Lys Val Glu Ile
            100                 105                 110

Lys Arg


<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
  1               5


<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
  1               5


<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
  1               5


<210> SEQ ID NO 25
<211> LENGTH: 8
<212> TYPE: PRT
<213> ORGANISM: Artificial Sequence
<220> FEATURE:
<223> OTHER INFORMATION: Synthetic CDR-H2 derived from YC244 clone

<400> SEQUENCE: 25

Arg Asn Asn Ala Asn Gly Asn Thr
  1               5


<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26
```

Arg Asn Lys Val Asn Gly Tyr Thr
1 5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
1 5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
1 5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
1 5 10 15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
1 5 10 15

Ala

<210> SEQ ID NO 31
<211> LENGTH: 17
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
1 5 10 15

Ala

<210> SEQ ID NO 32
<211> LENGTH: 17
<212> TYPE: PRT

<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
1 5 10 15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
1 5 10 15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
1 5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
1 5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
1 5

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
1 5

-continued

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gtttttctcg taacactttt aaatggtatc 60
cagtgtgagg tgaagctggt ggagtctgga ggaggcttgg tacagcctgg gggttctctg 120
agactctcct gtgcaacttc tgggttcacc ttcactgatt actacatgag ctgggtccgc 180
cagcctccag gaaaggcact tgagtggttg ggttttatta gaaacaaagc taatggttac 240
acaacagagt acagtgcatc tgtgaagggt cggttcacca tctccagaga taattcccaa 300
agcatcctct atcttcaaat ggacaccctg agagctgagg acagtgccac ttattactgt 360
gcaagagata actggtttgc ttactggggc caagggactc tggtcactgt ctctgcagct 420
agcaccaagg gcccatcggt cttccccctg gcaccctcct ccaagagcac ctctgggggc 480
acagcggccc tgggctgcct ggtcaaggac tacttccccg aaccggtgac ggtgtcgtgg 540
aactcaggcg ccctgaccag cggcgtgcac accttcccgg ctgtcctaca gtcctcagga 600
ctctactccc tcagcagcgt ggtgaccgtg ccctccagca gcttgggcac ccagacctac 660
atctgcaacg tgaatcacaa gcccagcaac accaaggtgg acaagaaagt tgagcccaaa 720
tcttgtgaca aaactcacac atgcccaccg tgcccagcac ctgaactcct ggggggaccg 780
tcagtcttcc tcttcccccc aaaacccaag gacaccctca tgatctcccg gacccctgag 840
gtcacatgcg tggtggtgga cgtgagccac gaagaccctg aggtcaagtt caactggtac 900
gtggacggcg tggaggtgca taatgccaag acaaagccgc gggaggagca gtacaacagc 960
acgtaccgtg tggtcagcgt cctcaccgtc ctgcaccagg actggctgaa tggcaaggag 1020
tacaagtgca aggtctccaa caaagccctc ccagccccca tcgagaaaac catctccaaa 1080
gccaaagggc agccccgaga accacaggtg tacaccctgc ccccatcccg ggaggagatg 1140
accaagaacc aggtcagcct gacctgcctg gtcaaaggct tctatcccag cgacatcgcc 1200
gtggagtggg agagcaatgg gcagccggag aacaactaca agaccacgcc tcccgtgctg 1260
gactccgacg gctccttctt cctctacagc aagctcaccg tggacaagag caggtggcag 1320
caggggaacg tcttctcatg ctccgtgatg catgaggctc tgcacaacca ctacacgcag 1380
aagagcctct ccctgtctcc gggtaaatga ctcgag 1416

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atggattcac aggcccaggt cctcatgttg 60
ctgctgctat cggtatctgg tacctgtgga gacattttga tgacccagtc tccatcctcc 120
ctgactgtgt cagcaggaga gaaggtcact atgagctgca agtccagtca gagtctttta 180
gctagtggca accaaaataa ctacttggcc tggcaccagc agaaaccagg acgatctcct 240
aaaatgctga taatttgggc atccactagg gtatctggag tccctgatcg cttcataggc 300
agtggatctg ggacggattt cactctgacc atcaacagtg tgcaggctga agatctggct 360
gtttattact gtcagcagtc ctacagcgct ccgctcacgt tcggtgctgg gaccaagctg 420
gagctgaaac gtacggtggc tgcaccatct gtcttcatct tcccgccatc tgatgagcag 480
ttgaaatctg gaactgcctc tgttgtgtgc ctgctgaata acttctatcc cagagaggcc 540
aaagtacagt ggaaggtgga taacgccctc caatcgggta actcccagga gagtgtcaca 600
gagcaggaca gcaaggacag cacctacagc ctcagcagca ccctgacgct gagcaaagca 660
gactacgaga aacacaaagt ctacgcctgc gaagtcaccc atcagggcct gagctcgccc 720
gtcacaaaga gcttcaacag gggagagtgt tgactcgag 759

<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy -continued

<400> SEQUENCE: 40

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
```

405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Tyr Met Ser Trp Val Arg Gln Ala Pro Gly Lys Gly Leu Glu Trp Leu
35 40 45

Gly Phe Ile Arg Asn Lys Ala Asn Gly Tyr Thr Thr Glu Tyr Ser Ala
50 55 60

Ser Val Lys Gly Arg Phe Thr Ile Ser Arg Asp Asn Ser Lys Asn Ser
65 70 75 80

Leu Tyr Leu Gln Met Asn Ser Leu Arg Ala Glu Asp Thr Ala Val Tyr
85 90 95

Tyr Cys Ala Arg Asp Asn Trp Phe Ala Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile

```
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

-continued

```
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Ala Ser
             20                  25                  30

Gly Asn Gln Asn Asn Tyr Leu Ala Trp His Gln Gln Lys Pro Gly Gln
         35                  40                  45

Pro Pro Lys Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
```

```
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
  1               5                  10                  15

Glu Pro Ala Ser Ile Ser Cys Lys Ser Ser Gln Ser Leu Leu Ala Ser
             20                  25                  30

Gly Asn Gln Asn Asn Tyr Leu Ala Trp His Leu Gln Lys Pro Gly Gln
         35                  40                  45

Ser Pro Gln Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Ala Ser
             20                  25                  30
```

-continued

```
Gly Asn Gln Asn Asn Tyr Leu Ala Trp Tyr Gln Gln Lys Pro Gly Gln
        35                  40                  45

Pro Pro Lys Leu Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215


<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47

gaggtgcagc tggtggagtc tgggggaggc ttggtccagc ctggagggtc cctgagactc     60

tcctgtgcag cctctggatt caccttcact gactactaca tgagctgggt ccgccaggct    120

ccagggaagg ggctggagtg gttgggcttt attagaaaca aagctaacgg ttacaccaca    180

gaatacagtg cgtctgtgaa aggcagattc accatctcaa gagataattc aaagaactca    240

ctgtatctgc aaatgaacag cctgaaaacc gaggacacgg ccgtgtatta ctgtgctaga    300

gataactggt ttgcttactg gggtcaagga accctggtca ccgtctcctc ggctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa atgactcgag                                    1350


<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

gaggtgcagc tggtggagtc tgggggaggc ttggtccagc ctggagggtc cctgagactc     60

tcctgtgcag cctctggatt caccttcact gactactaca tgagctgggt ccgccaggct    120
```

```
ccagggaagg ggctggagtg gttgggcttt attagaaaca aagctaacgg ttacaccaca    180

gaatacagtg cgtctgtgaa aggcagattc accatctcaa gagataattc aaagaactca    240

ctgtatctgc aaatgaacag cctgcgtgct gaggacacgg ccgtgtatta ctgtgctaga    300

gataactggt ttgcttactg gggtcaagga accctggtca ccgtctcctc ggctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacaa cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa atgactcgag                                    1350
```

```
<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

gaggttcagc tggtggagtc tggcggtggc ctggtgcagc caggggggctc actccgtttg     60

tcctgtgcag cttctggctt caccttcact gattactaca tgagctgggt gcgtcaggcc    120

ccgggtaagg gcctggaatg gttgggtttt attagaaaca aagctaatgg ttacacaaca    180

gagtacagtg catctgtgaa gggtcgtttc actataagca gagataattc caaaaacaca    240

ctgtacctgc agatgaacag cctgcgtgct gaggacactg ccgtctatta ttgtgctaga    300

gataactggt ttgcttactg ggccaaggg actctggtca ccgtctcctc ggctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacaaga aagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840
```

ggcgtggagg tgcataatgc caagacaaag ccgcgggagg agcagtacaa cagcacgtac 900
cgtgtggtca gcgtcctcac cgtcctgcac caggactggc tgaatggcaa ggagtacaag 960
tgcaaggtct ccaacaaagc cctcccagcc cccatcgaga aaaccatctc caaagccaaa 1020
gggcagcccc gagaaccaca ggtgtacacc ctgcccccat cccgggagga gatgaccaag 1080
aaccaggtca gcctgacctg cctggtcaaa ggcttctatc ccagcgacat cgccgtggag 1140
tgggagagca atgggcagcc ggagaacaac tacaagacca cgcctcccgt gctggactcc 1200
gacggctcct tcttcctcta cagcaagctc accgtggaca agagcaggtg gcagcagggg 1260
aacgtcttct catgctccgt gatgcatgag gctctgcaca accactacac gcagaagagc 1320
ctctccctgt ctccgggtaa atgactcgag 1350

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50
gacatcgtga tgacccagtc tccagactcc ctggctgtgt ctctgggcga gagggccacc 60
atcaactgca agtccagcca gagtctttta gctagcggca accaaaataa ctacttagct 120
tggcaccagc agaaaccagg acagcctcct aagatgctca ttatttgggc atctacccgg 180
gtatccgggg tccctgaccg attcagtggc agcgggtctg ggacagattt cactctcacc 240
atcagcagcc tgcaggctga agatgtggca gtttattact gtcagcaatc ctatagtgct 300
cctctcacgt tcggaggcgg taccaaggtg gagatcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660
tgactcgag 669

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51
gatattgtga tgacccagac tccactctcc ctgcccgtca cccctggaga gccggcctcc 60
atctcctgca agtccagtca gagtctttta gctagtggca accaaaataa ctacttggcc 120
tggcacctgc agaagccagg gcagtctcca cagatgctga tcatttgggc atccactagg 180
gtatctggag tcccagacag gttcagtggc agtgggtcag gcactgattt cacactgaaa 240
atcagcaggg tggaggctga ggatgttgga gtttattact gccagcagtc ctacagcgct 300
ccgctcacgt tcggacaggg taccaagctg gagctcaaac gtacggtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480

-continued

```
caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660

tgactcgag                                                            669
```

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52

```
gacatcgtga tgacccagtc tccagactcc ctggctgtgt ctctgggcga gagggccacc     60

atcaactgca agtccagcca gagtctttta gctagcggca accaaaataa ctacttagct    120

tggtaccagc agaaaccagg acagcctcct aagctgctca ttatttgggc atctacccgg    180

gtatccgggg tccctgaccg attcagtggc agcgggtctg ggacagattt cactctcacc    240

atcagcagcc tgcaggctga agatgtggca gtttattact gtcagcaatc ctatagtgct    300

cctctcacgt tcggaggcgg taccaaggtg gagatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660

tgactcgag                                                            669
```

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53

```
gatatccaga tgacccagtc cccgagctcc ctgtccgcct ctgtgggcga tagggtcacc     60

atcacctgca agtccagtca gagtctttta gctagtggca accaaaataa ctacttggcc    120

tggcaccaac agaaaccagg aaaagctccg aaaatgctga ttatttgggc atccactagg    180

gtatctggag tcccttctcg cttctctgga tccgggtctg ggacggattt cactctgacc    240

atcagcagtc tgcagccgga agacttcgca acttattact gtcagcagtc ctacagcgct    300

ccgctcacgt tcggacaggg taccaaggtg gagatcaaac gtacggtggc tgcaccatct    360

gtcttcatct tcccgccatc tgatgagcag ttgaaatctg gaactgcctc tgttgtgtgc    420

ctgctgaata acttctatcc cagagaggcc aaagtacagt ggaaggtgga taacgccctc    480

caatcgggta actcccagga gagtgtcaca gagcaggaca gcaaggacag cacctacagc    540

ctcagcagca ccctgacgct gagcaaagca gactacgaga aacacaaagt ctacgcctgc    600

gaagtcaccc atcagggcct gagctcgccc gtcacaaaga gcttcaacag gggagagtgt    660

tgactcgag                                                            669
```

<210> SEQ ID NO 54
<211> LENGTH: 23

<212> TYPE: PRT
<213> ORGANISM: Artificial Sequence
<220> FEATURE:
<223> OTHER INFORMATION: Synthetic linker between VH and VL

<400> SEQUENCE: 54

```
Gly Leu Gly Gly Leu Gly Gly Gly Gly Ser Gly Gly Gly Gly Ser Gly
  1               5                  10                  15

Gly Ser Ser Gly Val Gly Ser
             20
```

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of huAbF46 antibody

<400> SEQUENCE: 55

```
gctagcgttt tagcagaagt tcaattggtt gaatctggtg gtggtttggt tcaaccaggt     60

ggttctttga gattgtcttg tgctgcttct ggttttactt tcaccgatta ttacatgtcc    120

tgggttagac aagctccagg taaaggtttg gaatggttgg gtttcattag aaacaaggct    180

aacggttaca ctaccgaata ttctgcttct gttaagggta gattcaccat ttctagagac    240

aactctaaga acaccttgta cttgcaaatg aactccttga gagctgaaga tactgctgtt    300

tattactgcg ctagagataa ttggtttgct tattggggtc aaggtacttt ggttactgtt    360

tcttctggcc tcgggggcct cggaggagga ggtagtggcg gaggaggctc cggtggatcc    420

agcggtgtgg gttccgatat tcaaatgacc caatctccat cttctttgtc tgcttcagtt    480

ggtgatagag ttaccattac ttgtaagtcc tcccaatctt tgttggcttc tggtaatcag    540

aacaattact tggcttggca tcaacaaaaa ccaggtaaag ctccaaagat gttgattatt    600

tgggcttcta ccagagtttc tggtgttcca tctagatttt ctggttctgg ttccggtact    660

gattttactt tgaccatttc atccttgcaa ccagaagatt tcgctactta ctactgtcaa    720

caatcttact ctgctccatt gacttttggt caaggtacaa aggtcgaaat caagagagaa    780

ttcggtaagc ctatccctaa ccctctcctc ggtctcgatt ctacgggtgg tggtggatct    840

ggtggtggtg gttctggtgg tggtggttct caggaactga caactatatg cgagcaaatc    900

ccctcaccaa ctttagaatc gacgccgtac tctttgtcaa cgactactat tttggccaac    960

gggaaggcaa tgcaaggagt ttttgaatat tacaaatcag taacgtttgt cagtaattgc   1020

ggttctcacc cctcaacaac tagcaaaggc agccccataa acacacagta tgtttttttga   1080

gtttaaac                                                            1088
```

<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:

<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt 60
cctcgtcttc accggtcgcg ttcctgaaac gcagatgtgc ctcgcgccgc actgctccga 120
acaataaaga ttctacaata ctagctttta tggttatgaa gaggaaaaat tggcagtaac 180
ctggccccac aaaccttcaa atgaacgaat caaattaaca accataggat gataatgcga 240
ttagtttttt agccttattt ctggggtaat taatcagcga agcgatgatt tttgatctat 300
taacagatat ataaatgcaa aaactgcata accactttaa ctaatacttt caacattttc 360
ggtttgtatt acttcttatt caaatgtaat aaaagtatca acaaaaaatt gttaatatac 420
ctctatactt taacgtcaag gagaaaaaac cccggatcgg actactagca gctgtaatac 480
gactcactat agggaatatt aagctaattc tacttcatac attttcaatt aagatgcagt 540
tacttcgctg tttttcaata ttttctgtta ttgctagcgt tttagcagaa gttcaattgg 600
ttgaatctgg tggtggtttg gttcaaccag gtggttcttt gagattgtct tgtgctgctt 660
ctggttttac tttcaccgat tattacatgt cctgggttag acaagctcca ggtaaaggtt 720
tggaatggtt gggtttcatt agaaacaagg ctaacggtta cactaccgaa tattctgctt 780
ctgttaaggg tagattcacc atttctagag acaactctaa gaacaccttg tacttgcaaa 840
tgaactcctt gagagctgaa gatactgctg tttattactg cgctagagat aattggtttg 900
cttattgggg tcaaggtact ttggttactg tttcttctgg cctcgggggc ctcggaggag 960
gaggtagtgg cggaggaggc tccggtggat ccagcggtgt gggttccgat attcaaatga 1020
cccaatctcc atcttctttg tctgcttcag ttggtgatag agttaccatt acttgtaagt 1080
cctcccaatc tttgttggct tctggtaatc agaacaatta cttggcttgg catcaacaaa 1140
aaccaggtaa agctccaaag atgttgatta tttgggcttc taccagagtt tctggtgttc 1200
catctagatt ttctggttct ggttccggta ctgattttac tttgaccatt tcatccttgc 1260
aaccagaaga tttcgctact tactactgtc aacaatctta ctctgctcca ttgacttttg 1320
gtcaaggtac aaaggtcgaa atcaagagag aattcggtaa gcctatccct aaccctctcc 1380

-continued

```
tcggtctcga ttctacgggt ggtggtggat ctggtggtgg tggttctggt ggtggtggtt   1440
ctcaggaact gacaactata tgcgagcaaa tcccctcacc aactttagaa tcgacgccgt   1500
actctttgtc aacgactact attttggcca acgggaaggc aatgcaagga gtttttgaat   1560
attacaaatc agtaacgttt gtcagtaatt gcggttctca cccctcaaca actagcaaag   1620
gcagccccat aaacacacag tatgtttttt gagtttaaac ccgctgatct gataacaaca   1680
gtgtagatgt aacaaaatcg actttgttcc cactgtactt ttagctcgta caaaatacaa   1740
tatacttttc atttctccgt aaacaacatg ttttcccatg taatatcctt ttctattttt   1800
cgttccgtta ccaactttac acatacttta tatagctatt cacttctata cactaaaaaa   1860
ctaagacaat tttaattttg ctgcctgcca tatttcaatt tgttataaat tcctataatt   1920
tatcctatta gtagctaaaa aaagatgaat gtgaatcgaa tcctaagaga attgggcaag   1980
tgcacaaaca atacttaaat aaatactact cagtaataac ctatttctta gcatttttga   2040
cgaaatttgc tattttgtta gagtctttta caccatttgt ctccacacct ccgcttacat   2100
caacaccaat aacgccattt aatctaagcg catcaccaac attttctggc gtcagtccac   2160
cagctaacat aaaatgtaag ctctcggggc tctcttgcct tccaacccag tcagaaatcg   2220
agttccaatc caaaagttca cctgtcccac ctgcttctga atcaaacaag ggaataaacg   2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa aacatcctcc ttaggttgat   2460
tacgaaacac gccaaccaag tatttcggag tgcctgaact atttttatat gcttttacaa   2520
gacttgaaat tttccttgca ataaccgggt caattgttct ctttctattg ggcacacata   2580
taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctcctttt ctttttttcga ccgaatttct tgaagacgaa agggcctcgt   2820
gatacgccta tttttatagg ttaatgtcat gataataatg gtttcttagg acggatcgct   2880
tgcctgtaac ttacacgcgc ctcgtatctt ttaatgatgg aataatttgg gaatttactc   2940
tgtgtttatt tatttttatg ttttgtattt ggattttaga aagtaaataa agaaggtaga   3000
agagttacgg aatgaagaaa aaaaaataaa caaaggttta aaaaatttca acaaaaagcg   3060
tactttacat atatatttat tagacaagaa aagcagatta aatagatata cattcgatta   3120
acgataagta aaatgtaaaa tcacaggatt ttcgtgtgtg gtcttctaca cagacaagat   3180
gaaacaattc ggcattaata cctgagagca ggaagagcaa gataaaaggt agtatttgtt   3240
ggcgatcccc ctagagtctt ttacatcttc ggaaaacaaa aactattttt tctttaattt   3300
cttttttttac tttctatttt taatttatat atttatatta aaaaatttaa attataatta   3360
tttttatagc acgtgatgaa aaggacccag gtggcacttt tcggggaaat gtgcgcggaa   3420
cccctatttg tttatttttc taaatacatt caaatatgta tccgctcatg agacaataac   3480
cctgataaat gcttcaataa tattgaaaaa ggaagagtat gagtattcaa catttccgtg   3540
tcgcccttat tccctttttt gcggcatttt gccttcctgt ttttgctcac ccagaaacgc   3600
tggtgaaagt aaaagatgct gaagatcagt tgggtgcacg agtgggttac atcgaactgg   3660
atctcaacag cggtaagatc cttgagagtt ttcgccccga agaacgtttt ccaatgatga   3720
```

-continued

```
gcacttttaa agttctgcta tgtggcgcgg tattatcccg tgttgacgcc gggcaagagc   3780

aactcggtcg ccgcatacac tattctcaga atgacttggt tgagtactca ccagtcacag   3840

aaaagcatct tacggatggc atgacagtaa gagaattatg cagtgctgcc ataaccatga   3900

gtgataacac tgcggccaac ttacttctga caacgatcgg aggaccgaag gagctaaccg   3960

ctttttttgca caacatgggg gatcatgtaa ctcgccttga tcgttgggaa ccggagctga   4020

atgaagccat accaaacgac gagcgtgaca ccacgatgcc tgtagcaatg gcaacaacgt   4080

tgcgcaaact attaactggc gaactactta ctctagcttc ccggcaacaa ttaatagact   4140

ggatggaggc ggataaagtt gcaggaccac ttctgcgctc ggcccttccg gctggctggt   4200

ttattgctga taaatctgga gccggtgagc gtgggtctcg cggtatcatt gcagcactgg   4260

ggccagatgg taagccctcc cgtatcgtag ttatctacac gacggggcagt caggcaacta   4320

tggatgaacg aaatagacag atcgctgaga taggtgcctc actgattaag cattggtaac   4380

tgtcagacca agtttactca tatatacttt agattgattt aaaacttcat ttttaattta   4440

aaaggatcta ggtgaagatc ctttttgata atctcatgac caaaatccct taacgtgagt   4500

tttcgttcca ctgagcgtca gaccccgtag aaaagatcaa aggatcttct tgagatcctt   4560

tttttctgcg cgtaatctgc tgcttgcaaa caaaaaaacc accgctacca gcggtggttt   4620

gtttgccgga tcaagagcta ccaactcttt ttccgaaggt aactggcttc agcagagcgc   4680

agataccaaa tactgtcctt ctagtgtagc cgtagttagg ccaccacttc aagaactctg   4740

tagcaccgcc tacatacctc gctctgctaa tcctgttacc agtggctgct gccagtggcg   4800

ataagtcgtg tcttaccggg ttggactcaa gacgatagtt accggataag gcgcagcggt   4860

cgggctgaac ggggggttcg tgcacacagc ccagcttgga gcgaacgacc tacaccgaac   4920

tgagatacct acagcgtgag cattgagaaa gcgccacgct tcccgaaggg agaaaggcgg   4980

acaggtatcc ggtaagcggc agggtcggaa caggagagcg cacgagggag cttccagggg   5040

ggaacgcctg gtatctttat agtcctgtcg ggtttcgcca cctctgactt gagcgtcgat   5100

ttttgtgatg ctcgtcaggg gggccgagcc tatggaaaaa cgccagcaac gcggcctttt   5160

tacggttcct ggccttttgc tggccttttg ctcacatgtt ctttcctgcg ttatcccctg   5220

attctgtgga taaccgtatt accgcctttg agtgagctga taccgctcgc cgcagccgaa   5280

cgaccgagcg cagcgagtca gtgagcgagg aagcggaaga gcgcccaata cgcaaaccgc   5340

ctctccccgc gcgttggccg attcattaat gcagctggca cgacaggttt cccgactgga   5400

aagcgggcag tgagcgcaac gcaattaatg tgagttacct cactcattag gcaccccagg   5460

ctttacactt tatgcttccg gctcctatgt tgtgtggaat tgtgagcgga taacaatttc   5520

acacaggaaa cagctatgac catgattacg ccaagctcgg aattaaccct cactaaaggg   5580

aacaaaagct ggctagt                                                  5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

```
Glu Pro Lys Ser Cys Asp Cys His Cys Pro Pro Cys Pro
  1               5                  10
```

<210> SEQ ID NO 58

<211> LENGTH: 435
<212> TYPE: DNA
<213> ORGANISM: Artificial Sequence
<220> FEATURE:
<223> OTHER INFORMATION: Synthetic polynucleotide encoding CDR-L3
derived from L3-1 clone

<400> SEQUENCE: 58
gaattcacta gtgattaatt cgccgccacc atggattcac aggcccaggt cctcatgttg 60
ctgctgctat cggtatctgg tacctgtgga gatatccaga tgacccagtc cccgagctcc 120
ctgtccgcct ctgtgggcga tagggtcacc atcacctgca agtccagtca gagtctttta 180
gctagtggca accaaaataa ctacttggcc tggcaccaac agaaaccagg aaaagctccg 240
aaaatgctga ttatttgggc atccactagg gtatctggag tcccttctcg cttctctgga 300
tccgggtctg ggacggattt cactctgacc atcagcagtc tgcagccgga agacttcgca 360
acttattact gtcagcagtc ctacagccgc ccgtacacgt tcggacaggg taccaaggtg 420
gagatcaaac gtacg 435

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
derived from L3-2 clone

<400> SEQUENCE: 59
gaattcacta gtgattaatt cgccgccacc atggattcac aggcccaggt cctcatgttg 60
ctgctgctat cggtatctgg tacctgtgga gatatccaga tgacccagtc cccgagctcc 120
ctgtccgcct ctgtgggcga tagggtcacc atcacctgca agtccagtca gagtctttta 180
gctagtggca accaaaataa ctacttggcc tggcaccaac agaaaccagg aaaagctccg 240
aaaatgctga ttatttgggc atccactagg gtatctggag tcccttctcg cttctctgga 300
tccgggtctg ggacggattt cactctgacc atcagcagtc tgcagccgga agacttcgca 360
acttattact gtgggcagtc ctacagccgt ccgctcacgt tcggacaggg taccaaggtg 420
gagatcaaac gtacg 435

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
derived from L3-3 clone

<400> SEQUENCE: 60
gaattcacta gtgattaatt cgccgccacc atggattcac aggcccaggt cctcatgttg 60
ctgctgctat cggtatctgg tacctgtgga gatatccaga tgacccagtc cccgagctcc 120
ctgtccgcct ctgtgggcga tagggtcacc atcacctgca agtccagtca gagtctttta 180
gctagtggca accaaaataa ctacttggcc tggcaccaac agaaaccagg aaaagctccg 240
aaaatgctga ttatttgggc atccactagg gtatctggag tcccttctcg cttctctgga 300
tccgggtctg ggacggattt cactctgacc atcagcagtc tgcagccgga agacttcgca 360
acttattact gtgcacagtc ctacagccat ccgttctctt tcggacaggg taccaaggtg 420
gagatcaaac gtacg 435

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
derived from L3-5 clone

<400> SEQUENCE: 61

```
gaattcacta gtgattaatt cgccgccacc atggattcac aggcccaggt cctcatgttg     60

ctgctgctat cggtatctgg tacctgtgga gatatccaga tgacccagtc cccgagctcc    120

ctgtccgcct ctgtgggcga tagggtcacc atcacctgca agtccagtca gagtctttta    180

gctagtggca accaaaataa ctacttggcc tggcaccaac agaaaccagg aaaagctccg    240

aaaatgctga ttatttgggc atccactagg gtatctggag tcccttctcg cttctctgga    300

tccgggtctg ggacggattt cactctgacc atcagcagtc tgcagccgga agacttcgca    360

acttattact gtcagcagtc ctacagccgc ccgtttacgt tcggacaggg taccaaggtg    420

gagatcaaac gtacg                                                     435
```

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
of huAbF46-H4-A1, U6-HC7 hinge and constant region of human IgG1

<400> SEQUENCE: 62

```
Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220
```

```
Asn Thr Lys Val Asp Lys Lys Val Glu Pro Lys Ser Cys Asp Cys His
225                 230                 235                 240

Cys Pro Pro Cys Pro Ala Pro Glu Leu Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460


<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63

gaattcgccg ccaccatgga atggagctgg gtttttctcg taacactttt aaatggtatc      60

cagtgtgagg ttcagctggt ggagtctggc ggtggcctgg tgcagccagg gggctcactc     120

cgtttgtcct gtgcagcttc tggcttcacc ttcactgatt actacatgag ctgggtgcgt     180

caggccccgg gtaagggcct ggaatggttg ggttttatta gaaacaaagc taatggttac     240

acaacagagt acagtgcatc tgtgaagggt cgtttcacta taagcagaga taattccaaa     300

aacacactgt acctgcagat gaacagcctg cgtgctgagg acactgccgt ctattattgt     360

gctagagata actggtttgc ttactggggc caagggactc tggtcaccgt ctcctcggct     420

agcaccaagg gcccatcggt cttcccctg gcaccctcct ccaagagcac ctctgggggc     480

acagcggccc tgggctgcct ggtcaaggac tacttccccg aaccggtgac ggtgtcgtgg     540

aactcaggcg ccctgaccag cggcgtgcac accttcccgg ctgtcctaca gtcctcagga     600

ctctactccc tcagcagcgt ggtgaccgtg ccctccagca gcttgggcac ccagacctac     660
```

-continued

```
atctgcaacg tgaatcacaa gcccagcaac accaaggtgg acaagaaagt tgagcccaaa    720

agctgcgatt gccactgtcc tccatgtcca gcacctgaac tcctgggggg accgtcagtc    780

ttcctcttcc ccccaaaacc caaggacacc ctcatgatct cccggacccc tgaggtcaca    840

tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140

aaccaggtca gcctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcta cagcaagctc accgtggaca agagcaggtg gcagcagggg   1320

aacgtcttct catgctccgt gatgcatgag gctctgcaca accactacac gcagaagagc   1380

ctctccctgt ctccgggtaa atgactcgag                                    1410
```

```
<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of human
      IgG1

<400> SEQUENCE: 64

Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
```

```
    210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460
```

```
<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG1

<400> SEQUENCE: 65

gaattcgccg ccaccatgga atggagctgg gtttttctcg taacactttt aaatggtatc     60

cagtgtgagg ttcagctggt ggagtctggc ggtggcctgg tgcagccagg gggctcactc    120

cgtttgtcct gtgcagcttc tggcttcacc ttcactgatt actacatgag ctgggtgcgt    180

caggccccgg gtaagggcct ggaatggttg ggttttatta gaaacaaagc taatggttac    240

acaacagagt acagtgcatc tgtgaagggt cgtttcacta taagcagaga taattccaaa    300

aacacactgt acctgcagat gaacagcctg cgtgctgagg acactgccgt ctattattgt    360

gctagagata actggtttgc ttactggggc caagggactc tggtcaccgt ctcctcggct    420

agcaccaagg gcccatcggt cttccccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600
```

-continued

```
ctctactccc tcagcagcgt ggtgaccgtg ccctccagca gcttgggcac ccagacctac    660

atctgcaacg tgaatcacaa gcccagcaac accaaggtgg acaagaaagt tgagaggaag    720

tgctgtgtgg agtgcccccc ctgcccagca cctgaactcc tggggggacc gtcagtcttc    780

ctcttccccc caaaacccaa ggacaccctc atgatctccc ggacccctga ggtcacatgc    840

gtggtggtgg acgtgagcca cgaagaccct gaggtcaagt tcaactggta cgtggacggc    900

gtggaggtgc ataatgccaa gacaaagccg cgggaggagc agtacaacag cacgtaccgt    960

gtggtcagcg tcctcaccgt cctgcaccag gactggctga atggcaagga gtacaagtgc   1020

aaggtctcca acaaagccct cccagccccc atcgagaaaa ccatctccaa agccaaaggg   1080

cagccccgag aaccacaggt gtacaccctg cccccatccc gggaggagat gaccaagaac   1140

caggtcagcc tgacctgcct ggtcaaaggc ttctatccca gcgacatcgc cgtggagtgg   1200

gagagcaatg ggcagccgga gaacaactac aagaccacgc ctcccgtgct ggactccgac   1260

ggctccttct tcctctacag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaatg actcgag                                       1407
```

```
<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of human
      IgG2

<400> SEQUENCE: 66

Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205
```

-continued

```
Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Gln Phe
        275                 280                 285

Asn Trp Tyr Val Asp Gly Val Glu Val His Asn Ala Lys Thr Lys Pro
    290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide consisting of heavy chain of huAbF46-H4-A1, human IgG2 hinge and constant region of human IgG2

<400> SEQUENCE: 67

```
gaattcgccg ccaccatgga atggagctgg gtttttctcg taacactttt aaatggtatc      60

cagtgtgagg ttcagctggt ggagtctggc ggtggcctgg tgcagccagg gggctcactc     120

cgtttgtcct gtgcagcttc tggcttcacc ttcactgatt actacatgag ctgggtgcgt     180

caggccccgg gtaagggcct ggaatggttg ggttttatta gaaacaaagc taatggttac     240

acaacagagt acagtgcatc tgtgaagggt cgtttcacta taagcagaga taattccaaa     300

aacacactgt acctgcagat gaacagcctg cgtgctgagg acactgccgt ctattattgt     360

gctagagata actggtttgc ttactggggc caagggactc tggtcaccgt ctcctcggct     420

agcaccaagg gcccatcggt cttccccctg gcgccctgct ccaggagcac ctccgagagc     480

acagcggccc tgggctgcct ggtcaaggac tacttccccg aaccggtgac ggtgtcgtgg     540

aactcaggcg ctctgaccag cggcgtgcac accttcccag ctgtcctaca gtcctcagga     600
```

ctctactccc tcagcagcgt ggtgaccgtg ccctccagca acttcggcac ccagacctac 660
acctgcaacg tagatcacaa gcccagcaac accaaggtgg acaagacagt tgagcgcaaa 720
tgttgtgtcg agtgcccacc gtgcccagca ccacctgtgg caggaccgtc agtcttcctc 780
ttccccccaa aacccaagga caccctcatg atctcccgga cccctgaggt cacgtgcgtg 840
gtggtggacg tgagccacga agaccccgag gtccagttca actggtacgt ggacggcgtg 900
gaggtgcata atgccaagac aaagccacgg gaggagcagt tcaacagcac gttccgtgtg 960
gtcagcgtcc tcaccgttgt gcaccaggac tggctgaacg gcaaggagta caagtgcaag 1020
gtctccaaca aaggcctccc agcccccatc gagaaaacca tctccaaaac caaagggcag 1080
ccccgagaac cacaggtgta caccctgccc ccatcccggg aggagatgac caagaaccag 1140
gtcagcctga cctgcctggt caaaggcttc taccccagcg acatcgccgt ggagtgggag 1200
agcaatgggc agccggagaa caactacaag accacgcctc ccatgctgga ctccgacggc 1260
tccttcttcc tctacagcaa gctcaccgtg gacaagagca ggtggcagca ggggaacgtc 1320
ttctcatgct ccgtgatgca tgaggctctg cacaaccact acacgcagaa gagcctctcc 1380
ctgtctccgg gtaaatgact cgag 1404

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain of huAbF46-H4-A1(H36Y) and human kappa constant region

<400> SEQUENCE: 68

Met Asp Ser Gln Ala Gln Val Leu Met Leu Leu Leu Leu Ser Val Ser
1 5 10 15

Gly Thr Cys Gly Asp Ile Gln Met Thr Gln Ser Pro Ser Ser Leu Ser
20 25 30

Ala Ser Val Gly Asp Arg Val Thr Ile Thr Cys Lys Ser Ser Gln Ser
35 40 45

Leu Leu Ala Ser Gly Asn Gln Asn Asn Tyr Leu Ala Trp Tyr Gln Gln
50 55 60

Lys Pro Gly Lys Ala Pro Lys Met Leu Ile Ile Trp Ala Ser Thr Arg
65 70 75 80

Val Ser Gly Val Pro Ser Arg Phe Ser Gly Ser Gly Ser Gly Thr Asp
85 90 95

Phe Thr Leu Thr Ile Ser Ser Leu Gln Pro Glu Asp Phe Ala Thr Tyr
100 105 110

Tyr Cys Gln Gln Ser Tyr Ser Arg Pro Tyr Thr Phe Gly Gln Gly Thr
115 120 125

Lys Val Glu Ile Lys Arg Thr Val Ala Ala Pro Ser Val Phe Ile Phe
130 135 140

Pro Pro Ser Asp Glu Gln Leu Lys Ser Gly Thr Ala Ser Val Val Cys
145 150 155 160

Leu Leu Asn Asn Phe Tyr Pro Arg Glu Ala Lys Val Gln Trp Lys Val
165 170 175

Asp Asn Ala Leu Gln Ser Gly Asn Ser Gln Glu Ser Val Thr Glu Gln
180 185 190

Asp Ser Lys Asp Ser Thr Tyr Ser Leu Ser Ser Thr Leu Thr Leu Ser
195 200 205

-continued

```
Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide consisting of light chain of huAbF46-H4-A1(H36Y) and human kappa constant region

<400> SEQUENCE: 69

```
aattcactag tgattaattc gccgccacca tggattcaca ggcccaggtc ctcatgttgc      60

tgctgctatc ggtatctggt acctgtggag atatccagat gacccagtcc ccgagctccc     120

tgtccgcctc tgtgggcgat agggtcacca tcacctgcaa gtccagtcag agtcttttag     180

ctagtggcaa ccaaaataac tacttggcct ggtaccaaca gaaaccagga aaagctccga     240

aaatgctgat tatttgggca tccactaggg tatctggagt cccttctcgc ttctctggat     300

ccgggtctgg gacggatttc actctgacca tcagcagtct gcagccggaa gacttcgcaa     360

cttattactg tcagcagtcc tacagccgcc cgtacacgtt cggacagggt accaaggtgg     420

agatcaaacg tacggtggct gcaccatctg tcttcatctt cccgccatct gatgagcagt     480

tgaaatctgg aactgcctct gttgtgtgcc tgctgaataa cttctatccc agagaggcca     540

aagtacagtg gaaggtggat aacgccctcc aatcgggtaa ctcccaggag agtgtcacag     600

agcaggacag caaggacagc acctacagcc tcagcagcac cctgacgctg agcaaagcag     660

actacgagaa acacaaagtc tacgcctgcg aagtcaccca tcagggcctg agctcgcccg     720

tcacaaagag cttcaacagg ggagagtgtt gactcgag                             758
```

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain of huAbF46-H4-A1 and human kappa constant region

<400> SEQUENCE: 70

```
Met Asp Ser Gln Ala Gln Val Leu Met Leu Leu Leu Leu Ser Val Ser
  1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Ser Gln Ser
         35                  40                  45

Leu Leu Ala Ser Gly Asn Gln Asn Asn Tyr Leu Ala Trp His Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
        115                 120                 125
```

-continued

```
Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
  1               5                  10                  15

Ser Ala Leu


<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
  1               5                  10


<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
  1               5


<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
      anti-c-Met antibody (AbF46 or huAbF46-H1)

<400> SEQUENCE: 74

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30
```

```
Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)

<400> SEQUENCE: 75

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg


<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
```

-continued

<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gtttttctcg taacactttt aaatggtatc 60
cagtgtgagg tgaagctggt ggagtctgga ggaggcttgg tacagcctgg gggttctctg 120
agactctcct gtgcaacttc tgggttcacc ttcactgatt actacatgag ctgggtccgc 180
cagcctccag gaaaggcact tgagtggttg ggttttatta gaaacaaagc taatggttac 240
acaacagagt acagtgcatc tgtgaagggt cggttcacca tctccagaga taattcccaa 300
agcatcctct atcttcaaat ggacaccctg agagctgagg acagtgccac ttattactgt 360
gcaagagata actggtttgc ttactggggc caagggactc tggtcactgt ctctgcagct 420
agcaccaagg gcccatcggt cttccccctg gcaccctcct ccaagagcac ctctgggggc 480
acagcggccc tgggctgcct ggtcaaggac tacttccccg aaccggtgac ggtgtcgtgg 540
aactcaggcg ccctgaccag cggcgtgcac accttcccgg ctgtcctaca gtcctcagga 600
ctctactccc tcagcagcgt ggtgaccgtg ccctccagca gcttgggcac ccagacctac 660
atctgcaacg tgaatcacaa gcccagcaac accaaggtgg acaagaaagt tgagcccaaa 720
tcttgtgaca aaactcacac atgcccaccg tgcccagcac ctgaactcct ggggggaccg 780
tcagtcttcc tcttcccccc aaaacccaag gacaccctca tgatctcccg gacccctgag 840
gtcacatgcg tggtggtgga cgtgagccac gaagaccctg aggtcaagtt caactggtac 900
gtggacggcg tggaggtgca taatgccaag acaaagccgc gggaggagca gtacaacagc 960
acgtaccgtg tggtcagcgt cctcaccgtc ctgcaccagg actggctgaa tggcaaggag 1020
tacaagtgca aggtctccaa caaagccctc ccagccccca tcgagaaaac catctccaaa 1080
gccaaagggc agccccgaga accacaggtg tacaccctgc ccccatcccg ggaggagatg 1140
accaagaacc aggtcagcct gacctgcctg gtcaaaggct tctatcccag cgacatcgcc 1200
gtggagtggg agagcaatgg gcagccggag aacaactaca agaccacgcc tcccgtgctg 1260
gactccgacg gctccttctt cctctacagc aagctcaccg tggacaagag caggtggcag 1320
caggggaacg tcttctcatg ctccgtgatg catgaggctc tgcacaacca ctacacgcag 1380
aagagcctct ccctgtctcc gggtaaatga ctcgag 1416

<210> SEQ ID NO 77
<211> LENGTH: 759
<212> TYPE: DNA
<213> ORGANISM: Artificial Sequence
<220> FEATURE:
<223> OTHER INFORMATION: Synthetic nucleotide sequence of light chain of anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)

<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atggattcac aggcccaggt cctcatgttg     60

ctgctgctat cggtatctgg tacctgtgga gacattttga tgacccagtc tccatcctcc    120

ctgactgtgt cagcaggaga gaaggtcact atgagctgca agtccagtca gagtctttta    180

gctagtggca accaaaataa ctacttggcc tggcaccagc agaaaccagg acgatctcct    240

aaaatgctga taatttgggc atccactagg gtatctggag tccctgatcg cttcataggc    300

agtggatctg ggacggattt cactctgacc atcaacagtg tgcaggctga agatctggct    360

gtttattact gtcagcagtc ctacagcgct ccgctcacgt tcggtgctgg gaccaagctg    420

gagctgaaac gtacggtggc tgcaccatct gtcttcatct tcccgccatc tgatgagcag    480

ttgaaatctg gaactgcctc tgttgtgtgc ctgctgaata acttctatcc cagagaggcc    540

aaagtacagt ggaaggtgga taacgccctc caatcgggta actcccagga gagtgtcaca    600

gagcaggaca gcaaggacag cacctacagc ctcagcagca ccctgacgct gagcaaagca    660

gactacgaga aacacaaagt ctacgcctgc gaagtcaccc atcagggcct gagctcgccc    720

gtcacaaaga gcttcaacag gggagagtgt tgactcgag                           759
```

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78

```
atgaaggccc ccgctgtgct tgcacctggc atcctcgtgc tcctgtttac cttggtgcag     60

aggagcaatg gggagtgtaa agaggcacta gcaaagtccg agatgaatgt gaatatgaag    120

tatcagcttc ccaacttcac cgcggaaaca cccatccaga atgtcattct acatgagcat    180

cacattttcc ttggtgccac taactacatt tatgttttaa atgaggaaga ccttcagaag    240

gttgctgagt acaagactgg gcctgtgctg gaacacccag attgtttccc atgtcaggac    300

tgcagcagca aagccaattt atcaggaggt gtttggaaag ataacatcaa catggctcta    360

gttgtcgaca cctactatga tgatcaactc attagctgtg gcagcgtcaa cagagggacc    420

tgccagcgac atgtctttcc ccacaatcat actgctgaca tacagtcgga ggttcactgc    480

atattctccc cacagataga agagcccagc cagtgtcctg actgtgtggt gagcgccctg    540

ggagccaaag tcctttcatc tgtaaaggac cggttcatca acttctttgt aggcaatacc    600

ataaattctt cttatttccc agatcatcca ttgcattcga tatcagtgag aaggctaaag    660

gaaacgaaag atggttttat gtttttgacg gaccagtcct acattgatgt ttacctgtag    720
```

-continued

```
ttcagagatt cttaccccat taagtatgtc catgcctttg aaagcaacaa ttttatttac    780
ttcttgacgg tccaaaggga aactctagat gctcagactt ttcacacaag aataatcagg    840
ttctgttcca taaactctgg attgcattcc tacatggaaa tgcctctgga gtgtattctc    900
acagaaaaga gaaaaaagag atccacaaag aaggaagtgt ttaatatact tcaggctgcg    960
tatgtcagca agcctggggc ccagcttgct agacaaatag gagccagcct gaatgatgac   1020
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcatttttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg ggacatggac tcaacagatc   1680
tgtctgcctg caatctacaa ggttttccca aatagtgcac cccttgaagg agggacaagg   1740
ctgaccatat gtggctggga ctttggattt cggaggaata ataaatttga tttaaagaaa   1800
actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg gaaaaacatg tactttaaaa   2100
agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg gagcacaata   2280
acaggtgttg ggaaaaacct gaattcagtt agtgtcccga gaatggtcat aaatgtgcat   2340
gaagcaggaa ggaactttac agtggcatgt caacatcgct ctaattcaga gataatctgt   2400
tgtaccactc cttccctgca acagctgaat ctgcaactcc ccctgaaaac caaagccttt   2460
ttcatgttag atgggatcct ttccaaatac tttgatctca tttatgtaca taatcctgtg   2520
tttaagcctt ttgaaaagcc agtgatgatc tcaatgggca atgaaaatgt actggaaatt   2580
aagggaaatg atattgaccc tgaagcagtt aaaggtgaag tgttaaaagt tggaaataag   2640
agctgtgaga atatacactt acattctgaa gccgttttat gcacggtccc caatgacctg   2700
ctgaaattga acagcgagct aaatatagag tggaagcaag caatttcttc aaccgtcctt   2760
ggaaaagtaa tagttcaacc agatcagaat ttcacaggat tgattgctgg tgttgtctca   2820
atatcaacag cactgttatt actacttggg tttttcctgt ggctgaaaaa gagaaagcaa   2880
attaaagatc tgggcagtga attagttcgc tacgatgcaa gagtacacac tcctcatttg   2940
gataggcttg taagtgcccg aagtgtaagc ccaactacag aaatggtttc aaatgaatct   3000
gtagactacc gagctacttt tccagaagat cagtttccta attcatctca gaacggttca   3060
```

```
tgccgacaag tgcagtatcc tctgacagac atgtccccca tcctaactag tggggactct   3120

gatatatcca gtccattact gcaaaatact gtccacattg acctcagtgc tctaaatcca   3180

gagctggtcc aggcagtgca gcatgtagtg attgggccca gtagcctgat tgtgcatttc   3240

aatgaagtca taggaagagg gcattttggt tgtgtatatc atgggacttt gttggacaat   3300

gatggcaaga aaattcactg tgctgtgaaa tccttgaaca gaatcactga cataggagaa   3360

gtttcccaat ttctgaccga gggaatcatc atgaaagatt ttagtcatcc caatgtcctc   3420

tcgctcctgg gaatctgcct gcgaagtgaa gggtctccgc tggtggtcct accatacatg   3480

aaacatggag atcttcgaaa tttcattcga aatgagactc ataatccaac tgtaaaagat   3540

cttattggct ttggtcttca agtagccaaa ggcatgaaat atcttgcaag caaaaagttt   3600

gtccacagag acttggctgc aagaaactgt atgctggatg aaaaattcac agtcaaggtt   3660

gctgattttg gtcttgccag agacatgtat gataaagaat actatagtgt acacaacaaa   3720

acaggtgcaa agctgccagt gaagtggatg gctttggaaa gtctgcaaac tcaaaagttt   3780

accaccaagt cagatgtgtg gtcctttggc gtgctcctct gggagctgat gacaagagga   3840

gccccacctt atcctgacgt aaacaccttt gatataactg tttacttgtt gcaagggaga   3900

agactcctac aacccgaata ctgcccagac cccttatatg aagtaatgct aaaatgctgg   3960

caccctaaag ccgaaatgcg cccatccttt tctgaactgg tgtcccggat atcagcgatc   4020

ttctctactt tcattgggga gcactatgtc catgtgaacg ctacttatgt gaacgtaaaa   4080

tgtgtcgctc cgtatccttc tctgttgtca tcagaagata acgctgatga tgaggtggac   4140

acacgaccag cctccttctg ggagacatca                                    4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
  1               5                  10                  15

Leu Asn Glu Glu Asp Leu Gln Lys Val Ala Glu Tyr Lys Thr Gly Pro
             20                  25                  30

Val Leu Glu His Pro Asp Cys Phe Pro Cys Gln Asp Cys Ser Ser Lys
         35                  40                  45

Ala Asn Leu Ser Gly Gly Val Trp Lys Asp Asn Ile Asn Met Ala Leu
     50                  55                  60

Val Val Asp Thr Tyr Tyr Asp Asp Gln Leu Ile Ser Cys Gly Ser Val
 65                  70                  75                  80

Asn Arg Gly Thr Cys Gln Arg His Val Phe Pro His Asn His Thr Ala
                 85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Phe Val Gly Asn Thr
    130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
```

-continued

```
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
    210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
    290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
    370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440


<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

Tyr Thr Leu Val Ile Thr Gly Lys Lys Ile Thr Lys Ile Pro Leu Asn
  1               5                  10                  15

Gly Leu Gly Cys Arg His Phe Gln Ser Cys Ser Gln Cys Leu Ser Ala
            20                  25                  30

Pro Pro Phe Val Gln Cys Gly Trp Cys His Asp Lys Cys Val Arg Ser
        35                  40                  45

Glu Glu Cys Leu Ser Gly Thr Trp Thr Gln Gln Ile Cys Leu Pro Ala
    50                  55                  60

Ile Tyr Lys Val Phe Pro Asn Ser Ala Pro Leu Glu Gly Gly Thr Arg
 65                  70                  75                  80

Leu Thr Ile Cys Gly Trp Asp Phe Gly Phe Arg Arg Asn Asn Lys Phe
```

-continued

```
                85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ile Ser Asn Gly His
    130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
    210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
    290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
    370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415

Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450
```

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

```
Val His Phe Asn Glu Val Ile Gly Arg Gly His Phe Gly Cys Val Tyr
  1               5                  10                  15

His Gly Thr Leu Leu Asp Asn Asp Gly Lys Lys Ile His Cys Ala Val
             20                  25                  30

Lys Ser Leu Asn Arg Ile Thr Asp Ile Gly Glu Val Ser Gln Phe Leu
         35                  40                  45

Thr Glu Gly Ile Ile Met Lys Asp Phe Ser His Pro Asn Val Leu Ser
     50                  55                  60

Leu Leu Gly Ile Cys Leu Arg Ser Glu Gly Ser Pro Leu Val Val Leu
 65                  70                  75                  80

Pro Tyr Met Lys His Gly Asp Leu Arg Asn Phe Ile Arg Asn Glu Thr
                 85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain of c-Met

<400> SEQUENCE: 82

```
ctacatgagc atcacatttt ccttggtgcc actaactaca tttatgtttt aaatgaggaa      60

gaccttcaga aggttgctga gtacaagact gggcctgtgc tggaacaccc agattgtttc     120

ccatgtcagg actgcagcag caaagccaat ttatcaggag gtgtttggaa agataacatc     180
```

```
aacatggctc tagttgtcga cacctactat gatgatcaac tcattagctg tggcagcgtc    240
aacagaggga cctgccagcg acatgtcttt ccccacaatc atactgctga catacagtcg    300
gaggttcact gcatattctc cccacagata gaagagccca gccagtgtcc tgactgtgtg    360
gtgagcgccc tgggagccaa agtcctttca tctgtaaagg accggttcat caacttcttt    420
gtaggcaata ccataaattc ttcttatttc ccagatcatc cattgcattc gatatcagtg    480
agaaggctaa aggaaacgaa agatggtttt atgtttttga cggaccagtc ctacattgat    540
gttttacctg agttcagaga ttcttacccc attaagtatg tccatgcctt tgaaagcaac    600
aattttattt acttcttgac ggtccaaagg gaaactctag atgctcagac ttttcacaca    660
agaataatca ggttctgttc cataaactct ggattgcatt cctacatgga aatgcctctg    720
gagtgtattc tcacagaaaa gagaaaaaag agatccacaa agaaggaagt gtttaatata    780
cttcaggctg cgtatgtcag caagcctggg gcccagcttg ctagacaaat aggagccagc    840
ctgaatgatg acattctttt cggggtgttc gcacaaagca agccagattc tgccgaacca    900
atggatcgat ctgccatgtg tgcattccct atcaaatatg tcaacgactt cttcaacaag    960
atcgtcaaca aaaacaatgt gagatgtctc cagcattttt acggacccaa tcatgagcac   1020
tgctttaata ggacacttct gagaaattca tcaggctgtg aagcgcgccg tgatgaatat   1080
cgaacagagt ttaccacagc tttgcagcgc gttgacttat tcatgggtca attcagcgaa   1140
gtcctcttaa catctatatc caccttcatt aaaggagacc tcaccatagc taatcttggg   1200
acatcagagg gtcgcttcat gcaggttgtg gtttctcgat caggaccatc aacccctcat   1260
gtgaattttc tcctggactc ccatccagtg tctccagaag tgattgtgga gcatacatta   1320
aaccaaaatg gc                                                       1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT
domain of c-Met

<400> SEQUENCE: 83

```
tacacactgg ttatcactgg gaagaagatc acgaagatcc cattgaatgg cttgggctgc     60
agacatttcc agtcctgcag tcaatgcctc tctgccccac cctttgttca gtgtggctgg    120
tgccacgaca aatgtgtgcg atcggaggaa tgcctgagcg ggacatggac tcaacagatc    180
tgtctgcctg caatctacaa ggttttccca aatagtgcac cccttgaagg agggacaagg    240
ctgaccatat gtggctggga ctttggattt cggaggaata ataaatttga tttaaagaaa    300
actagagttc tccttggaaa tgagagctgc accttgactt taagtgagag cacgatgaat    360
acattgaaat gcacagttgg tcctgccatg aataagcatt tcaatatgtc cataattatt    420
tcaaatggcc acgggacaac acaatacagt acattctcct atgtggatcc tgtaataaca    480
agtatttcgc cgaaatacgg tcctatggct ggtggcactt tacttacttt aactggaaat    540
tacctaaaca gtgggaattc tagacacatt tcaattggtg gaaaaacatg tactttaaaa    600
agtgtgtcaa acagtattct tgaatgttat accccagccc aaaccatttc aactgagttt    660
gctgttaaat tgaaaattga cttagccaac cgagagacaa gcatcttcag ttaccgtgaa    720
gatcccattg tctatgaaat tcatccaacc aaatctttta ttagtggtgg gagcacaata    780
acaggtgttg ggaaaaacct gaattcagtt agtgtcccga gaatggtcat aaatgtgcat    840
```

-continued

```
gaagcaggaa ggaactttac agtggcatgt caacatcgct ctaattcaga gataatctgt    900

tgtaccactc cttccctgca acagctgaat ctgcaactcc ccctgaaaac caaagccttt    960

ttcatgttag atgggatcct ttccaaatac tttgatctca tttatgtaca taatcctgtg   1020

tttaagcctt ttgaaaagcc agtgatgatc tcaatgggca atgaaaatgt actggaaatt   1080

aagggaaatg atattgaccc tgaagcagtt aaaggtgaag tgttaaaagt tggaaataag   1140

agctgtgaga atatacactt acattctgaa gccgttttat gcacggtccc caatgacctg   1200

ctgaaattga acagcgagct aaatatagag tggaagcaag caatttcttc aaccgtcctt   1260

ggaaaagtaa tagttcaacc agatcagaat ttcacagga                          1299
```

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain of c-Met

<400> SEQUENCE: 84

```
gtgcatttca atgaagtcat aggaagaggg cattttggtt gtgtatatca tgggactttg     60

ttggacaatg atggcaagaa aattcactgt gctgtgaaat ccttgaacag aatcactgac    120

ataggagaag tttcccaatt tctgaccgag ggaatcatca tgaaagattt tagtcatccc    180

aatgtcctct cgctcctggg aatctgcctg cgaagtgaag ggtctccgct ggtggtccta    240

ccatacatga aacatggaga tcttcgaaat ttcattcgaa atgagactca taatccaact    300

gtaaaagatc ttattggctt tggtcttcaa gtagccaaag gcatgaaata tcttgcaagc    360

aaaaagtttg tccacagaga cttggctgca agaaactgta tgctggatga aaaattcaca    420

gtcaaggttg ctgattttgg tcttgccaga gacatgtatg ataaagaata ctatagtgta    480

cacaacaaaa caggtgcaaa gctgccagtg aagtggatgg ctttggaaag tctgcaaact    540

caaaagttta ccaccaagtc agatgtgtgg tcctttggcg tgctcctctg ggagctgatg    600

acaagaggag ccccacctta tcctgacgta aacacctttg atataactgt ttacttgttg    660

caagggagaa gactcctaca acccgaatac tgcccagacc ccttatatga agtaatgcta    720

aaatgctggc accctaaagc cgaaatgcgc ccatcctttt ctgaactggt gtcccggata    780

tcagcgatct tctctacttt cattggggag cactatgtcc atgtgaacgc tacttatgtg    840

aacgtaaaat gtgtcgctcc gtatccttct ctgttgtcat cagaagataa cgctgatgat    900

gaggtggaca cacgaccagc ctccttctgg gagacatca                           939
```

<210> SEQ ID NO 85
<211> LENGTH: 13
<212> TYPE: PRT
<213> ORGANISM: Artificial Sequence
<220> FEATURE:
<223> OTHER INFORMATION: Synthetic heavy chain CDR3 of anti-c-Met antibody

<400> SEQUENCE: 85

```
Asp Asn Trp Phe Ala Tyr Trp Gly Gln Gly Thr Leu Val
  1               5                  10
```

<210> SEQ ID NO 86
<211> LENGTH: 10
<212> TYPE: PRT
<213> ORGANISM: Artificial Sequence
<220> FEATURE:

```
<223> OTHER INFORMATION: Synthetic light chain CDR3 of anti-c-Met
      antibody

<400> SEQUENCE: 86

Leu Thr Phe Gly Ala Gly Thr Lys Leu Glu
  1               5                  10


<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Ala Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Gln Ser Ile
 65                  70                  75                  80

Leu Tyr Leu Gln Met Asp Thr Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ala
        115


<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody

<400> SEQUENCE: 88

Asp Ile Leu Met Thr Gln Ser Pro Ser Ser Leu Thr Val Ser Ala Gly
  1               5                  10                  15

Glu Lys Val Thr Met Ser Cys Lys Ser Ser Gln Ser Leu Leu Ala Ser
             20                  25                  30

Gly Asn Gln Asn Asn Tyr Leu Ala Trp His Gln Gln Lys Pro Gly Arg
         35                  40                  45

Ser Pro Lys Met Leu Ile Ile Trp Ala Ser Thr Arg Val Ser Gly Val
     50                  55                  60

Pro Asp Arg Phe Ile Gly Ser Gly Ser Gly Thr Asp Phe Thr Leu Thr
 65                  70                  75                  80

Ile Asn Ser Val Gln Ala Glu Asp Leu Ala Val Tyr Tyr Cys Gln Gln
                 85                  90                  95

Ser Tyr Ser Ala Pro Leu Thr Phe Gly Ala Gly Thr Lys Leu Glu Leu
            100                 105                 110

Lys Arg


<210> SEQ ID NO 89
```

-continued

<211> LENGTH: 17
<212> TYPE: PRT
<213> ORGANISM: Artificial Sequence
<220> FEATURE:
<223> OTHER INFORMATION: Synthetic light chain CDR3 of anti-c-Met antibody

<400> SEQUENCE: 89

```
Gln Gln Ser Tyr Ser Ala Pro Leu Thr Phe Gly Ala Gly Thr Lys Leu
  1               5                  10                  15

Glu
```

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

```
Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115
```

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

```
Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110
```

```
Val Thr Val Ser Ser
        115


<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115


<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5
```

<400> SEQUENCE: 94

```
Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115
```

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti c-Met humanized antibody(huAbF46-H4)

<400> SEQUENCE: 95

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Ala Pro Leu Thr Phe Gly Gln Gly Thr Lys Val Glu Ile
            100                 105                 110

Lys Arg
```

<210> SEQ ID NO 96
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

```
Asp Ile Leu Met Thr Gln Ser Pro Ser Ser Leu Thr Ala Ser Val Gly
  1               5                  10                  15

Asp Arg Val Thr Met Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45
```

```
Ala Pro Lys Met Leu Ile Ile Trp Ala Ser Thr Arg Val Ser Gly Val
     50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys


<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
     50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys


<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
     50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys
```

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

```
Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys
```

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

```
Glu Pro Ser Cys Asp Lys His Cys Cys Pro Pro Cys Pro
  1               5                  10
```

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

```
Glu Pro Lys Ser Cys Asp Cys His Cys Pro Pro Cys Pro
  1               5                  10
```

<210> SEQ ID NO 102
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

```
Glu Arg Lys Cys Cys Val Glu Cys Pro Pro Cys Pro
  1               5                  10
```

<210> SEQ ID NO 103
<211> LENGTH: 14
<212> TYPE: PRT
<213> ORGANISM: Artificial Sequence
<220> FEATURE:

<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
1 5 10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
1 5 10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
1 5 10 15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Asn Tyr Leu
1 5 10 15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain variable region of antibody L3-11Y

<400> SEQUENCE: 107

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Ala Trp
20 25 30

Gly Asn Gln Asn Asn Tyr Leu Ala Trp Tyr Gln Gln Lys Pro Gly Lys
35 40 45

Ala Pro Lys Met Leu Ile Ile Trp Ala Ser Thr Arg Val Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Tyr Cys Gln Gln
85 90 95

Ser Tyr Ser Arg Pro Tyr Thr Phe Gly Gln Gly Thr Lys Val Glu Ile
100 105 110

```
Lys Arg


<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Trp
            20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 109
<211> LENGTH: 5
<212> TYPE: PRT
<213> ORGANISM: Artificial Sequence
<220> FEATURE:
<223> OTHER INFORMATION: Synthetic CDR-H1 of anti-EGFR scFv

<400> SEQUENCE: 109

Asn Tyr Asp Met Ser
  1               5


<210> SEQ ID NO 110
<211> LENGTH: 17
<212> TYPE: PRT
<213> ORGANISM: Artificial Sequence
<220> FEATURE:
<223> OTHER INFORMATION: Synthetic CDR-H2 of anti-EGFR scFv

<400> SEQUENCE: 110
```

```
Gly Ile Ser His Ser Ser Gly Ser Lys Tyr Tyr Ala Asp Ser Val Lys
  1               5                   10                  15

Gly


<210> SEQ ID NO 111
<211> LENGTH: 13
<212> TYPE: PRT
<213> ORGANISM: Artificial Sequence
<220> FEATURE:
<223> OTHER INFORMATION: Synthetic CDR-H3 of anti-EGFR scFv

<400> SEQUENCE: 111

Lys Asp Ala Thr Pro Arg Pro Leu Lys Pro Phe Asp Tyr
  1               5                   10


<210> SEQ ID NO 112
<211> LENGTH: 13
<212> TYPE: PRT
<213> ORGANISM: Artificial Sequence
<220> FEATURE:
<223> OTHER INFORMATION: Synthetic CDR-L1 of anti-EGFR scFv

<400> SEQUENCE: 112

Thr Gly Ser Ser Ser Asn Ile Gly Asn Asn Asp Val Ser
  1               5                   10


<210> SEQ ID NO 113
<211> LENGTH: 7
<212> TYPE: PRT
<213> ORGANISM: Artificial Sequence
<220> FEATURE:
<223> OTHER INFORMATION: Synthetic CDR-L2 of anti-EGFR scFv

<400> SEQUENCE: 113

Asp Asp Asn Lys Arg Pro Ser
  1               5


<210> SEQ ID NO 114
<211> LENGTH: 9
<212> TYPE: PRT
<213> ORGANISM: Artificial Sequence
<220> FEATURE:
<223> OTHER INFORMATION: Synthetic CDR-L3 of anti-EGFR scFv

<400> SEQUENCE: 114

Gly Ser Trp Asp Ala Ser Leu Asn Ala
  1               5


<210> SEQ ID NO 115
<211> LENGTH: 121
<212> TYPE: PRT
<213> ORGANISM: Artificial Sequence
<220> FEATURE:
<223> OTHER INFORMATION: Synthetic Heavy chain variable region of
      anti-EGFR scFv

<400> SEQUENCE: 115

Glu Val Gln Leu Leu Glu Ser Gly Gly Gly Leu Val Gln Pro Gly Gly
  1               5                   10                  15

Ser Leu Arg Leu Ser Cys Ala Ala Ser Gly Phe Thr Phe Ser Asn Tyr
             20                  25                  30

Asp Met Ser Trp Val Arg Gln Ala Pro Gly Lys Gly Leu Glu Trp Val
         35                  40                  45

Ser Gly Ile Ser His Ser Ser Gly Ser Lys Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Thr Pro Arg Pro Leu Lys Pro Phe Asp Tyr Trp Gly
            100                 105                 110

Gln Gly Thr Leu Val Thr Val Ser Ser
        115                 120


<210> SEQ ID NO 116
<211> LENGTH: 111
<212> TYPE: PRT
<213> ORGANISM: Artificial Sequence
<220> FEATURE:
<223> OTHER INFORMATION: Synthetic Light chain variable region of
      anti-EGFR scFv

<400> SEQUENCE: 116

Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Asn Asn
            20                  25                  30

Asp Val Ser Trp Tyr Gln Gln Leu Pro Gly Thr Ala Pro Lys Leu Leu
        35                  40                  45

Ile Tyr Asp Asp Asn Lys Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ala Ser Leu
                 85                  90                  95

Asn Ala Tyr Val Phe Gly Gly Gly Thr Lys Leu Thr Val Leu Gly
            100                 105                 110


<210> SEQ ID NO 117
<211> LENGTH: 121
<212> TYPE: PRT
<213> ORGANISM: Artificial Sequence
<220> FEATURE:
<223> OTHER INFORMATION: Synthetic heavy chain variable region of
      anti-EGFR antibody (modified)

<400> SEQUENCE: 117

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Cys Leu Glu Trp Val
        35                  40                  45

Ser Gly Ile Ser His Ser Ser Gly Ser Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ala Thr Pro Arg Pro Leu Lys Pro Phe Asp Tyr Trp Gly
            100                 105                 110

Gln Gly Thr Leu Val Thr Val Ser Ser
        115                 120
```

<210> SEQ ID NO 118
<211> LENGTH: 111
<212> TYPE: PRT
<213> ORGANISM: Artificial Sequence
<220> FEATURE:
<223> OTHER INFORMATION: Synthetic light chain variable region of
anti-EGFR antibody (modified)

<400> SEQUENCE: 118

```
Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Asn Asn
             20                  25                  30

Asp Val Ser Trp Tyr Gln Gln Leu Pro Gly Thr Ala Pro Lys Leu Leu
         35                  40                  45

Ile Tyr Asp Asp Asn Lys Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Ala Ser Leu
                 85                  90                  95

Asn Ala Tyr Val Phe Gly Cys Gly Thr Lys Leu Thr Val Leu Gly
            100                 105                 110
```

<210> SEQ ID NO 119
<211> LENGTH: 363
<212> TYPE: DNA
<213> ORGANISM: Artificial Sequence
<220> FEATURE:
<223> OTHER INFORMATION: Synthetic coding nucleotide sequence of heavy
chain variable region of anti-EGFR antibody

<400> SEQUENCE: 119

```
gaggtgcagc tgttggagtc tgggggaggc ttggtacagc ctggggggtc cctgagactc     60

tcctgtgcag cctctggatt cacctttagc aattatgata tgagctgggt ccgccaggct    120

ccagggaagg ggctggagtg ggtctcaggg atctctcata gtagtggtag taaatattac    180

gctgattctg taaaaggtcg gttcaccatc tccagagaca attccaagaa cacgctgtat    240

ctgcaaatga acagcctgag agccgaggac acggccgtgt attactgtgc gaaagatgct    300

actccgcgtc cgctgaagcc tttcgactac tggggccagg gtacactggt caccgtgagc    360

tca                                                                  363
```

<210> SEQ ID NO 120
<211> LENGTH: 333
<212> TYPE: DNA
<213> ORGANISM: Artificial Sequence
<220> FEATURE:
<223> OTHER INFORMATION: Synthetic coding nucleotide sequence of light
chain variable region of anti-EGFR antibody

<400> SEQUENCE: 120

```
cagtctgtgc tgactcagcc accctcagcg tctgggaccc ccgggcagag ggtcaccatc     60

tcttgtactg gctcttcatc taatattggc aataatgatg tctcctggta ccagcagctc    120

ccaggaacgg cccccaaact cctcatctat gatgataata agcggccaag cggggtccct    180

gaccgattct ctggctccaa atctggcacc tcagcctccc tggccatcag tgggctccgg    240

tccgaggatg aggctgatta ttactgtggt tcttgggatg ctagcctgaa tgcttatgtc    300
```

```
ttcggcggag gcaccaagct gacggtccta ggc                              333


<210> SEQ ID NO 121
<211> LENGTH: 120
<212> TYPE: PRT
<213> ORGANISM: Artificial Sequence
<220> FEATURE:
<223> OTHER INFORMATION: Synthetic heavy-chain variable region of
      anti-EGFR antibody

<400> SEQUENCE: 121

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120


<210> SEQ ID NO 122
<211> LENGTH: 360
<212> TYPE: DNA
<213> ORGANISM: Artificial Sequence
<220> FEATURE:
<223> OTHER INFORMATION: Synthetic DNA encoding heavy-chain variable
      region of anti-EGFR antibody

<400> SEQUENCE: 122

caggtgcagc tggtgcagtc tggggctgag gtgaagaagc ctgggtcctc ggtgaaggtc      60

tcctgcaagg cctctggttt cacattcact gactacaaga tacactgggt gcgacaggcc     120

cctggacaag ggctcgagtg gatgggatat ttcaacccta acagcggtta tagtacctac     180

gcacagaagt tccagggcag ggtcaccatt accgcggaca aatccacgag cacagcctac     240

atggagctga gcagcctgag atctgaggac acggccgtgt attactgtgc gagactatcc     300

ccaggcggtt actatgttat ggatgcctgg ggccaaggga ccaccgtgac cgtctcctca     360


<210> SEQ ID NO 123
<211> LENGTH: 108
<212> TYPE: PRT
<213> ORGANISM: Artificial Sequence
<220> FEATURE:
<223> OTHER INFORMATION: Synthetic light-chain variable region of
      anti-EGFR antibody

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45
```

```
Tyr Asn Thr Asn Asn Leu Gln Thr Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Phe Pro Thr
                 85                  90                  95

Phe Gly Gln Gly Thr Lys Leu Glu Ile Lys Arg Thr
            100                 105


<210> SEQ ID NO 124
<211> LENGTH: 324
<212> TYPE: DNA
<213> ORGANISM: Artificial Sequence
<220> FEATURE:
<223> OTHER INFORMATION: Synthetic DNA encoding light-chain variable
      region of anti-EGFR antibody

<400> SEQUENCE: 124

gatatccaga tgacccagtc tccatcctcc ctgtctgcat ctgtcggaga ccgggtcacc     60

atcacctgcc gggcaagtca gggcattaac aattacttaa attggtacca gcagaagcca    120

gggaaagccc ctaagcgcct gatctataat accaacaact tgcagacagg cgtcccatca    180

aggttcagcg gcagtggatc cgggacagaa ttcactctca ccatcagcag cctgcagcct    240

gaagattttg ccacctatta ctgcttgcag cataatagtt ttcccacgtt tggccagggc    300

accaagctcg agatcaagcg tacg                                           324


<210> SEQ ID NO 125
<211> LENGTH: 120
<212> TYPE: PRT
<213> ORGANISM: Artificial Sequence
<220> FEATURE:
<223> OTHER INFORMATION: Synthetic modified heavy-chain variable region
      of anti-EGFR antibody

<400> SEQUENCE: 125

Gln Val Gln Leu Val Gln Ser Gly Ala Glu Val Lys Lys Pro Gly Ser
  1               5                  10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Cys Leu Glu Trp Met
        35                  40                  45

Gly Tyr Ile Asn Pro Asn Ser Gly Tyr Ser Thr Tyr Ala Ser Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120


<210> SEQ ID NO 126
<211> LENGTH: 108
<212> TYPE: PRT
<213> ORGANISM: Artificial Sequence
<220> FEATURE:
<223> OTHER INFORMATION: Synthetic modified light-chain variable region
      of anti-EGFR antibody
```

<400> SEQUENCE: 126

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Asn Asn Tyr
20 25 30

Leu Asn Trp Tyr Gln Gln Lys Pro Gly Lys Ala Pro Lys Leu Leu Ile
35 40 45

Tyr Asn Thr Asn Asn Leu Gln Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Glu Ala Thr Tyr Tyr Cys Leu Gln His Asn Ser Phe Pro Thr
85 90 95

Phe Gly Gln Cys Thr Lys Leu Glu Ile Lys Arg Thr
100 105

<210> SEQ ID NO 127
<211> LENGTH: 153
<212> TYPE: PRT
<213> ORGANISM: Artificial Sequence
<220> FEATURE:
<223> OTHER INFORMATION: Synthetic anti-EGFR DARPin-01

<400> SEQUENCE: 127

Asp Leu Gly Lys Lys Leu Leu Glu Ala Ala Arg Ala Gly Gln Asp Asp
1 5 10 15

Glu Val Arg Ile Leu Met Ala Asn Gly Ala Asp Val Asn Ala Asp Asp
20 25 30

Thr Trp Gly Trp Thr Pro Leu His Leu Ala Ala Tyr Gln Gly His Leu
35 40 45

Glu Ile Val Glu Val Leu Leu Lys Asn Gly Ala Asp Val Asn Ala Tyr
50 55 60

Asp Tyr Ile Gly Trp Thr Pro Leu His Leu Ala Ala Asp Gly His Leu
65 70 75 80

Glu Ile Val Glu Val Leu Leu Lys Asn Gly Ala Asp Val Asn Ala Ser
85 90 95

Asp Tyr Ile Gly Asp Thr Pro Leu His Leu Ala Ala His Asn Gly His
100 105 110

Leu Glu Ile Val Glu Val Leu Leu Lys His Gly Ala Asp Val Asn Ala
115 120 125

Gln Asp Lys Phe Gly Lys Thr Ala Phe Asp Ile Ser Ile Asp Asn Gly
130 135 140

Asn Glu Asp Leu Ala Glu Ile Leu Gln
145 150

<210> SEQ ID NO 128
<211> LENGTH: 154
<212> TYPE: PRT
<213> ORGANISM: Artificial Sequence
<220> FEATURE:
<223> OTHER INFORMATION: Synthetic Anti-EGFR DARPin-67

<400> SEQUENCE: 128

Asp Leu Gly Lys Lys Leu Leu Glu Ala Ala Arg Ala Gly Gln Asp Asp
1 5 10 15

Glu Val Arg Ile Leu Met Ala Asn Gly Ala Asp Val Asn Ala Thr Asp
20 25 30

Asn Asp Gly Asn Thr Pro Leu His Leu Ser Ala Trp Ile Gly His Leu
35 40 45

Glu Ile Val Glu Val Leu Leu Lys His Gly Ala Asp Val Asn Ala Asp
50 55 60

Asp Leu Leu Gly Met Thr Pro Leu His Leu Ala Ala Asp Thr Gly His
65 70 75 80

Leu Glu Ile Val Glu Val Leu Leu Lys Tyr Gly Ala Asp Val Asn Ala
85 90 95

Arg Asp Thr Arg Gly Lys Thr Pro Leu His Leu Ala Ala Arg Asp Gly
100 105 110

His Leu Glu Ile Val Glu Val Leu Leu Lys His Asp Ala Asp Val Asn
115 120 125

Ala Gln Asp Lys Phe Gly Lys Thr Ala Phe Asp Ile Ser Ile Asp Asn
130 135 140

Gly Asn Glu Asp Leu Ala Glu Ile Leu Gln
145 150

<210> SEQ ID NO 129
<211> LENGTH: 154
<212> TYPE: PRT
<213> ORGANISM: Artificial Sequence
<220> FEATURE:
<223> OTHER INFORMATION: Synthetic Anti-EGFR DARPin-68

<400> SEQUENCE: 129

Asp Leu Gly Lys Lys Leu Leu Glu Ala Ala Arg Ala Gly Gln Asp Asp
1 5 10 15

Glu Val Arg Ile Leu Met Ala Asn Gly Ala Asp Val Asn Ala Phe Asp
20 25 30

Tyr Trp Gly Met Thr Pro Leu His Leu Ala Ala Asp Asn Gly His Leu
35 40 45

Glu Ile Val Glu Val Leu Leu Lys His Gly Ala Asp Val Asn Ala Ser
50 55 60

Asp Asn Phe Gly Phe Thr Pro Leu His Leu Ala Ala Phe Tyr Gly His
65 70 75 80

Leu Glu Ile Val Glu Val Leu Leu Lys His Gly Ala Asp Val Asn Ala
85 90 95

Phe Asp Met Trp Gly Asn Thr Pro Leu His Leu Ala Ala Gln Asn Gly
100 105 110

His Leu Glu Ile Val Glu Val Leu Leu Lys Asn Gly Ala Asp Val Asn
115 120 125

Ala Gln Asp Lys Phe Gly Lys Thr Ala Phe Asp Ile Ser Ile Asp Asn
130 135 140

Gly Asn Glu Asp Leu Ala Glu Ile Leu Gln
145 150

<210> SEQ ID NO 130
<211> LENGTH: 187
<212> TYPE: PRT
<213> ORGANISM: Artificial Sequence
<220> FEATURE:
<223> OTHER INFORMATION: Synthetic Anti-EGFR DARPin-69

<400> SEQUENCE: 130

Asp Leu Gly Lys Lys Leu Leu Glu Ala Ala Arg Ala Gly Gln Asp Asp
1 5 10 15

Glu Val Arg Ile Leu Met Ala Asn Gly Ala Asp Val Asn Ala Asp Asp
20 25 30

-continued

Asn Ala Gly Arg Thr Pro Leu His Leu Ala Ala Asn Phe Gly His Leu
35 40 45

Glu Ile Val Glu Val Leu Leu Lys Asn Gly Ala Asp Val Asn Ala Lys
50 55 60

Gly His His Cys Asn Thr Pro Leu His Leu Ala Ala Trp Ala Gly His
65 70 75 80

Leu Glu Ile Val Glu Val Leu Leu Lys Tyr Gly Ala Asp Val Asn Ala
85 90 95

Asp Asp Asp Glu Gly Tyr Thr Pro Leu His Leu Ala Ala Asp Ile Gly
100 105 110

Asp Leu Glu Ile Val Glu Val Leu Leu Lys Tyr Gly Ala Asp Val Asn
115 120 125

Ala Trp Asp Met Tyr Gly Arg Thr Pro Leu His Leu Ala Ala Ser Ala
130 135 140

Gly His Leu Glu Ile Val Glu Val Leu Leu Lys Tyr Gly Ala Asp Val
145 150 155 160

Asn Ala Gln Asp Lys Phe Gly Lys Thr Ala Phe Asp Ile Ser Ile Asp
165 170 175

Asn Gly Asn Glu Asp Leu Ala Glu Ile Leu Gln
180 185

<210> SEQ ID NO 131
<211> LENGTH: 114
<212> TYPE: PRT
<213> ORGANISM: Artificial Sequence
<220> FEATURE:
<223> OTHER INFORMATION: Synthetic light chain variable region of anti c-Met antibody

<400> SEQUENCE: 131

Asp Ile Gln Met Thr Gln Ser Pro Ser Ser Leu Ser Ala Ser Val Gly
1 5 10 15

Asp Arg Val Thr Ile Thr Cys Lys Ser Ser Gln Ser Leu Leu Ala Ser
20 25 30

Gly Asn Gln Asn Asn Tyr Leu Ala Trp Tyr Gln Gln Lys Pro Gly Lys
35 40 45

Ala Pro Lys Met Leu Ile Ile Trp Ala Ser Thr Arg Val Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Tyr Cys Gln Gln
85 90 95

Ser Tyr Ser Arg Pro Tyr Thr Phe Gly Gln Gly Thr Lys Val Glu Ile
100 105 110

Lys Arg

<210> SEQ ID NO 132
<211> LENGTH: 50
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(10)
<223> OTHER INFORMATION: may be present or absent
<220> FEATURE:
<221> NAME/KEY: misc_feature
<222> LOCATION: (11)..(15)
<223> OTHER INFORMATION: may be present or absent -continued

```
<220> FEATURE:
<221> NAME/KEY: misc_feature
<222> LOCATION: (16)..(20)
<223> OTHER INFORMATION: may be present or absent
<220> FEATURE:
<221> NAME/KEY: misc_feature
<222> LOCATION: (21)..(25)
<223> OTHER INFORMATION: may be present or absent
<220> FEATURE:
<221> NAME/KEY: misc_feature
<222> LOCATION: (26)..(30)
<223> OTHER INFORMATION: may be present or absent
<220> FEATURE:
<221> NAME/KEY: misc_feature
<222> LOCATION: (31)..(35)
<223> OTHER INFORMATION: may be present or absent
<220> FEATURE:
<221> NAME/KEY: misc_feature
<222> LOCATION: (36)..(40)
<223> OTHER INFORMATION: may be present or absent
<220> FEATURE:
<221> NAME/KEY: misc_feature
<222> LOCATION: (41)..(45)
<223> OTHER INFORMATION: may be present or absent
<220> FEATURE:
<221> NAME/KEY: misc_feature
<222> LOCATION: (46)..(50)
<223> OTHER INFORMATION: may be present or absent

<400> SEQUENCE: 132

Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
                20                  25                  30

Gly Gly Gly Gly Ser Gly Gly Gly Gly Ser Gly Gly Gly Gly Ser
                35                  40                  45

Gly Gly Gly Gly Ser
                50


<210> SEQ ID NO 133
<211> LENGTH: 10
<212> TYPE: PRT
<213> ORGANISM: Artificial Sequence
<220> FEATURE:
<223> OTHER INFORMATION: Synthetic

<400> SEQUENCE: 133

Gly Gly Gly Gly Ser Gly Gly Gly Gly Ser
                5                   10
```

COMBINATION THERAPY USING DUAL INHIBITOR OF C-MET AND EGFR AND IGF-1R INHIBITOR

CROSS-REFERENCE TO RELATED APPLICATIONS

This application claims the benefit of Korean Patent Application No. 10-2014-0163791 filed on Nov. 21, 2014 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 152,884 byte ASCII (Text) file named "722073_ST25-Revised.TXT," created Jul. 6, 2017.

BACKGROUND OF THE INVENTION

1. Field

Provided is a method of preventing and/or treating a cancer, the method including co-administering a dual inhibitor of c-Met and EGFR (hereinafter, 'c-Met/EGFR dual inhibitor') and an IGF-1R inhibitor to a subject in need thereof and a method for using IGF-1R as a marker for resistance to a c-Met/EGFR dual inhibitor.

2. Description of the Related Art

It has been shown that resistance to a drug having a specific target is more common compared to resistance to a drug having multiple targets. In addition, it is known that the indications on which a targeting drug has a therapeutic effect when it is treated alone are limited. Therefore, co-administration of two or more targeting drugs can maximize the therapeutic effect in a subject by overcoming resistance caused by exclusive treatment with only one of the targeting drugs, and by can exhibiting a therapeutic effect for an indication in which one of the targeting drugs has no therapeutic effect. Such co-administration is expected to contribute to extending the scope of indications to be treated by target drugs and to overcoming resistance thereto.

Therefore, for more effective treatment of a disease, there remains a need to develop effective combination therapy targeting two or more targets.

BRIEF SUMMARY OF THE INVENTION

An embodiment provides a combination therapy targeting c-Met, EGFR, and IGF-1R.

Another embodiment provides a pharmaceutical composition for combination therapy for treating and/or preventing cancer, the composition including a c-Met/EGFR dual inhibitor and an IGF-1R inhibitor, as active ingredients.

Another embodiment provides a kit for treating and/or preventing cancer, including a first pharmaceutical composition including a c-Met/EGFR dual inhibitor, a second pharmaceutical composition including an IGF-1R inhibitor, and a package container.

Another embodiment provides a method of treating and/or preventing cancer, the method including co-administering a c-Met/EGFR dual inhibitor and an IGF-1R inhibitor to a subject in need thereof.

Another embodiment provides a pharmaceutical composition for overcoming resistance to a c-Met/EGFR dual inhibitor, the composition including an IGF-1R inhibitor.

Another embodiment provides a method of overcoming resistance to a c-Met/EGFR dual inhibitor, the method including administering an IGF-1R inhibitor together with a c-Met/EGFR dual inhibitor to a subject who has resistance to the c-Met/EGFR dual inhibitor.

Another embodiment provides a marker for predicting and/or examining (monitoring) an effect of a c-Met/EGFR dual inhibitor, including IGF-1R protein and/or nucleic acids (e.g., full-length DNA, cDNA or mRNA) encoding IGF-1R. The marker may be used for determining the presence or absence of resistance to a c-Met/EGFR dual inhibitor.

Another embodiment provides a method for predicting and/or examining (monitoring) an effect of a c-Met/EGFR dual inhibitor, including measuring a level of IGF-1R protein and/or nucleic acids (e.g., full-length DNA, cDNA or mRNA) encoding IGF-1R in a biological sample obtained from a subject. The method may be used for determining the presence or absence of resistance to a c-Met/EGFR dual inhibitor.

DETAILED DESCRIPTION OF THE INVENTION

Figure 1:
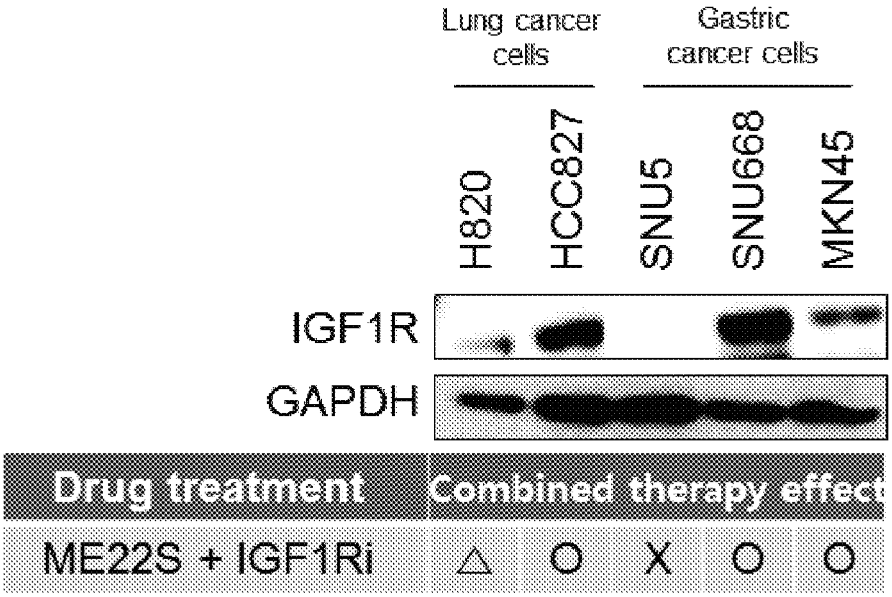
FIG. 1 provides western blotting results showing levels of IGF-1R protein in lung cancer cell lines H820 and HCC827 and gastric cancer cell lines SNU5, SNU668, and MKN45, indicating a correlation between level of IGF-1R protein and efficacy of combined administration of an anti-c-Met/anti-EGFR bispecific antibody and linsitinib (an IGF-1R inhibitor; indicated as "IGF1Ri").

A c-Met/EGFR dual inhibitor, such as an anti-c-Met/anti-EGFR bispecific antibody, generally exhibits strong anticancer effects on cancers having a high expression level of c-Met, such as gastric cancer, lung cancer, and the like. However, when resistance to an anti-c-Met/anti-EGFR bispecific antibody is inherently present in a subject (e.g., a c-Met and/or EGFR resistant cancer cell) or acquired by repeated administration of the anti-c-Met/anti-EGFR bispecific antibody, the anti-c-Met/anti-EGFR bispecific antibody cannot exhibit its effect on the subject, even if the expression level of c-Met in the subject is high. In cells with a high level of c-Met expression which are resistant to an anti-c-Met/anti-EGFR bispecific antibody (e.g., does not exhibit its anticancer effect), the expression level of IGF-1R is considerably higher compared to cells on which an anti-c-Met/anti-EGFR bispecific antibody exhibits its effect (e.g., anticancer effect). Based thereon, IGF-1R can serve as a marker for determining the presence or absence of resistance to an anti-c-Met/anti-EGFR bispecific antibody and/or as a target for a drug for being co-administered together with an anti-c-Met/anti-EGFR bispecific antibody in a combination therapy.

By co-administering an anti-c-Met/anti-EGFR bispecific antibody and an IGFR1 inhibitor to simultaneously inhibit c-Met, EGFR, and IGF-1R, an anticancer effect can be achieved even in cases where such effect cannot be obtained when only one or two of the targets is inhibited. Thus, the applicable scope of an anti-c-Met/anti-EGFR bispecific antibody can be expanded and resistance to an anti-c-Met/anti-EGFR bispecific antibody can be overcome.

In addition, when a c-Met/EGFR dual inhibitor and an IGFR1 inhibitor are co-administered simultaneously inhibiting c-Met, EGFR, and IGF-1R, the total overall dose of inhibitor can be decreased compared to co-administering a c-Met inhibitor, an EGFR inhibitor, and an IGFR1 inhibitor, thereby achieving both convenience in administration and decreased side effects such as cytotoxicity to normal cells caused by administration of three inhibitors.

For example, cancer cells in which an anti-c-Met/anti-EGFR bispecific antibody, a c-Met inhibitor, and/or an EGFR inhibitor do not exhibit an effect (e.g., an anticancer effect), an anticancer effect can be achieved by co-administration with an IGF-1R inhibitor. Such co-administration of a c-Met/EGFR dual inhibitor and an IGF-1R inhibitor overcomes an innate (inherent) or acquired resistance to a c-Met/EGFR dual inhibitor, thereby expanding the scope of symptoms and/or diseases to which a c-Met/EGFR dual inhibitor can be applicable.

Herein, the term "co-administration" and "combined administration" may be used interchangeably (i.e., have the same meaning).

The "c-Met" or "c-Met proteins" refer to receptor tyrosine kinases that bind to hepatocyte growth factors (HGF). The c-Met proteins may be those derived from all kinds of species, particularly a mammal, for example, those derived from a primate such as human c-Met (e.g. NP_000236.2), monkey c-Met (e.g., *Macaca mulatta*, NP_001162100), and the like, or those derived from a rodent such as mouse c-Met (e.g., NP_032617.2), rat c-Met (e.g., NP_113705.1), and the like. These proteins may include, for example, polypeptides encoded by the nucleotide sequence identified as GenBank Accession Number NM_000245.2, or proteins encoded by the polypeptide sequence identified as GenBank Accession Number NM_000236.2, or extracellular domains thereof. The receptor tyrosine kinase c-Met is involved in several mechanisms including cancer incidence, cancer metastasis, cancer cell migration, cancer cell penetration, angiogenesis, etc.

The "EGFR (epidermal growth factor receptor)" is a member of the receptor tyrosine kinases (RTKs) of HER family. The binding of a ligand to the extracellular domain of EGFR induces receptor homo- or hetero dimerization with other ErbB receptors, which in turn results in intracellular self-phosphorylation of specific tyrosine residues. EGFR self-phosphorylation leads to downstream signal transduction networks including MAPK and PI3K/Akt activation which affects cell proliferation, angiogenesis and metastasis. Over-expression, gene amplification, mutation, or rearrangement of EGFR are frequently observed in several human malignant tumors and are related to poor prognosis of cancer treatment and bad clinical outcomes. The EGFR or HER2 may be derived (obtained) from mammals, for example, primates such as humans and monkeys, or rodents such as rats and mice. For instance, the EGFR may be polypeptides encoded by the nucleotide sequences (mRNA or cDNA) deposited under GenBank Accession Nos. JQ739160, JQ739161, JQ739162, JQ739163, JQ739164, JQ739165, JQ739166, JQ739167, NM_005228.3, NM_201284.1, NM_201282.1, or NM_201283.1.

IGF-1R (insulin-like growth factor 1 receptor) binds to IGF1 (insulin-like growth factor 1) or IGF2 (insulin-like growth factor 2), and binds to insulin at a low affinity. The binding of IGF1 and IGF-1R increases the activity of receptor tyrosine kinases and induces auto-phosphorylation of the receptors or phosphorylation of internal related materials, thereby performing signal transduction. IGF-1R promotes proliferation of normal cells, but it can cause abnormal growth of cells. The overexpression of IGF-1R may cause formation of neoplasm, and thus its importance in cancer therapy emerged. The IGF-1R protein may be obtained from any species; for example, it may be at least one selected from the group consisting of human IGF-1R (e.g., AAI43722.1 (coding gene (cDNA or mRNA): BC143721.1), NP_000866.1 (coding gene (cDNA or mRNA): NM_000875.4), NP_001278787.1 (coding gene (cDNA or mRNA): NM_001291858.1)), etc.), mouse IGF-1R (e.g., AAI38870.1 (coding gene (cDNA or mRNA): BC138869.1), AAI38869.1 (coding gene (cDNA or mRNA): BC138868.1), NP_034643.2 (coding gene (cDNA or mRNA): NM_010513.2), etc.), and the like, but not be limited thereto.

It has been shown that IGF-1R signaling induces resistance to cytotoxic therapy and has a high relation with resistance to EGFR-targeting therapy. In particular, high expression of IGF-1R from cancer cells surgically excised from a gastric cancer patient is related to poor results of cancer therapy. In 86 gastric cancer patients having the surgical operation, the survival time is relatively longer for patients with low expression levels of IGF-1R and EGFR in the excised gastric cancer tissue compared to patients with high expression levels of IGF-1R and EGFR. Therefore, IGF-1R is considered as one of the important targets contributing to cancer cell growth through cross-talk with other RTKs.

As used herein, the term “c-Met/EGFR dual inhibitor” may refer to any agent (e.g., a compound or composition) capable of inhibiting activity and/or expression of c-Met and EGFR simultaneously, or blocking c-Met- and EGFR-signaling simultaneously by inhibiting ligands thereof, thereby preventing, improving, alleviating, reducing, and/or treating a c-Met- and/or EGFR-associated disease (e.g., a disease associating with abnormal activation and/or overexpression of c-Met and/or EGFR, such as cancer) or its symptoms. In addition, the c-Met/EGFR dual inhibitor may refer to any substance capable of recognizing and/or binding to c-Met and EGFR simultaneously to degrade and/or inhibit the functions or expression thereof. For example, the c-Met/EGFR dual inhibitor may be an anti-c-Met/anti-EGFR bispecific antibody which recognizes and/or binds to c-Met and EGFR at the same time. The anti-c-Met/anti-EGFR bispecific antibody may bind to both c-Met and EGFR and induce degradation of c-Met and/or EGFR.

As used herein, the term “effect of the c-Met/EGFR dual inhibitor” may refer to an effect to prevent, improve, alleviate, reduce, and/or treat a c-Met- and/or EGFR-associated disease, such as a cancer. For example, the effect of the c-Met/EGFR dual inhibitor may refer to an effect of reducing (or inhibiting proliferation of) cancer cells or cancer tissues, killing cancer cells or cancer tissues, and/or inhibiting invasion and/or migration of cancer cells related to metastasis. In other words, the effect may refer to an anticancer effect such as inhibiting of cancer cell proliferation, migration (metastasis), or invasion, or inducing cancer cell apoptosis, etc.

The present disclosure suggests a combination therapy by combined administration of a c-Met/EGFR dual inhibitor and an IGF-1R inhibitor, having advantages to expand the scope of application of the c-Met/EGFR dual inhibitor to indications (diseases) on which the c-Met/EGFR dual inhibitor does not exhibit an effect when used alone, and overcome resistance to the c-Met/EGFR dual inhibitor or the IGF-1R inhibitor. Of course, due to such effect to overcome resistance to the c-Met/EGFR dual inhibitor and a synergistic effect of the c-Met/EGFR dual inhibitor and the IGF-1R inhibitor, the combined administration of the c-Met/EGFR dual inhibitor and the IGF-1R inhibitor leads to more effective therapeutic effect on a disease on which the c-Met/EGFR dual inhibitor or IGF-1R inhibitor exhibits the effect even when each of them is used alone, and/or a disease having no resistance either to a c-Met/EGFR dual inhibitor nor to IGF-1R inhibitor. Therefore, by such combined administration, the dose of each inhibitor can be reduced and/or the administration interval can be increase (i.e., the frequency of administration can be decreased), thereby reducing side effects in a subject to be administered with the inhibitors.

One embodiment provides a pharmaceutical composition for combination therapy for preventing and/or treating of a cancer, comprising or consisting essentially of a c-Met/EGFR dual inhibitor and an IGF-1R inhibitor as active ingredients.

The pharmaceutical composition for combination therapy may be a mixed formulation (e.g., a single composition comprising two active ingredients) of a c-Met/EGFR dual inhibitor and an IGF-1R inhibitor. The IGF-1R inhibitor and c-Met/EGFR dual inhibitor may be included in any amount that is pharmaceutically effective when used together. The composition thus formulated can be used for simultaneous administration of the two active ingredients.

Alternatively, each of the c-Met/EGFR dual inhibitor and the IGF-1R inhibitor can be formulated in a separate composition and the two active ingredients (or compositions) can be separately administered simultaneously or sequentially. For instance, a first pharmaceutical composition including a pharmaceutically effective amount of the IGF-1R inhibitor as an active ingredient and a second pharmaceutical composition including a pharmaceutically effective amount of the c-Met/EGFR dual inhibitor as an active ingredient can be administered simultaneously or sequentially. In the case of the sequential administration, any order of administration may be used.

Another embodiment provides a kit useful for preventing and/or treating a cancer, comprising or consisting essentially of a first pharmaceutical composition including an IGF-1R inhibitor as an active ingredient, a second pharmaceutical composition including a c-Met/EGFR dual inhibitor as an active ingredient, and a package container. The IGF-1R inhibitor and c-Met/EGFR dual inhibitor may be used in amounts that are pharmaceutically effective when combined. The pharmaceutically effective amount of each inhibitor may be determined by the skilled medical practitioner or medical researcher. The package container can be any container that holds or otherwise links the two compositions in individual containers together in a single unit (e.g., a box that holds both containers, or plastic wrap that binds both containers together), or the package container may be a single, divided container having at least two chambers that each hold one of the two compositions.

A method of combination therapy for preventing and/or treating a cancer also is provided. The method comprises or consists essentially of co-administering a c-Met/EGFR dual inhibitor and an IGF-1R inhibitor to a subject in need of the prevention and/or treatment of cancer. The IGF-1R inhibitor and c-Met/EGFR dual inhibitor may be administered in amounts that are pharmaceutically effective when combined. The pharmaceutically effective amount of each inhibitor may be determined by the skilled medical practitioner or medical researcher. The method may further include, prior to the co-administration step, a step of identifying a subject in need of the prevention and/or treatment of cancer. The step of identifying may be conducted by any manner and/or method known to the relevant field for identifying whether or not a subject needs the prevention and/or treatment of cancer. For example, the step of identifying may include diagnosing a subject with cancer or identifying a subject who is diagnosed as a cancer subject, particularly a cancer associated with c-Met/EGFR expression.

Co-administration may be conducted by administering the two active ingredients (i.e., c-Met/EGFR dual inhibitor and IGF-1R inhibitor) simultaneously; for example, by administering a mixed formulation (e.g., single composition) of a c-Met/EGFR dual inhibitor and an IGF-1R inhibitor, as described herein. Alternatively, the c-Met/EGFR dual inhibitor and IGF-1R inhibitor can be administered separately. The co-administration may be conducted by a first step of administering a c-Met/EGFR dual inhibitor, and a second step of administering an IGF-1R inhibitor, wherein the first and the second administration steps may be conducted simultaneously or sequentially. In case of the sequential administration, the first step and the second step may be performed in any order. In the sequential administration the first step and the second step may be separated by any suitable time interval (e.g., about 1 second to about 24 hours, about 1 second to about 12 hours, or about 1 second to about 60 minutes (e.g., about 1 second to about 10 minutes); or 1-60 seconds, 1-60 minutes, 1-24 hours, or 1-7 days, 1-14 days, 7-14 days, 1-30 days, or so on). The c-Met/EGFR dual inhibitor and IGF-1R inhibitor may be administered in amounts that are pharmaceutically effective when combined, which the amount may be determined by the skilled medical practitioner or medical researcher.

The term "the pharmaceutically effective amount" as used in this specification refers to an amount of which each active ingredient can exert pharmaceutically significant effects (e.g., an amount sufficient to prevent or treat cancer in a subject).

The subject for administration may be any animal, for example a mammal including a primate such as a human or a monkey, or a rodent such as a mouse or a rat, or a cell or tissue separated therefrom, or a culture of the cell or tissue. In particular, the subject may be a mammal including a primate such as a human or a monkey, or a rodent such as a mouse or a rat, or a cell or tissue separated therefrom, or a culture of the cell or tissue, who has an innate resistance or acquired resistance to a c-Met/EGFR dual inhibitor by inducing repeated administration.

By combined administration of a c-Met/EGFR dual inhibitor and an IGF-1R inhibitor, a synergistic therapeutic effect can be achieved compared to administration of c-Met inhibitor or IGF-1R inhibitor alone. Furthermore, such synergistic therapeutic effect can be obtained for diseases (e.g., a cancer) in which each of the inhibitors does not exhibit its effect or which has resistance to each of the inhibitors.

The IGF-1R inhibitor may refer to any drug capable of targeting and/or inhibiting the IGF-1R protein and/or nucleic acids (e.g., full-length DNA, cDNA or mRNA) encoding IGF-1R. In particular, the IGF-1R inhibitor may be at least one selected from the group consisting of a compound (small molecule compound or its pharmaceutically acceptable salt), a protein, a nucleic acid and the like, which target and/or inhibit the IGF-1R protein and/or nucleic acids (e.g., full-length DNA, cDNA or mRNA) encoding IGF-1R (e.g., an antibody, an aptamer, siRNA, shRNA, microRNA). For example, the IGF-1R inhibitor may be at least one selected from the group consisting of linsitinib (OSI-906; 3-[8-Amino-1-(2-phenyl-7-quinolyl)imidazo[1,5-a]pyrazin-3-yl]-1-methyl-cyclobutanol), NVP-AEW541 (CAS#475489-16-8; 7-((1s,3s)-3-(azetidin-1-ylmethyl)cyclobutyl)-5-(3-(benzyloxy)phenyl)-7H-pyrrolo[2,3-d]pyrimidin-4-amine), GSK1904529A (CAS#1089283-49-7; N-(2,6-difluorophenyl)-5-(3-(2-(5-ethyl-2-methoxy-4-(4-(4-(methylsulfonyl)piperazin-1-yl)piperidin-1-yl)phenylamino)pyrimidin-4-yl)H-imidazo[1,2-a]pyridin-2-yl)-2-methoxybenzamide), NVP-ADW742 (CAS#475488-23-4; 5-(3-(benzyloxy)phenyl)-7-((1r,3r)-3-(pyrrolidin-1-ylmethyl)cyclobutyl)-7H-pyrrolo[2,3-d]pyrimidin-4-amine), BMS-536924 (CAS#468740-43-4; 4-[[(2S)-2-(3-chlorophenyl)-2-hydroxyethyl]amino]-3-[4-methyl-6-(4-morpholinyl)-1H-benzimidazol-2-yl]-2(1H)-pyridinone), figitumumab (CP-751,871), cixutumumab (IMC-A12), dalotuzumab (MK-0646), R1507 (fully human anti-IGF-1R antibody), XL-228 (CAS#898280-07-4), INSM-18 (nordihydroguaiaretic acid; NDGA; 4,4'-((2R,3S)-2,3-dimethylbutane-1,4-diyl)bis(benzene-1,2-diol)), BMS-754807 ((S)-1-(4-((5-cyclopropyl-1H-pyrazol-3-yl)amino)pyrrolo[2,1-f][1,2,4]triazin-2-yl)-N-(6-fluoropyridin-3-yl)-2-methylpyrrolidine-2-carboxamide), AG-1024 (Tyrphostin; CAS#65678-07-1; 2-(3-bromo-5-tert-butyl-4-hydroxybenzylidene)malononitrile), GSK1838705A (CAS#1116235-97-2; 2-(2-(1-(2-(dimethylamino)acetyl)-5-methoxyindolin-6-ylamino)-7H-pyrrolo[2,3-d]pyrimidin-4-ylamino)-6-fluoro-N-methylbenzamide), PQ 401 (CAS#196868-63-0; N-(5-Chloro-2-methoxyphenyl)-N'-(2-methyl-4-quinolinyl)urea), and pharmaceutically acceptable salts thereof, but not limited thereto.

XL-228:

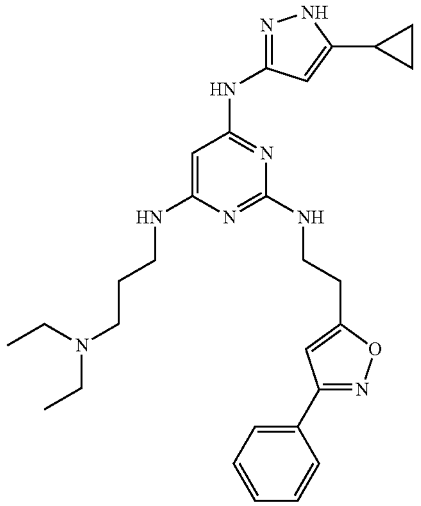

or

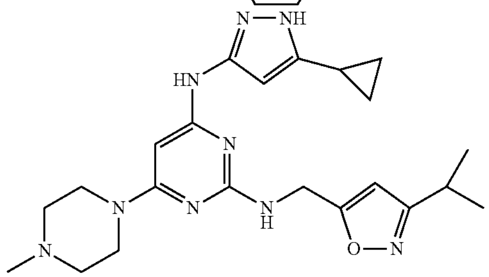

The c-Met/EGFR dual inhibitor may be any drug comprising an EGFR binding domain and a c-Met binding domain, thereby simultaneously recognizing and/or binding to EGFR and c-Met. For example, the c-Met/EGFR dual inhibitor nay be an anti-c-Met/anti-EGFR bispecific antibody comprising or consisting essentially of i) an anti-EGFR antibody or an antigen-binding fragment thereof, and ii) an anti-c-Met antibody or an antigen-binding fragment thereof. The antigen-binding fragment of anti-EGFR antibody or anti-c-Met antibody may be scFv, (scFv)2, scFv-Fc (scFv and Fc are fused to each other), Fab, Fab', or F(ab')2. Alternatively, the c-Met/EGFR dual inhibitor may comprise or consist essentially of i) an antibody mimetic protein specifically binding to EGFR (e.g., an anti-EGFR DARPin (designed ankyrin repeat protein)), and ii) an anti-c-Met antibody or an antigen-binding fragment thereof.

The anti-EGFR antibody or an antigen-binding fragment thereof may comprise or consist essentially of, at least one heavy chain complementarity determining region (CDR) selected from the group consisting of CDR-H1 including the amino acid sequence of SEQ ID NO: 109, CDR-H2 including the amino acid sequence of SEQ ID NO: 110, and CDR-H3 including the amino acid sequence of SEQ ID NO: 111 or a heavy chain variable region including the at least one heavy chain complementarity determining region;

at least one light chain complementarity determining region selected from the group consisting of CDR-L1 including the amino acid sequence of SEQ ID NO: 112, CDR-L2 including the amino acid sequence of SEQ ID NO: 113, and CDR-L3 including the amino acid sequence of SEQ ID NO: 114 or a light chain variable region including the at least one light chain complementarity determining region;

a combination of the at least one heavy chain complementarity determining region and the at least one light chain complementarity determining region; or a combination of the heavy chain variable region and the light chain variable region.

TABLE 1

| | Heavy chain CDR | | Light chain CDR |
|---|---|---|---|
| CDR-H1 | NYDMS (SEQ ID NO: 109) | CDR-L1 | TGSSSNIGNNDVS (SEQ ID NO: 112) |
| CDR-H2 | GISHSSGSKYYADSVKG (SEQ ID NO: 110) | CDR-L2 | DDNKRPS (SEQ ID NO: 113) |
| CDR-H3 | KDATPRPLKPFDY (SEQ ID NO: 111) | CDR-L3 | GSWDASLNA (SEQ ID NO: 114) |

For example, the anti-EGFR antibody or an antigen-binding fragment thereof may comprise or consist essentially of a heavy chain variable region including the amino acid sequence of SEQ ID NO: 115 or SEQ ID NO: 117, a light chain variable region including the amino acid sequence of SEQ ID NO: 116 or SEQ ID NO: 118, or a combination thereof.

In a particular embodiment, the anti-EGFR antibody or an antigen-binding fragment thereof may be an anti-EGFR scFv including a heavy chain variable region including the amino acid sequence of SEQ ID NO: 115 or SEQ ID NO: 117, and a light chain variable region including the amino acid sequence of SEQ ID NO: 116 or SEQ ID NO: 118.

<SEQ ID NO: 115: a heavy chain variable region of an anti-EGFR antibody>
EVQLLESGGGLVQPGGSLRLSCAASGFTFSNYDMSWVRQAPGKGLE

WVSGISHSSGSKYYADSVKGRFTISRDNSKNTLYLQMNSLRAEDTA

VYYCAKDATPRPLKPFDYWGQGTLVTVSS (wherein the sequences marked in bold type indicate CDRs, i.e., CDR-H1, CDR-H2, and CDR-H3, in sequence)

<SEQ ID NO: 116: a light chain variable region of an anti-EGFR antibody>
QSVLTQPPSASGTPGQRVTISCTGSSSNIGNNDVSWYQQLPGTAPK

LLIYDDNKRPSGVPDRFSGSKSGTSASLAISGLRSEDEADYYCGSW

DASLNAYVFGGGTKLTVLG (wherein the sequences marked in bold type indicate CDRs, i.e., CDR-L1, CDR-L2, and CDR-L3, in sequence)

<SEQ ID NO: 117: a heavy chain variable region of an anti-EGFR antibody>
EVQLLESGGGLVQPGGSLRLSCAASGFTFSNYDMSWVRQAPGKCLE

WVSGISHSSGSKYYADSVKGRFTISRDNSKNTLYLQMNSLRAEDTA

VYYCAKDATPRPLKPFDYWGQGTLVTVSS (wherein the sequences marked in bold type indicate CDRs, i.e., CDR-H1, CDR-H2, and CDR-H3, in sequence)

<SEQ ID NO: 118: a light chain variable region of an anti-EGFR antibody>
QSVLTQPPSASGTPGQRVTISCTGSSSNIGNNDVSWYQQLPGTAPK

LLIYDDNKRPSGVPDRFSGSKSGTSASLAISGLRSEDEADYYCGSW

DASLNAYVFGCGTKLTVLG (wherein the sequences marked in bold type indicate CDRs, i.e., CDR-L1, CDR-L2, and CDR-L3, in sequence)

Alternatively, the anti-EGFR antibody or an antigen-binding fragment thereof may be at least one selected from the group consisting of cetuximab (Erbitux), panitumumab, an anti-EGFR antibody or an antigen-binding fragment thereof comprising a heavy chain variable region of SEQ ID NO: 121, a light chain variable region of SEQ ID NO: 123, or a combination thereof, and an anti-EGFR antibody or an antigen-binding fragment thereof comprising a heavy chain variable region of SEQ ID NO: 125, a light chain variable region of SEQ ID NO: 126, or a combination thereof.

Alternatively, the EGFR binding domain may be an anti-EGFR DARPin.

DARPin (designed ankyrin repeat protein) refers to an antibody mimetic protein having high specificity and high binding affinity to a target protein, which is prepared via genetic engineering. DARPin is originated from natural ankyrin protein, and has a structure comprising at least 2 ankyrin repeat motifs, for example, comprising at least 3, 4 or 5 ankyrin repeat motifs. The DARPin can have any suitable molecular weight depending on the number of repeat motifs. For example, the DARPins including 3, 4 or 5 ankyrin repeat motifs may have a molecular weight of about 10 kDa, about 14 kDa, or about 18 kDa, respectively. DARPin includes a core that provides structure and a target binding portion that resides outside of the core and binds to a target. The structural core includes a conserved amino acid sequence and the target binding portion includes an amino acid sequence that differs depending on the target. Due to similarity (such as target specificity) with an antibody, DARPin may be fused with an IgG antibody to prepare a novel type of bispecific antibody.

The DARPin may be one targeting EGFR, i.e., an anti-EGFR DARPin (or EGFR binding DARPin), which specifically binding to EGFR. The anti-EGFR DARPin may be any DARPin having DARPin's own unique structure and specifically binding to EGFR. For example, the anti-EGFR DARPin may be at least one selected from the group consisting of the following 4 anti-EGFR DARPins:

anti-EGFR DARPin-01 (SEQ ID NO: 127):
dlgkklleaaragqddevrilmangadvnaddtwgwtplhlaayqg hleivevllkngadvnaydyigwtplhlaadghleivevllkngad vnasdyigdtplhlaahnghleivevllkhgadvnaqdkfgktafd isidngnedlaeilq anti-EGFR DARPin-67 (SEQ ID NO: 128):
dlgkklleaaragqddevrilmangadvnatdndgntplhlsawig hleivevllkhgadvnaddllgmtplhlaadtghleivevllkyga dvnardtrgktplhlaardghleivevllkhdadvnaqdkfgktaf disidngnedlaeilq anti-EGFR DARPin-68 (SEQ ID NO: 129):
dlgkklleaaragqddevrilmangadvnafdywgmtplhlaadng hleivevllkhgadvnasdnfgftplhlaafyghleivevllkhga dvnafdmwgntplhlaaqnghleivevllkngadvnaqdkfgktaf disidngnedlaeilq anti-EGFR DARPin-69 (SEQ ID NO: 130):
dlgkklleaaragqddevrilmangadvnaddnagrtplhlaanfg hleivevllkngadvnakghhcntplhlaawaghleivevllkyga -continued

```
dvnadddegytplhlaadigdleivevllkygadvnawdmygrtpl

hlaasaghleivevllkygadvnaqdkfgktafdisidngnedlae

ilq
```

The anti-EGFR DARPin may comprise about 1 to about 10, about 1 to about 5, or about 1 to about 3 of anti-EGFR DARPin units, wherein each of the DARPin units may be independently selected from SEQ ID NOs: 127 to 130. When the DARPin comprise about 2 or more DARPin units, each of the DARPin units may be the same with or different from each other.

When the EGFR binding domain is an antigen-binding fragment of an anti-EGFR antibody comprising a heavy chain variable region and a light chain variable region of an anti-EGFR antibody (e.g., an anti-EGFR scFv), or DARPin comprising 2 or more DARPin units, the heavy chain variable region and light chain variable region, or each DARPin unit may be linked to each other directly (i.e., with no linker) or via a linker. The linker may be a peptide linker, and if two or more linkers are used, the linkers may be the same with or different from each other. The peptide linker may include about 1 to about 100 or about 2 to about 50 (e.g., about 5 to about 25, about 1 to about 10, or about 2 to about 5) amino acids, and the kinds of the amino acids included in the peptide linker may not have any limitation. For example, the peptide linker may include Gly, Asn and/or Ser residues, or may include neutral amino acids such as Thr and/or Ala. Amino acid sequences suitable for a peptide linker may be well known in the relevant art. The length of the peptide linker may be properly determined so that there is no negative effect on the function of the bispecific chimeric protein. For example, the peptide linker may include at least one amino acid selected from the group consisting of Gly, Asn, Ser, Thr, and Ala, wherein the total number of the amino acids in the linker may be 1 to 100, 2 to 50, or 5 to 25. In one embodiment, the peptide linker may be represented as (GGGGS)n (SEQ ID NO: 132), wherein "n" is an integer from 1 to 10 (e.g., an integer from 2 to 5).

The anti-c-Met antibody or an antigen-binding fragment thereof may be any type of antibody or antigen-binding fragment thereof, which are capable of specifically recognizing and/binding to c-Met. The antigen-binding fragment may be scFv, (scFv)2, scFv-Fc, Fab, Fab' or F(ab')2.

The anti-c-Met antibody may be any antibody or antigen-binding fragment that acts on c-Met to induce intracellular internalization and degradation of c-Met. The anti-c-Met antibody may be any one recognizing a specific region of c-Met, e.g., a specific region in the SEMA domain, as an epitope.

c-Met, a receptor for hepatocyte growth factor (HGF), may be divided into three portions: extracellular, transmembrane, and intracellular. The extracellular portion is composed of an α-subunit and a β-subunit which are linked to each other through a disulfide bond, and contains a SEMA domain responsible for binding HGF, a PSI domain (plexin-semaphorin-integrin homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region having the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The region acts as an epitope for the specific anti-c-Met antibody of the present invention.

The term "epitope" as used herein, refers to an antigenic determinant, a part of an antigen recognized by an antibody. In one embodiment, the epitope for the c-Met antibody or antigen binding fragment thereof may be a region including about 5 or more contiguous amino acid residues within the SEMA domain (SEQ ID NO: 79) of c-Met protein, for instance, about 5 to about 19 contiguous amino acid residues within the amino acid sequence of SEQ ID NO: 71. For example, the epitope may be a polypeptide having about 5 to about 19 contiguous amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

Thus, the anti-c-Met antibody may specifically bind to an epitope which has about 5 to about 19 contiguous amino acids selected from among partial combinations of the amino acid sequence of SEQ ID NO: 71, including SEQ ID NO: 73 as an essential element. For example, the anti-c-Met antibody may specifically bind to an epitope including the amino acid sequence of SEQ ID NO: 71, SEQ ID NO: 72, or SEQ ID NO: 73.

In one embodiment, the anti-c-Met antibody or an antigen-binding fragment thereof may comprise or consist essentially of:

at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence having about 8-19 consecutive amino acids within SEQ ID NO: 2 including amino acid residues from the $3^{rd}$ to $10^{th}$ positions of SEQ ID NO: 2; and (c) a CDR-H3 including the amino acid sequence of SEQ ID NO: 6, SEQ ID NO: 15, SEQ ID NO: 85, or an amino acid sequence having about 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 15, SEQ ID NO: 86, or an amino acid sequence having 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

$Xaa_1$-$Xaa_2$-Tyr-Tyr-Met-Ser (SEQ ID NO: 4), Formula I wherein $Xaa_1$ is absent or Pro or Ser, and $Xaa_2$ is Glu or Asp, Arg-Asn-$Xaa_3$-$Xaa_4$-Asn-Gly-$Xaa_5$-Thr (SEQ ID NO: 5), Formula II wherein $Xaa_3$ is Asn or Lys, $Xaa_4$ is Ala or Val, and $Xaa_5$ is Asn or Thr, Asp-Asn-Trp-Leu-$Xaa_6$-Tyr (SEQ ID NO: 6), Formula III wherein $Xaa_6$ is Ser or Thr, Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala (SEQ ID NO: 7) Formula IV wherein $Xaa_7$ is His, Arg, Gln, or Lys, $Xaa_8$ is Ser or Trp, $Xaa_9$ is His or Gln, and $Xaa_{10}$ is Lys or Asn, Trp-$Xaa_{11}$-Ser-$Xaa_{12}$-Arg-Val-$Xaa_{13}$ (SEQ ID NO: 8) Formula V wherein $Xaa_{11}$ is Ala or Gly, $Xaa_{12}$ is Thr or Lys, and $Xaa_{13}$ is Ser or Pro, and $Xaa_{14}$-Gln-Ser-Tyr-Ser-$Xaa_{15}$-Pro-$Xaa_{16}$-Thr (SEQ ID NO: 9) Formula VI wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or antigen-binding fragment may comprise or consist essentially of:

a heavy chain variable region comprising a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85;

a light chain variable region comprising a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89; or a combination the heavy chain variable region and the light chain variable region.

In one embodiment, the anti-c-Met antibody or antigen-binding fragment may comprise or consist essentially of a heavy chain variable region comprising the amino acid sequence of SEQ ID NO: 17, 74, 87, 90, 91, 92, 93, or 94, a light chain variable region comprising the amino acid sequence of SEQ ID NO: 131, 18, 19, 20, 21, 75, 88, 95, 96, 97, 98, 99, or 107, or a combination of the heavy chain variable region and the light chain variable region.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, the disclosure of which is incorporated in its entirety herein by reference). The anti-c-Met antibody may include all the antibodies defined in Korean Patent Publication No. 2011-0047698.

By way of further example, the anti-c-Met antibody or the antibody fragment may include:

a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), the amino acid sequence from the $18^{th}$ to $462^{nd}$ positions of SEQ ID NO: 62, the amino acid sequence of SEQ ID NO: 64 (wherein the amino acid sequence from the $1^{st}$ to $17^{th}$ positions is a signal peptide), the amino acid sequence from the $18^{th}$ to $461^{st}$ positions of SEQ ID NO: 64, the amino acid sequence of SEQ ID NO: 66 (wherein the amino acid sequence from the $1^{st}$ to $17^{th}$ positions is a signal peptide), and the amino acid sequence from the $18^{th}$ to $460^{th}$ positions of SEQ ID NO: 66; and a light chain including the amino acid sequence selected from the group consisting of the amino acid sequence of SEQ ID NO: 68 (wherein the amino acid sequence from the $1^{st}$ to $20^{th}$ positions is a signal peptide), the amino acid sequence from the $21^{st}$ to $240^{th}$ positions of SEQ ID NO: 68, the amino acid sequence of SEQ ID NO: 70 (wherein the amino acid sequence from the $1^{st}$ to $20^{th}$ positions is a signal peptide), the amino acid sequence from the $21^{st}$ to $240^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 68 or the amino acid sequence from the $21^{st}$ to $240^{th}$ positions of SEQ ID NO: 68;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 70 or the amino acid sequence from the $21^{st}$ to $240^{th}$ positions of SEQ ID NO: 70;

an antibody including a heavy chain including the amino acid sequence of SEQ ID NO: 62 or the amino acid sequence from the $18^{th}$ to $462^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the $18^{th}$ to $461^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the $18^{th}$ to $460^{th}$ positions of SEQ ID NO: 66 and a light chain including the amino acid sequence of SEQ ID NO: 108.

According to an embodiment, the anti-c-Met antibody may include a heavy chain including the amino acid sequence from the $18^{th}$ to $460^{th}$ positions of SEQ ID NO: 66 and a light chain including the sequence from the $21^{st}$ to $240^{th}$ positions of SEQ ID NO: 68, or a heavy chain including the amino acid sequence from the $18^{th}$ to $460^{th}$ positions of SEQ ID NO: 66 and a light chain including the sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 of SEQ ID NO: 108 (corresponding to position 52 of SEQ ID NO: 68, which corresponds to position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The anti c-Met antibodies, the anti-EGFR antibodies and antigen-binding fragments thereof may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be recombinant or synthetic. The antibodies may be monoclonal.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ϵ) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "hinge region" as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody, the anti-EGFR antibody, or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100(U7-HC6), 101(U6-HC7), 102(U3-HC9), 103(U6-HC8), or 104(U8-HC5), or a hinge region including the amino acid sequence of SEQ ID NO: 105 (non-modified human hinge). In particular, the hinge region has the amino acid sequence of SEQ ID NO: 100 or 101.

In the anti-c-Met antibody, the portion of the light chain and the heavy chain excluding the CDRs, the light chain variable region, and the heavy chain variable region as defined above, for example the light chain constant region and the heavy chain constant region, may be those from any subtype of immunoglobulin (e.g., IgA, IgD, IgE, IgG (IgG1, IgG2, IgG3, IgG4), IgM, and the like).

The term "antigen-binding fragment" used herein refers to fragments of an intact immunoglobulin including portions of a polypeptide including at least one CDR or antigen-binding regions having the ability to specifically bind to the antigen. In a particular embodiment, the antigen-binding fragment may be scFv, $(scFv)_2$, scFvFc, Fab, Fab', or $F(ab')_2$, but is not limited thereto.

Among the antigen-binding fragments, Fab that includes light chain and heavy chain variable regions, a light chain constant region, and a first heavy chain constant region $C_{H1}$, has one antigen-binding site.

The Fab' fragment is different from the Fab fragment, in that Fab' includes a hinge region with at least one cysteine residue at the C-terminal of $C_{H1}$.

The $F(ab')_2$ antibody is formed through disulfide bridging of the cysteine residues in the hinge region of the Fab' fragment. Fv is the smallest antibody fragment with only a heavy chain variable region and a light chain variable region. Recombination techniques of generating the Fv fragment are widely known in the art.

Two-chain Fv includes a heavy chain variable region and a light chain region which are linked by a non-covalent bond. Single-chain Fv generally includes a heavy chain variable region and a light chain variable region which are linked by a covalent bond via a peptide linker or linked at the C-terminals to have a dimer structure like the two-chain Fv. The peptide linker may be the same as described in the above, for example, those having the amino acid length of about 1 to about 100, about 2 to about 50, particularly about 5 to about 25, and any kinds of amino acids may be included without any restriction.

The antigen-binding fragments may be attainable using protease (for example, the Fab fragment may be obtained by restricted cleavage of a whole antibody with papain, and the $F(ab')_2$ fragment may be obtained by cleavage with pepsin), or may be prepared by using a genetic recombination technique.

In one embodiment, the c-Met/EGFR dual inhibitor (such as an anti-c-Met/anti-EGFR bispecific antibody) may comprise 1) an anti-c-Met antibody or an antigen binding fragment thereof, and 2) an anti-EGFR antibody, an antigen binding fragment thereof, or an EGFR DARPin, which is linked to the C-terminus or N-terminus of the anti-c-Met antibody. For example, the C-terminus or N-terminus of the anti-EGFR antibody may be linked to the C-terminus of the anti-c-Met antibody (e.g., the C-terminus of a heavy chain of the anti-c-Met antibody) or the antigen binding fragment thereof. Alternatively, the C-terminus or N-terminus of the anti-EGFR antibody may be linked to the N-terminus of the anti-c-Met antibody or the antigen binding fragment thereof.

In the c-Met/EGFR dual inhibitor, in order to fully perform the anti-c-Met antibody's activity to mediate intracellular migration and degradation of c-Met proteins, it may be advantageous that the anti-c-Met antibody has its own intact antibody structure. In addition, in case of the EGFR binding domain such as an anti-EGFR antibody and the like, its specific recognition and binding to EGFR is important, and thus it will be fine that just an antigen-binding fragment recognizing EGFR is included in the dual inhibitor (e.g., the bispecific antibody). Therefore, the c-Met/EGFR dual inhibitor such as an anti-c-Met/anti-EGFR bispecific antibody may be those including a complete (full length) form of an anti-c-Met antibody (e.g., IgG (e.g., IgG1, IgG2, IgG3, or IgG4) type antibody; comprising two heavy chain and two light chains) and an antigen binding fragment of the anti-EGFR antibody (e.g., an anti-EGFR scFv) or an anti-EGFR DARPin linked to the C terminus of the anti-c-Met antibody.

In the c-Met/EGFR dual inhibitor, the c-Met binding domain such as anti-c-Met antibody or the antigen binding fragment thereof, and the EGFR binding domain such as the anti-EGFR antibody, the antigen binding fragment thereof, or the anti-EGFR DARPin, may be linked via a peptide linker, or they may be linked directly and without a linker. Furthermore, a heavy chain portion and a light chain portion within the antigen binding fragment, for example, a heavy chain variable region and a light chain variable region within the scFv fragment, may be linked via a peptide linker or without a linker. The peptide linker which links the anti-c-Met antibody or the antigen binding fragment thereof and the anti-EGFR antibody or the antigen binding fragment thereof, and the peptide linker which links the heavy chain portion and the light chain portion within the antigen binding fragment, may be identical or different. The peptide linker may be include about 1 to about 100 amino acid residues, particularly about 2 to about 50, and any kinds of amino acids may be included without any restrictions. The peptide linker may include for example, Gly, Asn and/or Ser residues, and also include neutral amino acids such as Thr and/or Ala. Amino acid sequences suitable for the peptide linker may be those known in the pertinent art. Meanwhile, a length of the peptide linker may be variously determined within such a limit that the functions of the fusion protein will not be affected. For instance, the peptide linker may be formed by including a total of about 1 to about 100, about 2 to about 50, or about 5 to about 25 of one or more selected from the group consisting of Gly, Asn, Ser, Thr, and Ala. In one embodiment, the peptide linker may be represented as SEQ ID NO: 132.

In the pharmaceutical composition (mixed formulation, first and second pharmaceutical compositions, etc.) or methods described herein, the active ingredients (a c-Met/EGFR dual inhibitor or an IGF-1R inhibitor) may be provided (comprised or administered) along with at least one additive selected from the group consisting of a pharmaceutically acceptable carriers, diluents, and excipients.

The pharmaceutically acceptable carrier to be included in the composition or mixed formulation may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative.

The pharmaceutical composition or mixed formulation may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

The pharmaceutically effective amount of the pharmaceutical composition, the c-Met/EGFR dual inhibitor, or the an IGF-1R inhibitor for a single dose may be prescribed in a variety of ways, depending on factors such as formulation methods, administration manners, age of subjects, body weight, gender, pathologic conditions, diets, administration time, administration interval, administration route, excretion speed, and reaction sensitivity. For example, the pharmaceutically effective amount of the IGF-1R inhibitor for a single dose may be in ranges of about 0.001 to about 100 mg/kg, or about 0.02 to about 10 mg/kg, and the pharmaceutically effective amount of the c-Met inhibitor for a single dose may be in ranges of about 0.001 to 100 mg/kg, or about 0.02 to about 10 mg/kg, but not limited thereto.

The term "pharmaceutically effective amount" used herein refers to an amount of the active ingredient (i.e., the c-Met/EGFR dual inhibitor, or the an IGF-1R inhibitor) exhibiting effects in preventing or treating cancer, and may be properly determined in a variety of ways, depending on factors such as formulation methods, administration methods, age of patients, body weight, gender, pathologic conditions, diets, administration time, administration route, excretion speed, and reaction sensitivity.

The pharmaceutically effective amount for the single dose may be formulated into a single formulation in a unit dosage form or formulated in suitably divided dosage forms, or it may be manufactured to be contained in a multiple dosage container. For the kit, the pharmaceutically effective amount of the c-Met/EGFR dual inhibitor and the pharmaceutically effective amount of the IGF-1R inhibitor for the single dose (one-time administration) may be each contained in a package container as a base unit.

In case that the co-administration comprises the sequential performance of the first administration step of administering the pharmaceutically effective amount of the c-Met/EGFR dual inhibitor and the second administration step of administering the effective amount of the IGF-1R inhibitor, the administration may be simultaneous or sequential with an interval between the first administration step and the second administration step of about 1 second to about 24 hours, about 1 second to about 12 hours, or about 1 second to about 60 minutes (e.g., about 1 second to about 10 minutes), and their administration may occur in any order. Alternatively, the administration interval between the co-administrations that is defined as a period between the co-administration and the subsequent co-administration may be, but not limited to, 1-60 seconds, 1-60 minutes, 1-24 hours, or 1-7 days, 1-14 days, 7-14 days, 1-30 days, or so on.

The mixed formulation or the pharmaceutical compositions for co-administration may be a solution in oil or an aqueous medium, a suspension, a syrup, or an emulsifying solution form, or they may be formulated into a form of an extract, powders, granules, a tablet or a capsule, and they may further include a dispersing agent or a stabilizing agent for their formulation.

In embodiments where the c-Met/EGFR dual inhibitor is an anti-c-Met antibody or an antigen binding fragment thereof and an anti-EGFR antibody or an antigen binding fragment thereof, the pharmaceutically effective amount of the c-Met inhibitor as an active ingredient may be formulated into an immunoliposome. A liposome containing an antibody may be prepared using any methods well known in the pertinent field. The immunoliposome is a lipid composition including phosphatidylcholine, cholesterol, and polyethyleneglycol-derivated phosphatidylethanolamine, which may be prepared by a reverse phase evaporation method. For example, Fab' fragments of an antibody may be conjugated to the liposome through a disulfide-exchange reaction. A chemical drug, such as doxorubicin, may further be included in the liposome.

The pharmaceutical composition and method for co-administration proposed in this disclosure can be used for preventing and/or treating a cancer. The cancer may be a cancer related to or characterized by overexpression and/or abnormal activation of c-Met and/or EGFR. The cancer may be a solid cancer or blood cancer. The cancer may be a cancer on which a c-Met/EGFR dual inhibitor such as an anti-c-Met/anti-EGFR bispecific antibody has no anticancer effect when treated alone (i.e., a cancer that is not sensitive (responsive) to a c-Met/EGFR dual inhibitor such as an anti-c-Met/anti-EGFR bispecific antibody in the absence of an IGF-1R inhibitor), or which has resistance to the c-Met/EGFR dual inhibitor, as well as a cancer on which the c-Met/EGFR dual inhibitor has anticancer effect when treated alone or which has no resistance to the c-Met/EGFR dual inhibitor. The cancer may also have a resistance to treatment with an IGF-1R inhibitor used alone, or the cancer may be sensitive to treatment with an IGF-1R inhibitor. For instance, the cancer may be, not limited to, at least one selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head and neck cancers, brain cancer, osteosarcoma and so on. In a particular embodiment, the cancer may a cancer having innate or acquired resistance to the c-Met/EGFR dual inhibitor. In addition, the cancer may be one selected from gastric cancer, lung cancer, and the like, which have high expression of IGF-1R, but not be limited thereto. The cancer may be a primary cancer or a metastatic cancer.

The prevention and/or treatment effects of the cancer may include effects of not only inhibiting the growth of the cancer cells but also inhibiting the ability of the cancer to migrate, invade healthy cells, and metastasize.

Another embodiment provides partners for combination therapy capable of improving the effect of each other and overcoming resistance to each. In particular, provided is a use of an IGF-1R inhibitor as a partner drug for co-administration with a c-Met/EGFR dual inhibitor, that is, the drug is suitable for use in a combination therapy using an c-Met/EGFR dual inhibitor, and allows the c-Met/EGFR dual inhibitor to exhibit the effect on a disease on which the c-Met/EGFR dual inhibitor has no effect when it administered alone or disease having resistance to the c-Met/EGFR dual inhibitor.

Therefore, an embodiment provides a pharmaceutical composition for improving the effect of a c-Met/EGFR dual inhibitor, which comprises an IGF-1R inhibitor. Another embodiment provides a method for improving the effect of a c-Met/EGFR dual inhibitor, comprising co-administering a c-Met/EGFR dual inhibitor together with an IGF-1R inhibitor.

The term "improving the effect of a c-Met/EGFR dual inhibitor" may comprise making the c-Met/EGFR dual inhibitor to have an effect on a disease (e.g., a cancer) on which the c-Met/EGFR dual inhibitor has no or only little effect when it is used alone and/or a disease (e.g., a cancer) having resistance to the c-Met/EGFR dual inhibitor. Therefore, the composition or method for improving the effect of a c-Met/EGFR dual inhibitor may a composition or method for overcoming (treating, reducing, and/or alleviating) resistance to the c-Met/EGFR dual inhibitor.

Another embodiment provides a biomarker for predicting and/or monitoring an effect of a c-Met/EGFR dual inhibitor, comprising at least one selected from the group consisting of IGF-1R protein and nucleic acids (full length DNA, cDNA, or mRNA) encoding IGF-1R. The nucleic acid encoding IGF-1R may be full length DNA, cDNA, or mRNA of nucleic acids (e.g., full-length DNA, cDNA or mRNA) encoding IGF-1R.

Another embodiment provides a composition or a kit for predicting and/or monitoring an effect of a c-Met/EGFR dual inhibitor, comprising a material interacting with at least one selected from the group consisting of IGF-1R protein and nucleic acids encoding IGF-1R.

Another embodiment provides a method for predicting and/or monitoring an effect of a c-Met/EGFR dual inhibitor, comprising measuring the level of at least one selected from the group consisting of IGF-1R protein and nucleic acids (full-length DNA, cDNA or mRNA) encoding IGF-1R in a biological sample from a subject (to be tested).

The term "predicting an effect of a c-Met/EGFR dual inhibitor" may refer to predicting (determining) whether or not the c-Met/EGFR dual inhibitor exhibit its effect on an individual subject by confirming a factor affecting the display of effect of the c-Met/EGFR dual inhibitor, such as the presence/absence of innate (inherent) resistance to the c-Met/EGFR dual inhibitor. When it is confirmed that a c-Met/EGFR dual inhibitor exhibits an effect on an individual subject, the subject may be determined as a subject suitable for application of the c-Met/EGFR dual inhibitor. Therefore, the biomarker, composition, kit, or method for predicting an effect of a c-Met/EGFR dual inhibitor may be a biomarker, composition, kit, or method for selecting a subject for application of the c-Met/EGFR dual inhibitor.

The term "monitoring an effect of a c-Met/EGFR dual inhibitor" may refer to monitoring whether the c-Met/EGFR dual inhibitor exhibits its effect well or not and/or resistance to the c-Met/EGFR dual inhibitor is induced (acquired) by administration of the c-Met/EGFR dual inhibitor or not. Therefore, the biomarker, composition, kit, or method for monitoring an effect of a c-Met/EGFR dual inhibitor may be a biomarker, composition, kit, or method for monitoring induction (or acquisition) of resistance to the c-Met/EGFR dual inhibitor in a subject administered with the c-Met/EGFR dual inhibitor.

In an embodiment, provided is a method for predicting an effect of a c-Met/EGFR dual inhibitor, selecting a subject for application of a c-Met/EGFR dual inhibitor, monitoring an effect of a c-Met/EGFR dual inhibitor, or monitoring induction (or acquisition) of resistance to a c-Met/EGFR dual inhibitor. In the resistance, since an anti-c-Met antibody is comprised in the c-Met/EGFR dual inhibitor, when a resistance to the anti-c-Met antibody exists, the c-Met/EGFR dual inhibitor may lose its effect. Therefore, the resistance may refer to a resistance to a c-Met/EGFR dual inhibitor and/or a resistance to an anti-c-Met antibody.

As described above, a high level of at least one selected from IGF-1R or nucleic acids encoding IGF-1R in a biological sample (e.g., cells, tissues, body fluid, etc.) obtained (separated) from a subject may indicate that the biological sample or the subject has resistance to an anti-c-Met antibody and/or a c-Met/EGFR dual inhibitor. Therefore, in the method for predicting an effect of a c-Met/EGFR dual inhibitor or selecting a subject for application of a c-Met/EGFR dual inhibitor, when at least one selected from IGF-1R or nucleic acids encoding IGF-1R is absent or present at a low level, it can be determined (predicted) that the c-Met/EGFR dual inhibitor will exhibit an effect well on the biological sample or the subject from which the biological sample is obtained, or that the biological sample or the subject from which the biological sample is suitable for application of the c-Met/EGFR dual inhibitor. Therefore, the method for predicting an effect of a c-Met/EGFR dual inhibitor or selecting a subject for application of a c-Met/EGFR dual inhibitor may further comprise, after the measuring step, determining (predicting) an effect of a c-Met/EGFR dual inhibitor in the subject, selecting a subject for application of a c-Met/EGFR dual inhibitor, or determining that the biological sample or the subject from which the biological sample is suitable for application of the c-Met/EGFR dual inhibitor, when at least one selected from IGF-1R and nucleic acids encoding IGF-1R is absent (not detected or not measured) or present at a low level.

As used herein, the term "at least one selected from IGF-1R or nucleic acids encoding IGF-1R is present at a low level" may refer to the level (amount) of at least one selected from IGF-1R or nucleic acids (e.g., full-length DNA, cDNA or mRNA) encoding IGF-1R in a biological sample (test sample) from a subject (to be tested) is lower than that of a reference sample. The reference sample may refer to a biological sample (e.g., cells, tissues, body fluid, etc.) on which the c-Met/EGFR dual inhibitor does not exhibit its effect (for example, an anticancer effect such as inhibiting of cancer cell proliferation, migration (metastasis), or invasion, or inducing cancer cell apoptosis, etc.), or a biological sample (e.g., cells, tissues, body fluid, etc.) separated (obtained) from a subject on which the c-Met/EGFR dual inhibitor does not exhibit its effect (for example, an anticancer effect such as inhibiting of cancer cell proliferation, migration (metastasis), or invasion, or inducing cancer cell apoptosis, etc.). For example, the reference sample may be at least one selected from the group consisting of, but not be limited to, H1373 (ATCC, CRL-5866) lung cancer cell line, HCC1806 (ATCC, CRL-2335) breast cancer cell line, Caki-1 (ATCC, HTB-46) renal cancer cell line, SKBR3 (ATCC, HTB-30) breast cancer cell line, BT474 (ATCC, HTB-20) breast cancer cell line, HT-29 (ATCC, HTB-38) colon cancer cell line, LoVo (ATCC, CCL-229) colon cancer cell line, HCT116 (ATCC, CCL-247) colon cancer cell line, SW620 (ATCC, CCL-227) colon cancer cell line, Ls174T (ATCC, CL-188) colon cancer cell line, and cell lines wherein resistance to an anti-c-Met antibody and/or resistance to a c-Met/EGFR dual inhibitor is induced by repeated or continued administration of the anti-c-Met antibody and/or c-Met/EGFR dual inhibitor.

The method for predicting an effect of a c-Met/EGFR dual inhibitor or selecting a subject for application of a c-Met/EGFR dual inhibitor may further comprise, after the measuring step and prior to the determining step (if it is comprised), comparing the level (amount) of at least one selected from IGF-1R or nucleic acids encoding IGF-1R in a biological sample (test sample) from a subject of interest (to be tested), with that of a reference sample as described above. For this, the method for predicting an effect of a c-Met/EGFR dual inhibitor or selecting a subject for application of a c-Met/EGFR dual inhibitor may further comprise, prior to the comparing step, measuring the level (amount) of at least one selected from IGF-1R or nucleic acids (e.g., full-length DNA, cDNA or mRNA) encoding IGF-1R in the reference sample.

The steps of measuring the level of at least one selected from IGF-1R or nucleic acids encoding IGF-1R in the biological sample and the reference sample are performed simultaneously or sequentially in any order.

Alternatively, if the IGF-1R level, which is determined by immunohistochemistry (IHC) using a conventional anti-IGF-1R-antibody (e.g., SAB4300359 (SIGMA), or G11 (Ventana; Catalog Number: 790-4346), etc.), is 0 to +1, it can be determined that IGF-1R is present at a low level or absent.

The method for predicting an effect of a c-Met/EGFR dual inhibitor or selecting a subject for application of a c-Met/EGFR dual inhibitor may further comprise, after the measuring, comparing, or determining step, administering a c-Met/EGFR dual inhibitor to the subject, when at least one selected from IGF-1R and nucleic acids encoding IGF-1R is absent (not detected or not measured) or present at a low level compared to the reference sample, as described above.

In another embodiment, a method for monitoring an effect of a c-Met/EGFR dual inhibitor, comprising measuring the level (amount) of at least one selected from IGF-1R or nucleic acids (e.g., full-length DNA, cDNA or mRNA) encoding IGF-1R in a biological sample from a subject who is administered with the c-Met/EGFR dual inhibitor (or after administration of a c-Met/EGFR dual inhibitor). As described above, the method for monitoring an effect of a c-Met/EGFR dual inhibitor includes monitoring whether resistance to an anti-c-Met antibody and/or a c-Met/EGFR dual inhibitor is induced (acquired) or not.

In the method of monitoring an effect of a c-Met/EGFR dual inhibitor, it can be determined that a c-Met/EGFR dual inhibitor exhibits its effect (for example, an anticancer effect such as inhibiting of cancer cell proliferation, migration (metastasis), or invasion, or inducing cancer cell apoptosis, etc.) in the subject or resistance to the c-Met/EGFR dual inhibitor is not induced in the subject, if the level (amount) of at least one selected from IGF-1R or nucleic acids encoding IGF-1R in a biological sample from the subject who is administered with the c-Met/EGFR dual inhibitor (or after administration of a c-Met/EGFR dual inhibitor) is equal to (maintained) or decreased compared to that of a biological sample from a subject who is not administered with the c-Met/EGFR dual inhibitor (or before administration of a c-Met/EGFR dual inhibitor). Alternatively, it can be also determined that a c-Met/EGFR dual inhibitor does not exhibit its effect (for example, an anticancer effect such as inhibiting of cancer cell proliferation, migration (metastasis), or invasion, or inducing cancer cell apoptosis, etc.) in the subject or resistance to the c-Met/EGFR dual inhibitor is induced in the subject, if the level (amount) of at least one selected from IGF-1R or nucleic acids encoding IGF-1R in a biological sample from the subject who is administered with the c-Met/EGFR dual inhibitor (or after administration of a c-Met/EGFR dual inhibitor) is increased compared to that of a biological sample from a subject who is not administered with the c-Met/EGFR dual inhibitor (or before administration of a c-Met/EGFR dual inhibitor).

Therefore, the measuring step of the method of monitoring an effect of a c-Met/EGFR dual inhibitor may comprise measuring the levels (amount) of at least one selected from IGF-1R or nucleic acids (e.g., full-length DNA, cDNA or mRNA) encoding IGF-1R in a biological sample from a subject before and after the subject is administered with a c-Met/EGFR dual inhibitor.

In addition, the method of monitoring an effect of a c-Met/EGFR dual inhibitor may further comprise, after the measuring step, comparing the levels of at least one selected from IGF-1R or nucleic acids encoding IGF-1R in a biological sample from a subject before and after the subject is administered with a c-Met/EGFR dual inhibitor, and/or determining that 1) the c-Met/EGFR dual inhibitor exhibits its effect (for example, an anticancer effect such as inhibiting of cancer cell proliferation, migration (metastasis), or invasion, or inducing cancer cell apoptosis, etc.) in the subject, a resistance to the c-Met/EGFR dual inhibitor is not induced (not acquired) in the subject, or the treatment using the c-Met/EGFR dual inhibitor can be maintained to the subject, when the level of at least one selected from IGF-1R or nucleic acids encoding IGF-1R in a biological sample from the subject after administration of a c-Met/EGFR dual inhibitor is equal to or decreased compared to that of a biological sample from a subject before administration of a c-Met/EGFR dual inhibitor, and/or 2) the c-Met/EGFR dual inhibitor does not exhibit its effect (for example, an anticancer effect such as inhibiting of cancer cell proliferation, migration (metastasis), or invasion, or inducing cancer cell apoptosis, etc.) in the subject, a resistance to the c-Met/EGFR dual inhibitor is induced (acquired) in the subject, or the treatment using the c-Met/EGFR dual inhibitor is stopped to the subject, when the level of at least one selected from IGF-1R or nucleic acids encoding IGF-1R in a biological sample from the subject after administration of a c-Met/EGFR dual inhibitor is increased compared to that of a biological sample from a subject before administration of a c-Met/EGFR dual inhibitor. The c-Met/EGFR dual inhibitor may be an anti-c-Met/anti-EGFR bispecific antibody.

The method of monitoring an effect of a c-Met/EGFR dual inhibitor may further comprise, after the measuring, comparing, or determining step, maintaining the administration a c-Met/EGFR dual inhibitor to the subject, when at least one selected from IGF-1R or nucleic acids encoding IGF-1R after a c-Met/EGFR dual inhibitor administration is equal to or decreased compared to that of before the c-Met/EGFR dual inhibitor administration.

In addition, as described above, when an IGF-1R inhibitor is co-administered with a c-Met/EGFR dual inhibitor, the effect of the c-Met/EGFR dual inhibitor can be improved (for example, resistance to an anti-c-Met antibody and/or a c-Met/EGFR dual inhibitor can be overcome); and thus, even if at least one selected from the group consisting of IGF-1R and a nucleic acid encoding IGF-1R exists in a biological sample from a subject, a desired effect can be achieved by co-administration of an IGF-1R inhibitor and a c-Met/EGFR dual inhibitor.

Therefore, another embodiment provides a method for predicting an effect of a combined administration of a c-Met/EGFR dual inhibitor and an IGF-1R inhibitor, and/or selecting a patient for application of a combined administration of a c-Met/EGFR dual inhibitor and an IGF-1R inhibitor, the method comprising measuring a level of at least one selected from the group consisting of IGF-1R and a nucleic acid encoding IGF-1R in a biological sample from a subject. As described above, the detection (presence) of at least one selected from the group consisting of IGF-1R and a nucleic acid encoding IGF-1R in a biological sample from a subject may indicate that the biological sample or the subject has innate (inherent) or acquired resistance to an anti-c-Met antibody and/or a c-Met/EGFR dual inhibitor; however, co-administration of a c-Met/EGFR dual inhibitor and an IGF-1R inhibitor can overcome such resistance, thereby achieving an increased therapeutic effect despite such resistance.

Therefore, the method for predicting an effect of a combined administration of a c-Met/EGFR dual inhibitor and an IGF-1R inhibitor and/or selecting a subject for application of a combined administration of a c-Met/EGFR dual inhibitor and an IGF-1R inhibitor, may further comprise predicting that the combined administration of a c-Met/EGFR dual inhibitor and an IGF-1R inhibitor is effective on the biological sample or the subject from which the biological sample is obtained or determining that the biological sample or the subject from which the biological sample is obtained is suitable for application of the combined administration of a c-Met/EGFR dual inhibitor and an IGF-1R inhibitor, if at least one selected from the group consisting of IGF-1R and a nucleic acid encoding IGF-1R is detected (present) in a biological sample from a subject. In an embodiment, the biological sample or biological sample or the subject from which the biological sample is obtained may have a resistance to an anti-c-Met antibody and/or a c-Met/EGFR dual inhibitor, which is innate (inherently) or acquired by repeated administration of a c-Met/EGFR dual inhibitor, wherein such innate (inherently) or acquired resistance to a c-Met/EGFR dual inhibitor can be overcome by co-administration of the c-Met/EGFR dual inhibitor together with an IGF-1R inhibitor.

In the above described method for predicting or monitoring an effect of a c-Met/EGFR dual inhibitor or a combined administration of a c-Met/EGFR dual inhibitor and an IGF-1R inhibitor or selecting a subject for application of a c-Met/EGFR dual inhibitor or a combined administration of a c-Met/EGFR dual inhibitor and an IGF-1R inhibitor, the step of measuring the level of at least one selected from IGF-1R or nucleic acids encoding IGF-1R (e.g., the step of measuring the level of at least one selected from IGF-1R or nucleic acids encoding IGF-1R in a biological sample from a subject and a reference sample or in a biological sample from a subject before and after the subject is administered with a c-Met/EGFR dual inhibitor may comprise i) applying (adding) an interacting material that interacts with at least one selected from the group consisting IGF-1R or nucleic acids (e.g., full-length DNA, cDNA or mRNA) encoding IGF-1R to the biological sample and/or a reference sample; and ii) quantitatively analyzing the resulting reaction mixture to determine a level (amount) of at least one selected from the group consisting of IGF-1R or nucleic acids (e.g., full-length DNA, cDNA or mRNA) encoding IGF-1R.

In an embodiment, prior to the step i), a step of providing a biological sample (and/or a reference sample) may be further performed. The step of providing a biological sample may comprise obtaining (isolating) a biological sample from a subject or obtaining a biological sample which has been isolated from a subject.

In step i), as will be further elucidated below, the interacting material may be at least one selected from the group consisting of compounds (a small molecular chemical; e.g., general label such as a fluorescent, a dye, etc.), proteins (antibodies, aptamers, etc.), nucleic acids (DNA, RNA, etc.), and the like, binding to IGF-1R or nucleic acids (e.g., full-length DNA, cDNA or mRNA) encoding IGF-1R. For example, the interacting material may be at least one selected from the group consisting of a compound, an antibody, an aptamer, all specifically binding to IGF-1R, and a nucleic acid (e.g., a primer, a probe, an aptamer, etc.) binding to a part or entirety of a nucleic acid (e.g., full-length DNA, cDNA or mRNA) encoding IGF-1R, and optionally, may be conjugated with a label, such as a fluorescent or a dye. The step i) may be configured to form a complex by applying (adding) the interacting material to the biological sample (and/or a reference sample).

In step ii), the reaction mixture may be a complex resulting from interaction (binding) between at least one selected from the group consisting of IGF-1R and a nucleic acid (e.g., full-length DNA, cDNA or mRNA) encoding IGF-1R and the interacting material, which can be obtained in step i). The quantitatively analyzing step may comprise quantifying the complex, the label conjugated to the complex, or the IGF-1R or the nucleic acid gene segregated from the complex after the isolation of the complex from the biological sample (and/or the reference sample). The quantitative analysis of IGF-1R may be performed by any general quantifying means of proteins, such as immunochromatography, immunohistochemistry, immunohistochemical staining, enzyme linked immunosorbent assay (ELISA), radioimmunoassay (RIA), enzyme immunoassay (EIA), fluorescence immunoassay (FIA), luminescence immunoassay (LIA), Western blotting, microarray, surface plasmon resonance (SPR), flow cytometry assay (e.g., Cytometric Bead Array (CBA) assay), Intracellular staining, Luminex assay, and the like, but not limited thereto. The quantitative analysis of nucleic acids (e.g., full-length DNA, cDNA or mRNA) encoding IGF-1R may be performed by any general quantifying means of genes (DNA or RNA), such as polymerase chain reaction (PCR; e.g., qPCR, RT-PCR, etc.), FISH (fluorescent in situ hybridization), microarray (e.g., mRNA microarray), and the like, but not limited thereto, which may use the interacting material such as a primer, a probe, or an aptamer, all capable of hybridizing (hybridizable) with a part or entirety of the nucleic acids encoding IGF-1R. In an embodiment, In one embodiment, the primer is designed to detect a fragment of successive base pairs out of the nucleic acid (full-length DNA, cDNA or mRNA) encoding IGF-1R, for example, a fragment of about 5 to about 2000 bp or about 5 to about 1000 bp, e.g., about 10 to about 1500 bp, about 10 to about 1000 bp, about 10 to about 500 bp, about 20 to about 200 bp, or about 50 to about 200 bp, and may be a pair of primers having nucleotide sequences which are respectively hybridizable with (e.g., complementary to) 3'- and 5'-terminal regions of the fragment, the region ranging in size from about 5 to about 100 bp, e.g., about 5 to about 50 bp, about 5 to about 30 bp, or about 10 to about 25 bp (that is, each of the primer pair comprises about 5 to about 100 nt, e.g., about 5 to about 50 nt, about 5 to about 30 nt, or about 10 to about 25 nt). The probe or the aptamer hybridizable with a part or entirety of the nucleic acid encoding IGF-1R may have a nucleotide sequence with a size from about 5 to about 2000 nt, from about 5 to about 1500 nt, from about 5 to about 1000 nt, from about 5 to about 500 nt, from about 5 to about 100 nt, from about 5 to about 50 nt, from about 5 to about 30 nt, or from about 5 to about 25 nt, which is hybridizable with (or complementary to) a fragment of the nucleic acid encoding IGF-1R. As used herein, the term "hybridizable" means pertaining to complementarily binding to a specific region of the nucleic acid, with a sequence complementarity of 80% or higher, e.g., 90% or higher, 95% or higher, 98% or higher, 99% or higher, or 100% between the primer, probe or aptamer and the nucleic acid region.

Considering that characteristic of the therapy using a c-Met/EGFR dual inhibitor such as an anti-c-Met/anti-EGFR bispecific antibody, a high level expression of c-Met in a cancer cell can serve as an advantageous condition so that a c-Met/EGFR dual inhibitor can more effectively exhibit its effect (e.g., an anticancer effect). Therefore, c-Met and/or nucleic acids (e.g., full-length DNA, cDNA or mRNA) encoding c-Met may be serve as a marker for predicting or monitoring an effect of a c-Met/EGFR dual inhibitor or selecting a subject for application of a c-Met/EGFR dual inhibitor, and it may be used alone or in combination with IGF-1R and/or nucleic acid encoding IGF-1R.

Therefore, the composition for predicting or monitoring an effect of a c-Met/EGFR dual inhibitor or selecting a subject for application of a c-Met/EGFR dual inhibitor may further comprise an interacting material that interacts with at least one selected from the group consisting of c-Met and nucleic acids encoding c-Met, in addition to an interacting material that interacts with IGF-1R and/or nucleic acid encoding IGF-1R as described above. The interacting material that interacts with c-Met and/or nucleic acid encoding c-Met may be at least one selected from the group consisting of compounds (a small molecular chemical), proteins (antibodies, aptamers, etc.), nucleic acids (DNA, RNA, etc.), and the like, binding to c-Met or nucleic acids (e.g., full-length DNA, cDNA or mRNA) encoding c-Met. For example, the interacting material may be at least one selected from the group consisting of a compound, an antibody, an aptamer, all specifically binding to c-Met, and a nucleic acid (e.g., a primer, a probe, an aptamer, etc.) binding to a part or entirety of a nucleic acid (e.g., full-length DNA, cDNA or mRNA) encoding c-Met, and optionally, may be conjugated with a label, such as a fluorescent or a dye.

The method for predicting or monitoring an effect of a c-Met/EGFR dual inhibitor or selecting a subject for application of a c-Met/EGFR dual inhibitor may further comprise measuring a level of c-Met protein or a gene thereof (e.g., full-length DNA, cDNA, mRNA) in the biological sample from a subject. The steps of measuring the level of c-Met and/or c-Met coding nucleic acid and measuring the level of at least one selected from the group consisting of IGF-1R and nucleic acid encoding IGF-1R may be performed simultaneously or sequentially in any order. Details of the measuring step are as described above. For example, a western blotting technique may be employed. In this regard, when a predetermined amount (e.g., about 10 μg) of proteins obtained from a biological sample (e.g., cancer cells or tissues) is loaded on SDS PAGE gel, transferred onto the membrane, and reacted with an anti-c-Met antibody, and then, exposed on ECL reaction for a certain time (e.g., about 30 sec), the detection of a band may indicate that a prerequisite for the c-Met inhibitor therapy is established. In another embodiment, when a biological sample is found to have a c-Met mRNA level of about 13.5 or higher, about 13.6 or higher, or about 13.78 or higher, as measured by Affymetrix array (Affymetrix GeneChip Human Genome U133 Plus 2.0 array; using the primer set "203510_at"), a prerequisite for a c-Met/EGFR dual inhibitor therapy may be established. Cancer cells characterized by a high expression level of c-Met include cells from lung cancer, breast cancer, brain cancer, stomach cancer, liver cancer, and kidney cancer. However, any cancer cell, although derived from different kinds, may be a target of the c-Met inhibitor therapy if it expresses a high level of c-Met according to personal characteristics of patients.

In an embodiment, the biological sample used in the method for predicting or monitoring an effect of a c-Met/EGFR dual inhibitor or selecting a subject for application of a c-Met/EGFR dual inhibitor may be a tissue, a cell or body fluid (blood, serum, urine, saliva, etc.) which shows a high expression level of c-Met, for example, a c-Met level of about 13.5 or higher, about 13.6 or higher, or about 13.78 or higher, as measured by Affymetrix array (Affymetrix GeneChip Human Genome U133 Plus 2.0 array; using the primer set "203510_at").

As used herein, the term "subject (suitable) for the application of a c-Met/EGFR dual inhibitor" means a patient to which a c-Met/EGFR dual inhibitor therapy is applicable suitably, and the term "subject" may be selected from the group consisting of mammals, such as rodents, e.g., mice, rats, etc., and primates, e.g., humans, monkeys, etc., e.g., a cancer patient. The biological sample may be a patient itself (mammals, such as primates, e.g., humans, monkeys, etc., or rodents, e.g., mice, rats, etc.) or a cell, a tissue or body fluid (e.g., blood, serum, urine, saliva, etc.) isolated from the patient or artificially an artificial culture thereof. The biological sample may be a cell, blood, or a serum.

Another embodiment provides a method of treating and/or preventing a cancer comprising co-administering a c-Met/EGFR dual inhibitor to a subject in need thereof. In the method of preventing and/or treating cancer, the subject may be one from whom a biological sample shows a low level (amount) of at least one selected from the group consisting of IGF-1R and a nucleic acid encoding IGF-1R compared to a reference sample, therein the term "low level" and "reference sample" are as described above. For example, the subject may be 1) selected by the above method for selecting a subject for the application of a combined administration of a c-Met/EGFR dual inhibitor.

Another embodiment provides a method of treating and/or preventing a cancer comprising co-administering a c-Met/EGFR dual inhibitor and an IGF-1R inhibitor to a subject in need thereof. In the method of preventing and/or treating cancer, the subject may be one from whom a biological sample shows the presence of at least one selected from the group consisting of IGF-1R and a nucleic acid encoding IGF-1R. For example, the subject may be selected by the above method for selecting a subject for the application of a combined administration of a c-Met/EGFR dual inhibitor and an IGF-1R inhibitor.

The method of treating and/or preventing a cancer may further comprise identifying (selecting) the subject for application of a c-Met/EGFR dual inhibitor or application of a combined administration of a c-Met/EGFR dual inhibitor and an IGF-1R inhibitor, wherein the detailed process can be performed referring to the method of selecting a subject described above. The c-Met/EGFR dual inhibitor may be an anti-c-Met/anti-EGFR bispecific antibody.

In the above methods of treating and/or preventing a cancer, the c-Met/EGFR dual inhibitor and/or the IGF-1R inhibitor may be administered at a pharmaceutically effective amount as described above.

For example, the method of treating and/or preventing a cancer may comprise:

identifying a subject for application of a c-Met/EGFR dual inhibitor; and administering a c-Met/EGFR dual inhibitor to the subject.

Alternatively, the method of treating and/or preventing a cancer may comprise:

identifying a subject for application of combined administration of a c-Met/EGFR dual inhibitor and an IGF-1R inhibitor; and co-administering a c-Met/EGFR dual inhibitor and an IGF-1R inhibitor to the subject.

Alternatively, the method of treating and/or preventing a cancer may comprise:

selecting a subject for application of a c-Met/EGFR dual inhibitor by measuring the level of IGF-1R and/or nucleic acid encoding IGF-1R in a biological sample from a subject; and administering a c-Met/EGFR dual inhibitor to the subject.

Alternatively, the method of treating and/or preventing a cancer may comprise:

selecting a subject for application of combined administration of a c-Met/EGFR dual inhibitor and an IGF-1R inhibitor by measuring the level of IGF-1R and/or nucleic acid encoding IGF-1R in a biological sample from a subject; and administering a c-Met/EGFR dual inhibitor and an IGF-1R inhibitor to the subject.

In the above methods of treating and/or preventing a cancer, the step of selecting a subject may be performed referring to the above descriptions.

EXAMPLES

Hereafter, the present invention will be described in detail by examples.

The following examples are intended merely to illustrate the invention and are not construed to restrict the invention.

Reference Example 1: Construction of Anti-c-Met Antibody 1.1. Production of "AbF46", a Mouse Antibody to c-Met 1.1.1. Immunization of Mouse To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1\times10^8$ cells) were mixed with myeloma cells (Sp2/0) ($1\times10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1\sim2\times10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS therefrom. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vk1 subtype. Back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFv Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker including the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of Target CDRs and Synthesis of Primers The affinity maturation of huAbF46 was achieved. First, six complementary determining regions (CDRs) were defined according to Kabat numbering. The CDRs are given in Table 2, below.

TABLE 2

| CDR | Amino Acid Sequence |
|---|---|
| CDR-H1 | DYYMS (SEQ ID NO: 1) |
| CDR-H2 | FIRNKANGYTTEYSASVKG(SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 3 and were converted into IgG forms. Four antibodies which were respectively produced from clones L3-1, L3-2, L3-3, and L3-5 were used in the subsequent experiments.

TABLE 3

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |

TABLE 3-continued

| Clone | Library constructed | CDR Sequence |
|---|---|---|
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. The histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (invitrogen). 293 F cells were used for the expression and cultured in FreeStyle™ 293 Expression Medium in a suspension culture manner. At one day before the transient expression, the cells were provided in the concentration of $5\times10^5$ cells/ml, and after 24 hours, when the cell number reached to $1\times10^6$ cells/ml, the transient expression was performed. A transfection was performed by a liposomal reagent method using Freestyle™ MAX reagent (invitrogen), wherein in a 15 ml tube, the DNA was provided in the mixture ratio of 1:1 (heavy chain DNA:light chain DNA) and mixed with 2 ml of OptiPro™ SFM (invtrogen) (A), and in another 15 ml tube, 100 ul (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was selected for the following examples, and name as L3-1Y-IgG2.

Reference Example 2: Preparation of a c-Met/EGFR Dual Inhibitor

2.1. Preparation of Anti-EGFR scFv

An anti-EGFR scFv binding to EGFR was prepared by inserting a peptide linker of $(GGGGS)_3$ (SEQ ID NO: 132) between a heavy chain variable region of SEQ ID NO: 115 and a light chain variable region of SEQ ID NO: 116. In particular, the DNA sequence encoding a $(GGGGS)_3$ linker peptide was added to the DNA sequence (SEQ ID NO: 119) encoding the heavy chain variable region (SEQ ID NO: 115) and the DNA sequence (SEQ ID NO: 120) encoding the light chain variable region (SEQ ID NO: 116) of a humanized anti-EGFR antibody using automatic gene synthesis (Bioneer Inc.) to synthesize a DNA fragment encoding a scFv of the anti-EGFR antibody. An anti-EGFR scFv prepared from the synthesized DNA fragment was named "anti-EGFR antibody E-2".

The amino acid sequences of the heavy chain variable region and the light chain variable region of the prepared anti-EGFR scFv, and coding nucleotide sequences thereof are summarized in Table 4, as follows (wherein the sequences marked in bold type indicate CDRs, i.e., CDR-H1, CDR-H2, and CDR-H3, or CDR-L1, CDR-L2, and CDR-L3, in sequence):

TABLE 4

| | Heavy chain variable region of anti-EGFR antibody E-2 | Light chain variable region of anti-EGFR antibody E-2 |
|---|---|---|
| Amino acid sequence | EVQLLESGGGLVQPGGSLRLSCAASGFTFS**NYDMS**WVRQAPGKGLEWV**SGISHSSGSKYYADSVKG**RFTISRDNSKNTLYLQMNSLRAEDTAVYYCAK**DATPRPLKPFDY**WGQGTLVTVSS (SEQ ID NO: 115) | QSVLTQPPSASGTPGQRVTISC**TGSSSNIGNNDVS**WYQQLPGTAPKLLIY**DDNKRPS**GVPDRFSGSKSGTSASLAISGLRSEDEADYYC**GSWDASLNA**YVFGGGTKLTVLG (SEQ ID NO: 116) |
| Coding nucleotide sequence | GAGGTGCAGCTGTTGGAGTCTGGGGGAGGCTTGGTACAGCCTGGGGGGTCCCTGAGACTCTCCTGTGCAGCCTCTGGATTCACCTTTAGC**AATTATGATATGAGC**TGGGTCCGCCAGGCTCCAGGGAAGGGGCTGGAGTGGGTCTCA**GGGATCTCTCATAGTAGTGGTAGTAAATATTACGCTGATTCTGTAAAAGGT**CGGTTCACCATCTCCAGAGACAATTCCAAGAACACGCTGTATCTGCAAATGAACAGCCTGAGAGCCGAGGACACGGCCGTGTATTACTGTGCG**AAAGATGCTACTCCGCGTCCGCTGAAGCCTTTCGACTAC**TGGGGCCAGGGTACACTGGTCACCGTGAGCTCA (SEQ ID NO: 119) | CAGTCTGTGCTGACTCAGCCACCCTCAGCGTCTGGGACCCCCGGGCAGAGGGTCACCATCTCTTGT**ACTGGCTCTTCATCTAATATTGGCAATAATGATGTCTCC**TGGTACCAGCAGCTCCCAGGAACGGCCCCCAAACTCCTCATCTAT**GATGATAATAAGCGGCCAAGC**GGGGTCCCTGACCGATTCTCTGGCTCCAAATCTGGCACCTCAGCCTCCCTGGCCATCAGTGGGCTCCGGTCCGAGGATGAGGCTGATTATTACTGT**GGTTCTTGGGATGCTAGCCTGAATGCT**TATGTCTTCGGCGGAGGCACCAAGCTGACGGTCCTAGGC (SEQ ID NO: 120) |

A modified anti-EGFR scFv (heavy chain variable region: SEQ ID NO: 117 and light chain variable region: SEQ ID NO: 118) was prepared as described above, with the exception that the amino acid, G, at $44^{th}$ position of the heavy chain variable region (SEQ ID NO: 115) was substituted with C, and the amino acid, G, at $100^{th}$ position of the light chain variable region (SEQ ID NO: 116) was substituted with C. The amino acid location within the antibody complies with kabat numbering system. Such modifications (substitutions) can increase the stability of the anti-EGFR scFv.

<SEQ ID NO: 117: heavy chain variable region of modified anti-EGFR antibody E-2>

EVQLLESGGGLVQPGGSLRLSCAASGFTFSNYDMSWVRQAPGKCLEWVSGISH SSGSKYYADSVKGRFTISRDNSKNTLYLQMNSLRAEDTAVYYCAKDATPRPLKPFDY WGQGTLVTVSS (wherein the sequences marked in bold type indicate CDRs, i.e., CDR-H1, CDR-H2, and CDR-H3, in sequence)

<SEQ ID NO: 118: light chain variable region of modified anti-EGFR antibody E-2>

QSVLTQPPSASGTPGQRVTISCTGSSSNIGNNDVSWYQQLPGTAPKLLIYDDNK RPSGVPDRFSGSKSGTSASLAISGLRSEDEADYYCGSWDASLNAYVFGCGTKLTVLG (wherein the sequences marked in bold type indicate CDRs, i.e., CDR-L1, CDR-L2, and CDR-L3, in sequence)

The obtained modified anti-EGFR scFv (including SEQ ID NO: 117 and SEQ ID NO: 118) was used to manufacture the following bispecific antibodies.

2.2. Preparation of a c-Met/EGFR Dual Inhibitor (Anti-c-Met/Anti-EGFR Bispecific Antibody)

The modified anti-EGFR scFv (including SEQ ID NO: 117 and SEQ ID NO: 118) prepared in the above Reference Example 2.1 was fused at the c-terminus of the Fc portion of the anti-c-Met antibody L3-1Y-IgG2 prepared in the above reference example 1. The fusion procedures are as follows.

A DNA segment having a base sequence (SEQ ID NO: 66) corresponding to the heavy chain of the anti-c-Met antibody L3-1Y-IgG2 prepared in above reference example 1 was inserted into a pcDNA™3.3-TOPO TA Cloning Kit (Cat no. 8300-01) which is included in OptiCHO™ Antibody Express Kit (Cat no. 12762-019) by Invitrogen Inc., and a DNA segment having a base sequence (SEQ ID NO: 68) corresponding to the light chain of the anti-c-Met antibody L3-1Y-IgG2 was inserted into a pOptiVEC™-TOPO TA Cloning Kit. Thereafter, the anti-EGFR scFv coding DNA prepared in Example 1 was fused at the c-terminus of the Fc portion of L3-1Y-IgG2 inserted into pcDNA™3.3, using the coding DNA sequence of a linker peptide having 10 amino acid lengths consisting of $(GGGGS)_2$ (SEQ ID NO: 133), to construct vectors for the expression of bispecific antibodies.

The constructed vectors were each amplified using Qiagen Maxiprep kit (Cat no. 12662 and transient expression of the constructed vectors was obtained using the Freestyle™ MAX 293 Expression System (invitrogen). The cell line used was 293 F cells, which were cultured in a suspension culture using FreeStyle™ 293 Expression Medium. One day before the transient expression, the cells were prepared at a concentration of $5\times10^5$ cells/ml and after 24 hours, their transient expression started when the number of the cells reached $1\times10^6$ cells/ml. Transfection was performed by a liposomal reagent method using Freestyle™ MAX reagent (invitrogen). DNA was prepared in a 15-ml tube in a ratio of heavy chain DNA:light chain DNA=3:2 and mixed with 2 ml of OptiPro™ SFM (invtrogen) (A), and 100 μl of Freestyle™ MAX reagent and 2 ml of OptiPro™ SFM were mixed in another 15-ml tube (B), and after (A) and (B) were mixed and incubated for 15 min., the mixture solution was then slowly mixed into the cells which were prepared one day before. After the transfection was complete, the cells were cultured in a 37° C., 80% humidity, 8% $CO_2$, 130 rpm incubator for 5 days.

The cultured cells were centrifuged to obtain 100 ml of supernatants, which were then purified using AKTA Prime (GE healthcare). The culture was flowed at a flow rate of 5 ml/min. onto the AKTA Prime installed with Protein A column (GE healthcare, 17-0405-03) to perform elution using an IgG elution buffer (Thermo Scientific, 21004). The buffer was replaced by a PBS buffer to finally obtain purified a c-Met/EGFR dual inhibitor (an anti-c-Met/anti-EGFR bispecific antibody).

The prepared anti-c-Met/anti-EGFR bispecific antibody in which the modified anti-EGFR scFv is fused at the c-terminal of L3-1Y-IgG2 was named ME22S.

Example 1: Measurement of the Level of IGF-1R Protein in Lung Cancer Cells and Gastric Cancer Cells In the lung cancer cell lines H820 (ATCC, HTB-181) and HCC827 (ATCC, CRL-2868), and gastric cancer cell lines SNU5 (ATCC, CRL-5973), SNU668 (KCLB, 00668), and MKN45(JCRB 0254), the level of IGF-1R protein was measured.

In particular, each of the cell lines was seeded on a 60 mm plate at the amount of $2\times10^5$ cells/ml, and 48 hours after, collected and lysed using lysis buffer (lysis-M, Roche), to extract proteins. Thereafter, the amounts of IGF-1R and GAPDH proteins were measured by western blotting (antibodies used: products of Cell signaling).

The results, shown in the upper part of FIG. 1, indicate that for lung cancer cells, the level of IGF-1R is relatively high in the HCC827 line, whereas it is considerably low in H820 cell line. For gastric cancer cells, IGF-1R is nearly absent in the SNU5 cell line, whereas it is present at a relatively high levels in the SNU668 and MKN45 cell lines.

The five cell lines were co-administered with ME22S prepared in Reference 2 and IGF-1R inhibitor, linsitinib (Selleck Chemical S1091), to measure the cell proliferation inhibition effect and examine the correlation between the effect or treatment and the level of IGF-1R.

For the cell proliferation assays, each of the cell lines were seeded on 96-well plate at the amount of $5\times10^3$ cells/well, and 24 hours later were treated with the ME22S antibody at a concentration of 0 nM, 0.08 nM, 0.4 nM, 2 nM, or 1.0 nM, in presence or absence of linsitinib (10 μM). 72 hours after the treatment with the antibody and/or the inhibitor drug, the number of living cells was counted using a CellTiter Glo assay (Promega, G7573). This assay measures the amount of ATP which reflects metabolism of living cells, thereby counting the number of living cells.

The results, shown in bottom part of FIG. 1, indicate that in cell lines H820 and SNU5 which have low levels of IGF-1R, there is no or only slight effect of co-administration of ME22S and linsitinib, whereas in cell lines HCC827, SNU668, and MKN45 which have high levels of IGF-1R, there is considerable effect of the co-administration. These results indicate that when IGF-1R is present at a high level, a considerable synergistic effect can be achieved by co-administration of a c-Met/EGFR dual inhibitor and an IGF-1R inhibitor.

Example 2: Examination of Effect of Co-Administration of ME22S and an IGF-1R Inhibitor in Gastric Cancer Cells As identified from Example 1, IGF-1R is not found in gastric cell line SNU5 and the level of EGFR in gastric cell line SNU668 is higher than that of the gastric cell lines. In these two cell lines, the cell proliferation inhibition effect of co-administration of ME22S and an IGF-1R inhibitor linsitinib was examined.

In particular, SNU5 or SNU668 cells were seeded on 96-well plates at the amount of 5000 cells/well (medium used: RPMI (GIBCO); culture conditions: 5% $CO_2$ and 37° C.), and 24 hours after, treated with ME22S and linsitinib. 72 hours after the co-treatment, the cell number was measured by CellTiter Glo assay (Promega, G7573). Linsitinib was treated at a fixed concentration of 10 μM, and ME22S was treated at the 1/5 diluted concentration starting from 60 nM (see FIG. 2). For comparison, cells were treated with the same concentrations of ME22S in the absence of linsitinib.

Figure 2:
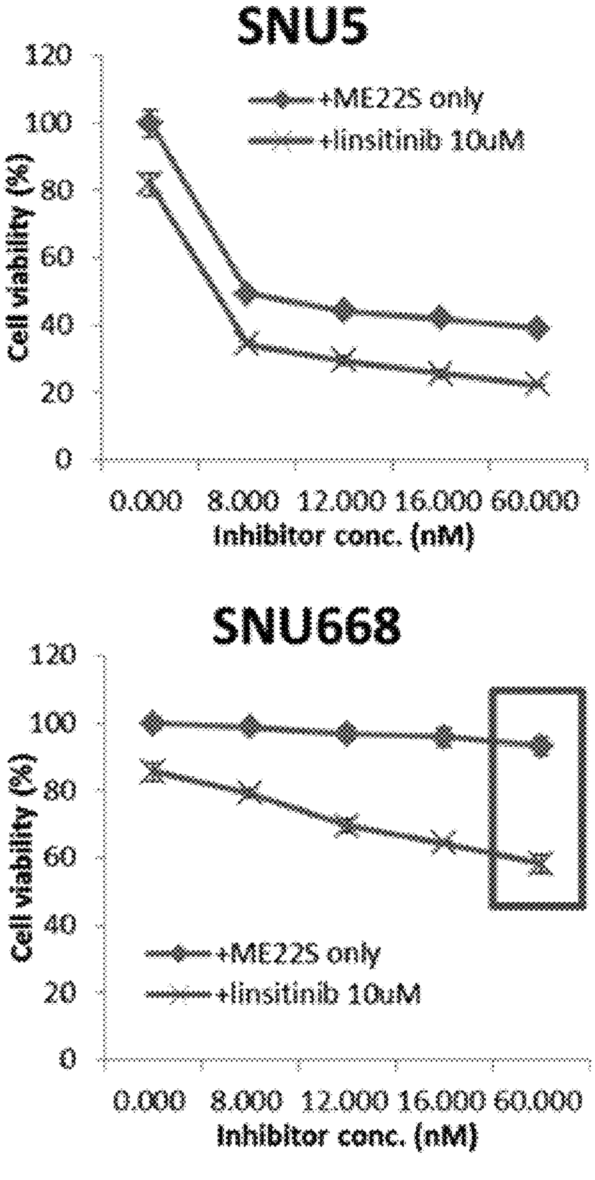
FIG. 2 provides graphs showing cancer cell proliferation inhibiting effects of combined administration of an anti-c-Met/anti-EGFR bispecific antibody and linsitinib in gastric cancer cell lines SNU5 and SNU668.

The results, shown in FIG. 2, indicate that there was no synergistic effect by co-administration of ME22S and linsitinib in cell line SNU5, on which ME22S has a cell proliferation inhibition effect even when it is administered alone; whereas in cell line SNU668 on which ME22S does not exhibit a cell proliferation inhibition effect when it is administered alone, a synergistic anticancer effect can be achieved by co-administration of ME22S and linsitinib.

Example 3: Examination of Effect of Co-Administration of ME22S and an IGF-1R Inhibitor in Lung Cancer Cells In order to examine a synergistic effect of co-administration of ME22S and an IGF-1R inhibitor in a lung cancer cell line on which ME22S does not exhibit its effect (e.g., cell proliferation inhibition effect) when it is administered alone, the HCC827 cell line was used.

HCC827 cell line were seeded at 5000 cells/well on a 96-well plate (medium: RPMI (GIBCO); culture condition: 5% $CO_2$ and 37° C.), and 24 hours after, treated with ME22S and linsitinib together. 72 hours after the co-treatment, the number of living cells was counted by CellTiter Glo assay (Promega, G7573). Linsitinib was treated at a fixed concentration of 10 μM, and ME22S was treated at the 1/5 diluted concentration starting from 150 nM (see FIG. 3A). For comparison, the same experiment was performed except cells were treated with ME22S alone at the 1/5 diluted concentration starting from 150 nM or linsitinib alone at the concentration of 10 μM.

Figure 3A:
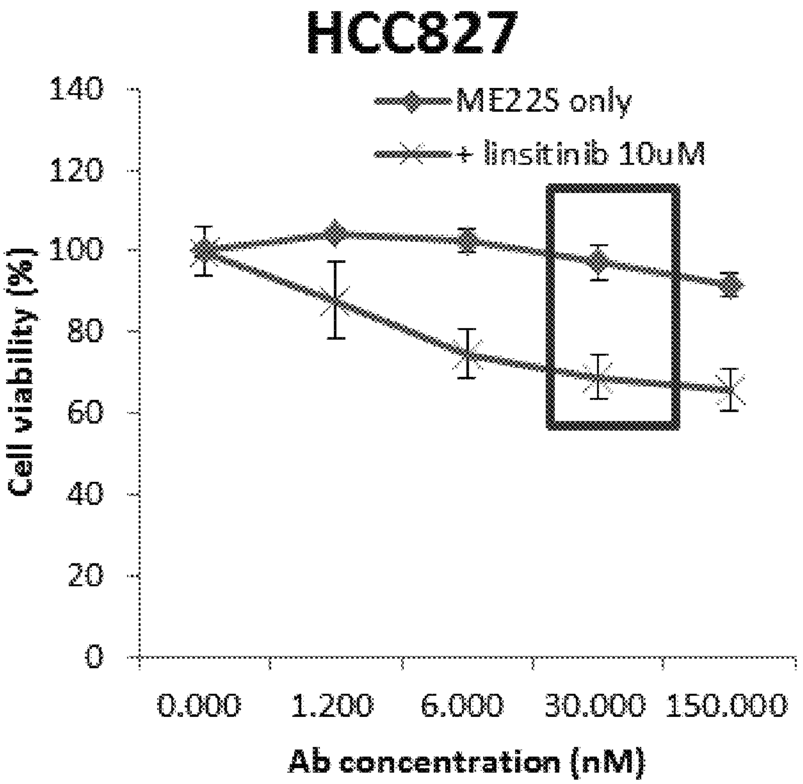
FIG. 3A is a graph showing cancer cell proliferation inhibiting effects of combined administration of anti-c-Met/anti-EGFR bispecific antibody ME22S and linsitinib in lung cancer cell line HCC827, depending on the concentrations of ME22S.
Figure 3B:
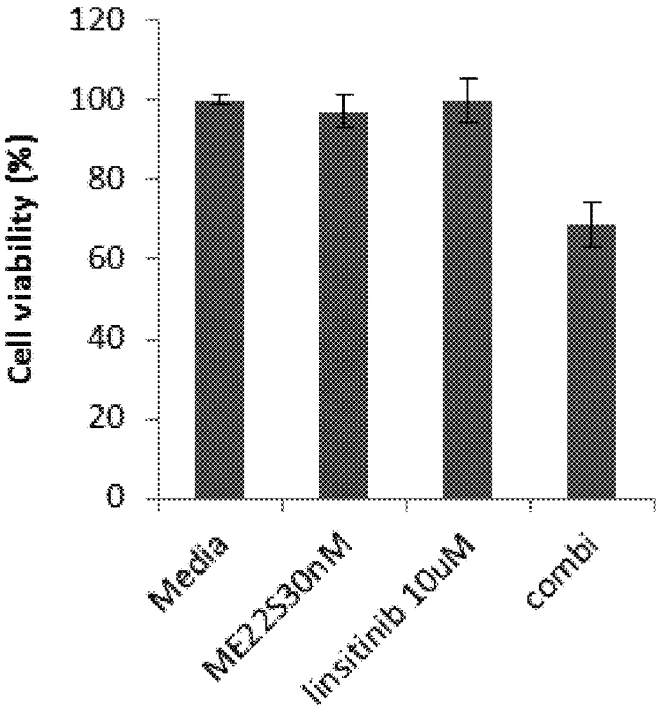
FIG. 3B is a graph showing cancer cell proliferation inhibiting effects of combined administration of ME22S and linsitinib and administration of ME22S only or linsitinib only in lung cancer cell line HCC827 at the concentrations of 30 nM of ME22S and 10 μM of linsitinib.

The results from these experiments are shown in FIGS. 3A and 3B. FIG. 3A shows degrees of cancer cell proliferation depending on the concentrations of ME22S. FIG. 3B shows degrees of cancer cell proliferation at the concentrations of 30 nM of ME22S and 10 μM of linsitinib. As shown in FIGS. 3A and 3B, in HCC827 cells, a cancer cell proliferation inhibition effect is observed when ME22S and linsitinib are administered together, whereas it is not observed when ME22S or linsitinib is administered alone.

Example 4: Examination II of Effect of Co-Administration of ME22S and an IGF-1R Inhibitor in Gastric Cancer Cells In order to examine a synergistic effect of co-administration of ME22S and an IGF-1R inhibitor in a gastric cancer cell line on which ME22S exhibits its effect (cell proliferation inhibition effect) even when it is administered alone, the MKN45 cell line was employed.

MKN45 cell line were seeded at 5000 cells/well on a 96-well plate (medium: RPMI (GIBCO); culture condition: 5% $CO_2$ and 37° C.), and 24 hours after, treated with ME22S and linsitinib together. 72 hours after the co-treatment, the number of living cells was counted by CellTiter Glo assay (Promega, G7573). Linsitinib was treated at a fixed concentration of 10 μM, and ME22S was treated at the 1/5 diluted concentration starting from relatively low concentration of 10 nM (see FIG. 4A) since ME22S alone can inhibit proliferation of the MKN45 cell line. For comparison, the same experiment was performed except the cells were treated with ME22S alone at the 1/5 diluted concentration starting from 10 nM or linsitinib alone at the concentration of 10 μM.

Figure 4A:
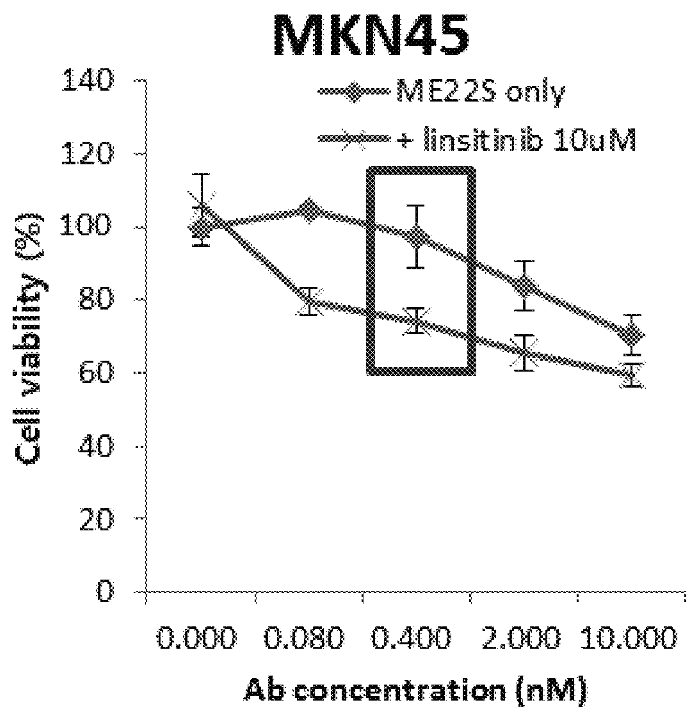
FIG. 4A is a graph showing cancer cell proliferation inhibiting effects of combined administration of anti-c-Met/anti-EGFR bispecific antibody ME22S and linsitinib in gastric cancer cell line MKN45, depending on the concentrations of ME22S.
Figure 4B:
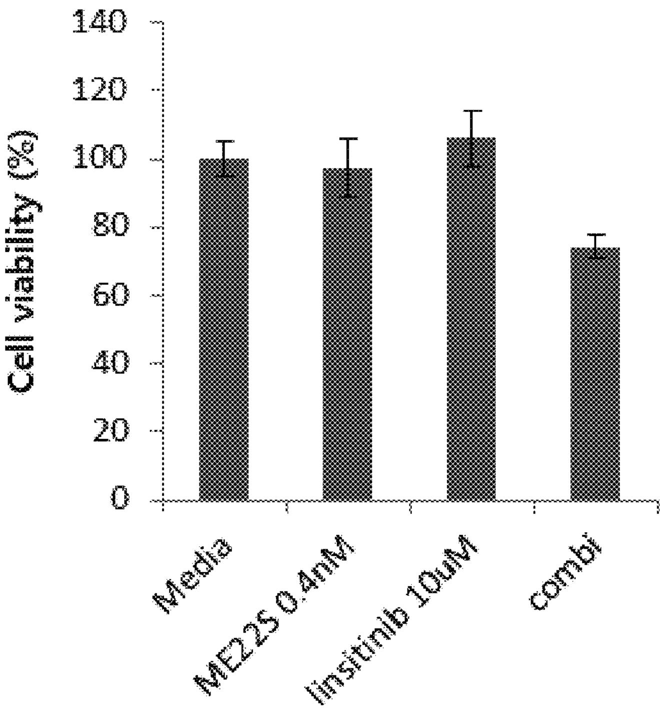
FIG. 4B is a graph showing cancer cell proliferation inhibiting effects of combined administration of ME22S and linsitinib and administration of ME22S only or linsitinib only in gastric cancer cell line MKN45 at the concentrations of 0.4 nM of ME22S and 10 μM of linsitinib.

The results from these experiments are shown in FIGS. 4A and 4B. FIG. 4A shows degrees of cancer cell proliferation depending on the concentration of ME22S. FIG. 4B shows degrees of cancer cell proliferation at the concentrations of 0.4 nM of ME22S and 10 μM of linsitinib. As shown in FIGS. 4A and 4B, in MKN45 cells, increased cancer cell proliferation inhibition is observed when ME22S and linsitinib are administered together, compared to when ME22S or linsitinib is administered alone. In addition, the increased cancer cell proliferation inhibition can be achieved at the relatively low concentration (such as about 0.4 nM) of ME22S when ME22S is administered together with linsitinib, indicating that the dose of each drug (i.e., c-Met/EGFR dual inhibitor ME22S or IGF-1R inhibitor linsitinib) can be reduced by co-administration thereof.

Example 5: Examination of Effect of Co-Administration of ME22S and an IGF-1R Inhibitor in Anti-c-Met Antibody Resistant Gastric Cancer Cells Anti-c-Met antibody resistance acquired gastric cancer cells, obtained by long term-administering anti-c-Met antibody L3-1Y/IgG2 prepared in Reference Example 1 to MKN45 cells (JCRB 0254) on which anti-c-Met antibody L3-1Y/IgG2 exhibits its effect (e.g., cancer cell proliferation inhibition effect) when it is administered alone, were used for the following experiment.

To obtain anti-c-Met antibody resistant MKN45 gastric cancer cells, MKN45 gastric cancer cells were administered with L3-1Y/IgG2 for at least 3 months by increasing the administration concentration. The amount of L3-1Y/IgG2 administered was increased from 1 μg/ml to 10 μg/ml, until resistance to L3-1Y/IgG2 is induced. The obtained L3-1Y/IgG2 resistant clones were named as MKN45re#1 and MKN45re#24, respectively.

It was confirmed that the obtained anti-c-Met antibody (L3-1Y/IgG2) resistant MKN45 gastric cancer cell line is also resistant to ME22S.

Each of the L3-1Y/IgG2 resistant MKN45re#1 and MKN45re#24 cell lines were seeded on a 96-well plate at the amount of 5000 cells/well (medium: RPMI (GIBCO); culture condition: 5% $CO_2$ and 37° C.), and 24 hours after, treated with ME22S and linsitinib together. 72 hours after the co-treatment, the number of living cells was counted by CellTiter Glo assay (Promega, G7573). Linsitinib was treated at a fixed concentration of 10 μM (MKN45re#1) or 2.5 μM (MKN45re#24), and ME22S was treated at the 1/5 diluted concentration starting from 10 nM (see FIG. 5). For comparison, the same experiment was preformed except that cells were treated with ME22S alone at the 1/5 diluted concentration starting from 10 nM.

Figure 5:
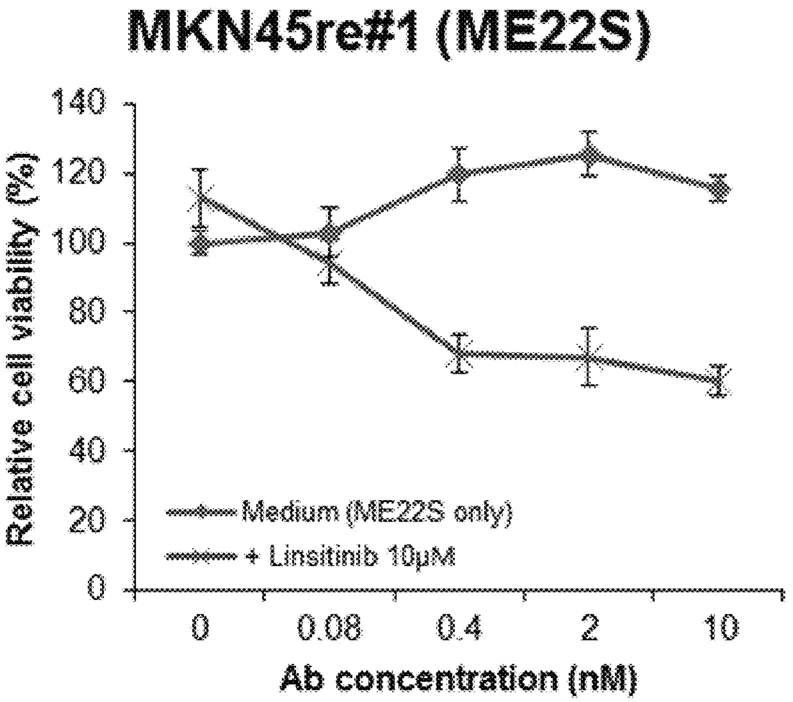
FIG. 5 provides graphs showing cancer cell proliferation inhibiting effects of combined administration of ME22S and linsitinib in anti-c-Met antibody resistant cell line MKN45, which has resistance to ME22S as well as anti-c-Met antibody L3-1Y-IgG2 (//note: we will provide related data together with our final instruction).
Figure 5:
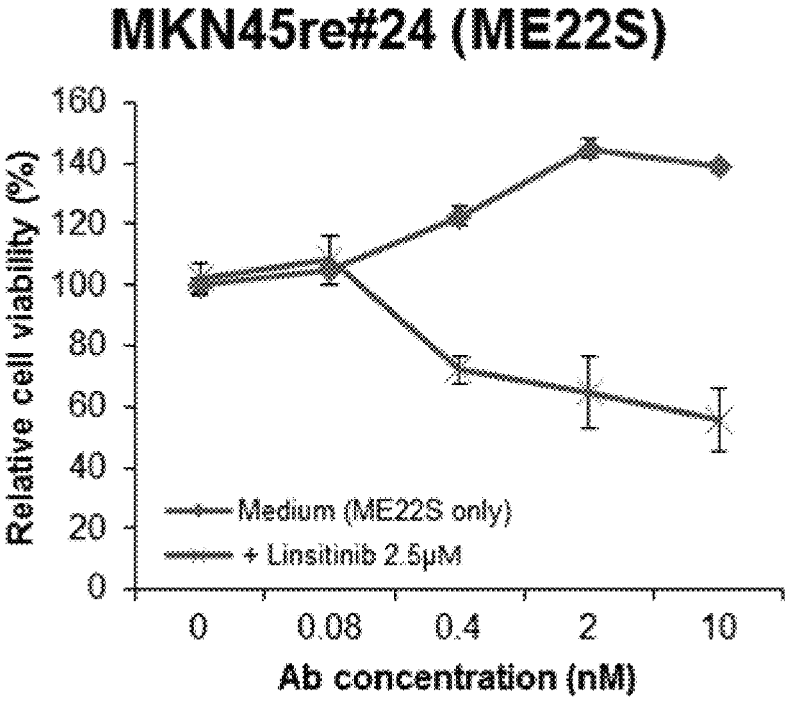

The results from this experiment are shown in FIG. 5. As shown in FIG. 5, in the L3-1Y/IgG2 resistance acquired MKN45 cell line, the administration of ME22S alone has no cancer cell proliferation inhibition effect (instead, leads to increase in cancer cell proliferation); whereas the combined administration of ME22S and linsitinib causes considerable cancer cell proliferation inhibition. These results indicate that the anticancer effect can be restored by combined administration of ME22S and linsitinib, even on a cell line on which ME22S alone loses its anticancer effect.

Example 6: Examination of Effect of Co-Administration of ME22S and an IGF-1R Inhibitor in Anti-c-Met Antibody Resistant Gastric Cancer Cells Changes in the activities (e.g., phosphorylation) of downstream proteins upon co-administration of ME22S and linsitinib to the L3-1Y/IgG2 resistant cell line MKN45re#1 prepared in Example 5 were measured. In particular, the cell line was seeded on 60 mm plate at the amount of $2\times10^5$ cells/ml, and 24 hours after, treated with antibody ME22S (10 nM) provided in serum-free condition and/or linsitinib (10 μM) for 30 minutes. Thereafter, the phosphorylation degrees of c-Met and AKT were measured by western blotting.

Figure 6:
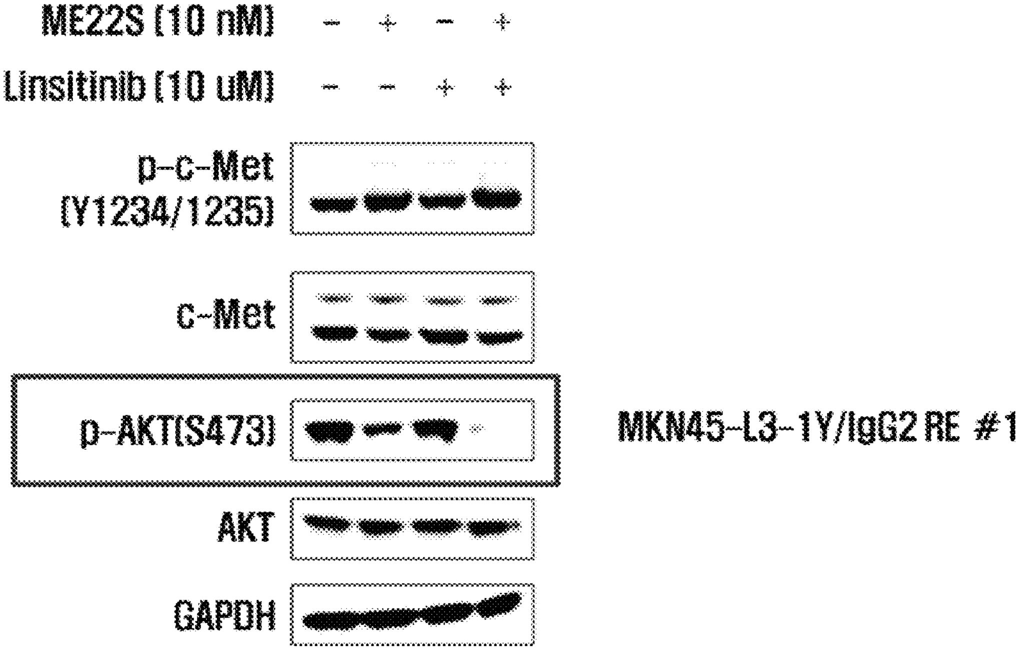
FIG. 6 provides western blotting results showing the changes in activities of downstream proteins by combined administration of an anti-c-Met/anti-EGFR bispecific antibody and linsitinib.

The results are shown in FIG. 6. As shown in FIG. 6, when the L3-1Y/IgG2 resistant cell line MKN45re#1 is treated with ME22S and linsitinib, the activity of p-AKT which is a downstream protein related to tumorigenesis is inhibited.

Example 7: Measurement of Degree of IGF-1R Activation in a Lung Cancer Cell Line Co-Treated with ME22S and Linsitinib It is possible to detect an activated site of IGF-1R using an antibody for immunoblotting of p-IGF-1R beta.

Lung cancer cell line HCC827 (ATCC, CRL-2868) was seeded on 60 mm plate at the amount of $2\times10^5$ cells/ml, and 24 hours after, treated with antibody ME22S (10 nM) provided in serum-free condition and/or linsitinib (10 μM) for 30 minutes. Thereafter, the phosphorylation degree of IGF-1R was measured by western blotting using an anti-p-IGF1R beta antibody (Cell signaling).

Figure 7:
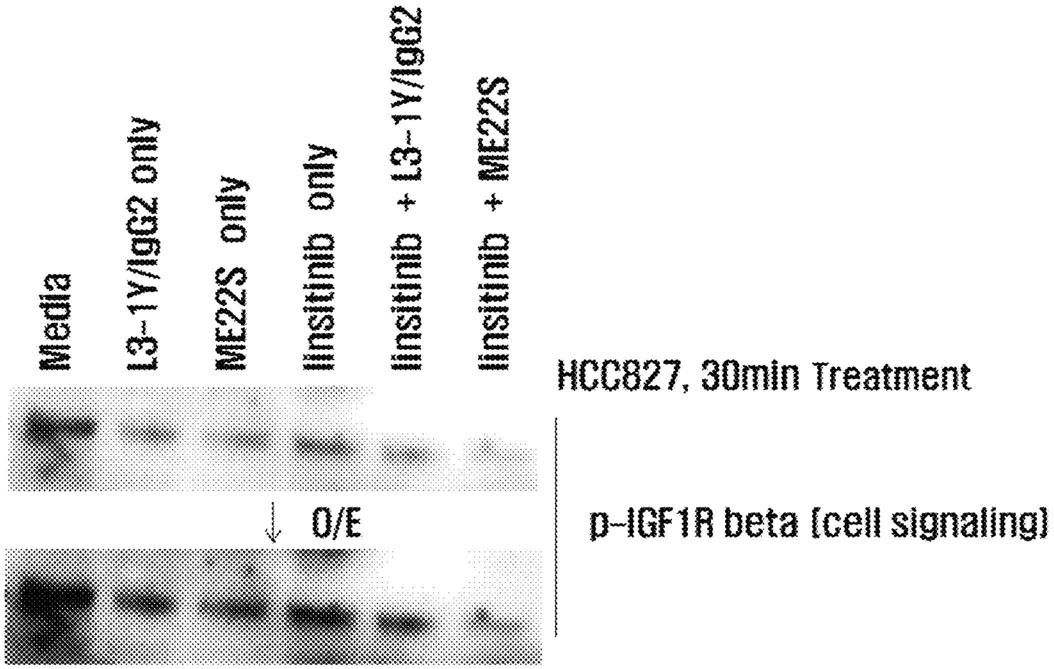
FIG. 7 provides western blotting results showing the level of IGF-1R protein, when an anti-c-Met/anti-EGFR bispecific antibody and linsitinib are administered together or respectively.

The results are shown in FIG. 7. As shown in FIG. 7, the co-treatment of ME22S and linsitinib leads to a decrease in the level of p-IGF-1R, indicating that the simultaneous inhibition of all of c-Met, EGFR and IGF-1R is more effective compared to the inhibition of one or two of c-Met, EGFR and IGF-1R.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a cancer in a subject, comprising co-administering a c-Met/EGFR dual inhibitor and an insulin-like growth factor 1 receptor (IGF-1R) inhibitor to the subject, wherein the c-Met/EGFR dual inhibitor comprises:

1) an anti-c-Met antibody or an antigen-binding fragment thereof, and 2) an anti-EGFR antibody, an antigen-binding fragment thereof, or an anti-EGFR DARPin, wherein the anti-c-Met antibody or an antigen-binding fragment thereof recognizes or binds to a polypeptide comprising 5 to 19 contiguous amino acid residues within SEQ ID NO: 71, wherein the polypeptide comprises at least SEQ ID NO: 73, and the anti-EGFR antibody, an antigen-binding fragment thereof, or an anti-EGFR DARPin comprises:

a) CDR-H1 comprising the amino acid sequence of SEQ ID NO: 109, CDR-H2 comprising the amino acid sequence of SEQ ID NO: 110, CDR-H3 comprising the amino acid sequence of SEQ ID NO: 111, CDR-L1 comprising the amino acid sequence of SEQ ID NO: 112, CDR-L2 comprising the amino acid sequence of SEQ ID NO: 113, and CDR-L3 comprising the amino acid sequence of SEQ ID NO: 114, b) at least one selected from the group consisting of cetuximab, panitumumab, an anti-EGFR antibody or an antigen-binding fragment thereof comprising a heavy chain variable region of SEQ ID NO: 121 and a light chain variable region of SEQ ID NO: 123, and an anti-EGFR antibody or an antigen-binding fragment thereof comprising a heavy chain variable region of SEQ ID NO: 125 and a light chain variable region of SEQ ID NO: 126, or c) 1 to 10 anti-EGFR DARPin units, each of which is independently selected from the group consisting of SEQ ID NOs: 127 to 130, and wherein the cancer is gastric cancer or lung cancer that is resistant to treatment with an anti-c-Met antibody or a c-Met/EGFR dual inhibitor in the absence of an IGF-1R inhibitor.

2. The method of claim 1, wherein the c-Met/EGFR dual inhibitor and an IGF-1R inhibitor are in a single or mixed formulation, or each of the c-Met/EGFR dual inhibitor and an IGF-1R inhibitor are administered in separate compositions, simultaneously or sequentially in any order.

3. The method of claim 1, wherein the anti-c-Met antibody or an antigen-binding fragment thereof comprises:

a CDR-H1 comprising SEQ ID NO: 4; a CDR-H2 comprising SEQ ID NO: 2, SEQ ID NO: 5, or an amino acid sequence comprising 8-19 consecutive amino acids within SEQ ID NO: 2 comprising the 3$^{rd}$ to 10$^{th}$ positions of SEQ ID NO: 2; a CDR-H3 comprising SEQ ID NO: 6, SEQ ID NO: 15, SEQ ID NO: 85, or an amino acid sequence comprising 6-13 consecutive amino acids within SEQ ID NO: 85 comprising the 1$^{st}$ to 6$^{th}$ positions of the amino acid sequence of SEQ ID NO: 85, a CDR-L1 comprising SEQ ID NO: 7, a CDR-L2 comprising SEQ ID NO: 8, and a CDR-L3 comprising SEQ ID NO: 9, SEQ ID NO: 15, SEQ ID NO: 86, or 9-17 consecutive amino acids within SEQ ID NO: 89 comprising the 1$^{st}$ to 9$^{th}$ positions of SEQ ID NO: 89.

4. The method of claim 3, wherein the anti-c-Met antibody or an antigen-binding fragment thereof comprises:

a heavy chain variable region comprising a CDR-H1 comprising SEQ ID NO: 1, 22, 23, or 24, a CDR-H2 comprising SEQ ID NO: 2, 25, or 26, and a CDR-H3 comprising SEQ ID NO: 3, 27, 28, or 85;

a light chain variable region comprising a CDR-L1 comprising SEQ ID NO: 10, 29, 30, 31, 32, 33, or 106, a CDR-L2 comprising SEQ ID NO: 11, 34, 35, or 36, and a CDR-L3 comprising SEQ ID NO: 12, 13, 14, 15, 16, 37, 86, or 89; or a combination thereof.

5. The method of claim 3, wherein the anti-c-Met antibody or an antigen-binding fragment thereof comprises:

a heavy chain variable region comprising SEQ ID NO: 17, 74, 87, 90, 91, 92, 93, or 94;

a light chain variable region comprising SEQ ID NO: 131, 18, 19, 20, 21, 75, 88, 95, 96, 97, 98, 99, or 107; or a combination thereof.

6. The method of claim 3, wherein the anti-c-Met antibody comprises:

a heavy chain comprising SEQ ID NO: 62, an amino acid sequence from the 18$^{th}$ to 462$^{nd}$ positions of SEQ ID NO: 62, SEQ ID NO: 64, an amino acid sequence from the 18$^{th}$ to 461$^{st}$ positions of SEQ ID NO: 64, SEQ ID NO: 66, or an amino acid sequence from the 18th to 460$^{th}$ positions of SEQ ID NO: 66; and a light chain comprising SEQ ID NO: 68, an amino acid sequence from the 21$^{st}$ to 240$^{th}$ positions of SEQ ID NO: 68, SEQ ID NO: 70, an amino acid sequence from the 21$^{st}$ to 240$^{th}$ positions of SEQ ID NO: 70, or SEQ ID NO: 108.

7. The method of claim 1, wherein the anti-EGFR antibody or an antigen-binding fragment thereof comprises:

a heavy chain variable region comprising SEQ ID NO: 115, 117, 121, or 125;

a light chain variable region comprising SEQ ID NO: 116, 118, 123, or 126; or a combination thereof.

8. The method of claim 1, wherein the c-Met/EGFR dual inhibitor comprises:

1) an anti-c-Met antibody and 2) an antigen-binding fragment of an anti-EGFR antibody or an anti-EGFR DARPin comprising 1 to 10 anti-EGFR DARPin units, each of which is independently selected from the group consisting of SEQ ID NOs: 127 to 130, wherein the antigen-binding fragment of an anti-EGFR antibody or the anti-EGFR DARPin is linked to the C-terminus of the anti-c-Met antibody.

9. The method of claim 1, wherein the IGF-1R inhibitor comprises at least one selected from the group consisting of an antibody, an aptamer, siRNA, shRNA, microRNA, a small molecule IGF-1R inhibitor, and a pharmaceutically acceptable salt thereof.

10. The method of claim 1, wherein the IGF-1R inhibitor is at least one selected from the group consisting of linsitinib, NVP-AEW541, GSK1904529A, NVP-ADW742, BMS-536924, figitumumab, cixutumumab, dalotuzumab, R1507, XL-228, INSM-18, BMS-754807, AG-1024, GSK1838705A, PQ 401, and pharmaceutically acceptable salts thereof.

11. The method of claim 1, wherein the cancer is characterized by overexpression of c-Met.

* * * * *